US012683018B2

(12) United States Patent
    Campbell et al.

(10) Patent No.: US 12,683,018 B2
(45) Date of Patent: Jul. 14, 2026

(54) REVERSE SUPPLY CHAIN GATEWAY FOR MEDICAL EQUIPMENT

(71) Applicant: reLink Medical, LLC, Twinsburg, OH (US)

(72) Inventors: Scott A. Campbell, Hudson, OH (US); Jeremy A. Dalton, Hudson, OH (US); Jeffrey D. Dalton, Chagrin Falls, OH (US); Arthur R. Dalton, Aiken, SC (US)

(73) Assignee: reLink Medical, LLC

( * ) Notice: Subject to any disclaimer, the term of this patent is extended or adjusted under 35 U.S.C. 154(b) by 221 days.

(21) Appl. No.: 18/441,584

(22) Filed: Feb. 14, 2024

(65) Prior Publication Data

US 2025/0259741 A1     Aug. 14, 2025

(51) Int. Cl.
    G16H 40/40          (2018.01)

(52) U.S. Cl.
    CPC .................................... G16H 40/40 (2018.01)

(58) Field of Classification Search
    CPC ............................... G16H 40/40; G16H 40/20
    See application file for complete search history.

(56) References Cited

U.S. PATENT DOCUMENTS

| 7,110,967 B1 * | 9/2006 | Espenes ............. | G06Q 30/0641 705/7.29 |
| 9,589,247 B2 * | 3/2017 | Bolene ................... | G16H 40/20 |
| 2002/0116348 A1 * | 8/2002 | Phillips ................. | G06Q 30/06 705/400 |

FOREIGN PATENT DOCUMENTS

CN          112132639 A  * 12/2020  ......... G06Q 30/0206

OTHER PUBLICATIONS

Yan Zhang & Yanyan He & Jinfeng Yue & Qinglong Gou, 2019. "Pricing decisions for a supply chain with refurbished products," International Journal of Production Research, Taylor & Francis Journals, vol. 57(9), pp. 2867-2900, May 2019.*

* cited by examiner

*Primary Examiner* — Linh Giang Le
(74) *Attorney, Agent, or Firm* — Emerson Thomson and Bennett; Daniel A. Thomson

(57)          ABSTRACT

The Reverse Supply Chain Gateway for Used Medical Equipment is a time, resource, and value optimizer that eliminates gaps faced in the disposition process for medical equipment. By making the economics and resource requirements to participate feasible for all parties, healthcare systems and/or asset owners see increased service, better compliance, reduced costs, less environmental waste generated, and more capital returned. Meanwhile the downstream supply chain for reconditioning medical devices and harvesting parts to reenter the market for productive healthcare provider use is strengthened and expanded through access to significantly more equipment, reduced capital requirements to participate, increased information available about medical device conditions to make more informed purchases, less landfill consumption, and more equipment reuse. The efficiency gains from the UME Gateway enable the solutions and services it provides to more than pay for itself for all active participants.

1 Claim, 15 Drawing Sheets

REVERSE SUPPLY CHAIN GATEWAY FOR MEDICAL EQUIPMENT

FIELD

The present teaching relates generally to an artificial intelligence ("AI") guided system and method for providing a platform for buying and selling medical equipment.

BACKGROUND

Significant gaps exist between healthcare systems and/or asset owners needing to dispose of excess medical equipment and the vendors who recondition and resell these medical devices and parts. Healthcare systems and/or asset owners must properly and efficiently dispose of every excess and out of service medical device they own regardless of device type, condition, usefulness, or residual value, and they must do so in a manner that complies with federal, state, and local regulations and their own internal governance policies. Meanwhile reconditioning and parts vendors are typically only interested in meeting a fraction of a healthcare system's and/or asset owner's entire disposition need. These vendors seek to acquire only the specific types of devices they specialize in (for example laboratory, surgical tools, imaging, infusion pumps, and so forth), and even then, are only interested in handling disposition of useful and marketable assets rather than items with no value. These vendors also have an extremely hard time determining the exact functional and cosmetic condition, specifications, accessories, and history of each unique medical device to make informed purchase decisions because the healthcare systems and/or asset owners are understaffed and rightly focused on patient care priorities rather than collecting and disseminating this information for the high volume of devices they are getting rid of.

Neither party can optimize the economic, environmental, and reuse potential for disposing of all medical devices. Healthcare systems and/or asset owners must unnecessarily consume valuable technician and provider time as well as scarce facility space to support disposition which ultimately impacts speed and cost of care. Meanwhile they receive less than maximum value from their equipment disposition processes, and many devices end up in trash dumpsters, recycling centers and landfills rather than repurposed in ways that can extend their useful life to improve quality and access to healthcare elsewhere.

Shortcomings with traditional reverse supply chain approaches cannot fill this gap for the healthcare industry as it pertains to medical devices. Typical marketplace models connect buyers and sellers but leave detailed product information gathering, transaction completion, service, and fulfillment execution to the parties themselves which is practically infeasible for healthcare systems and/or asset owners to support. Typical full-service disposition or recycling operations serve much larger consumer and general business product marketplaces rather than the highly regulated niche market for industrial medical equipment which has limited product standards or compatibility across makes and models, relatively few accessible buyers or demand centers, high repair costs and mandatory requirements to restore medical equipment to patient-ready condition, extreme aftermarket price volatility, and buyers and sellers requiring unique device information, economic terms, and compliance solutions to do business. This market requires a different approach to efficiently and effectively repurpose excess and end of life medical equipment from healthcare systems and/or asset owners.

Some of the technologies and technical terms used herein are as follows:

Artificial Intelligence (AI): Artificial Intelligence refers to machine learning natural language processing, and predictive analysis models and technologies that can operate independently of human interaction, interference, or supervision.

Crawler: A crawler (sometimes referred to as a "web crawler") is a tool used by AI algorithms or other automated mechanisms to systematically browse the internet using various internet protocols. The data harvested by crawlers is often used for training AI algorithms and in model creation or processed by AI models to produce usable outputs for both humans and other AI models to consume.

Lotting: A combination of items that buyers can conveniently purchase in their entirety regardless of any similarity or relationship between the items which may or may not exist.

Kitting: A gathering of items into a collection or kit that work together to serve a specific purpose such as a set of surgical instruments designed for a specific procedure or a complete ultrasound or patient monitoring system with necessary compatible parts and accessories.

CMMS: A Computerized Maintenance Management System (CMMS) is software that helps manage assets, schedule maintenance, and track work orders. Healthcare systems and/or asset owners of medical devices use a CMMS as their system of record for tracking medical devices while they are in use by that organization. A CMMS helps to optimize the utilization and availability of medical equipment and contains a data model that organizes information about the assets that need to be maintained and the resources needed to maintain those assets. The CMMS has several capabilities, including tracking maintenance schedules, resource/labor management, asset registries, work order management, preventative maintenance automation, materials/inventory management, parts order generation, and end of life tracking and reporting.

Electronic Protected Health Information (ePHI): Electronic Protected Health Information is protected health information that is produced, saved, transferred, or received in an electronic form. Rules and protocols regarding the handling ePHI are governed by The Health Insurance Portability and Accountability Act of 1996 (HIPAA), also known as the HIPAA Security Rule. The HIPAA Security Rule regulates risk analysis and management; creates administrative, physical, and technical safeguards; requires special documentation and handling; and contains enforcement and penalties for non-compliance. These special rules and regulations regarding ePHI make it important to ensure that ePHI is handled properly and with care to avoid unintended or unlawful disclosure. As related to the subject matter herein ePHI may sometimes exist on medical devices at the time they are disposed of creating a disclosure risk for the device owner.

ISO: Independent Service Organizations (ISOs) are organizations that provide services and support that fall outside of a company's normal skillset, or on a scale that a company might struggle to deal with efficiently and/or effectively. Healthcare systems and/or asset owners of medical devices often contract with ISOs to install, repair, test and maintain their medical equipment inventory while it is in use providing patient care. As related to the subject matter herein healthcare systems typically need to include ISO staff in their medical equipment disposition processes and/or ISOs may provide medical equipment disposition services to their healthcare system customers.

GPO: Group Purchasing Organizations (GPOs) are entities that help healthcare providers to realize savings and efficiencies by aggregating purchasing volume and using that leverage to negotiate discounts with manufacturers, distributors, and other vendors. As related to the subject matter herein GPOs may offer or promote third-party medical equipment disposition services to their healthcare system customers or track third-party managed disposition programs.

Healthcare System: A healthcare system is an organization of people, institutions, and resources that delivers health care services to meet the health needs of target populations and may include a variety of locations including hospitals, clinics, laboratory testing facilities, treatment centers and more.

Asset Owner: An asset owner is an entity that is not a healthcare system but still owns and/or possesses medical equipment. This includes but is not limited to independent doctor offices, imaging centers, dental practices, veterinary clinics, and many other forms of healthcare providers, manufacturers, or other types of companies that own or possess medical equipment.

Medical equipment: As used hereinafter, the terms "medical equipment" and "medical device" include new, refurbished, and used medical equipment.

SUMMARY

The Reverse Supply Chain Gateway for Used Medical Equipment ("UME Gateway") is a time, resource, and value optimizer that eliminates gaps faced in the disposition process for medical equipment. By making the economics and resource requirements to participate feasible for all parties, healthcare systems and/or asset owners see increased service, better compliance, reduced costs, and more capital returned. Meanwhile downstream supply chain vendors who recondition specific types of medical devices and harvest parts to reenter the market for productive healthcare provider usage are strengthened and expanded through both easier access to, and significantly more information about available medical devices they might be interested in acquiring. The efficiency gains from the UME Gateway enable the solutions and services it provides to more than pay for itself for all active participants.

The UME Gateway system includes one or more storage machines holding instructions executable by one or more logic machines to: using AI, identify the at least one asset, recommend how much investment to make in gathering additional details about the at least one asset, and recommend the ideal course of action to take regarding the at least one asset, wherein the at least one asset is at least one piece of pre-owned medical equipment. The more accurate the UME Gateway's serialized level identification of the at least one asset, and the more specific information about the condition and accessories included with the at least one asset, the better the economic decision making about what to do with the at least one asset can be made by all parties. Since gathering this information is itself costly the UME Gateway uses an AI enhanced medical device recognition engine and process to efficiently identify the at least one asset, and AI driven econometric analytics to both determine the financial benefit of investing in more detailed information gathering about the at least one asset and define the recommended action to take with the at least one asset, wherein the econometric data includes demand, supply, transactional terms, activity costs, investments of parts and labor and other relevant data from within and outside the system. The UME Gateway then uses AI assisted process management capabilities to ensure the at least one asset moves through the recommended action steps to ultimately redeploy, recondition and/or resell, donate, or recycle the at least one asset.

The AI enhanced medical device recognition engine uses an acquisition and identification capture process, wherein incoming assets are photographed and entered in the system for identification. The models used by the AI enhanced medical device recognition engine determine what the at least one asset is and identify gaps in data, metadata, and master data about the at least one asset to automatically fill them in or generate alerts to cost-effectively guide human assisted intervention to enrich the data for decision making.

The AI driven econometric analytics used in making the recommendation regarding how much investment to make in identifying additional details about the at least one asset utilizes at least one of the following data sets in making its recommendations: manufacturer, model, quantity, condition, specification data, accessories, transaction history, registered demand, terms, quotes, offers, market supply data, market pricing signals, available compatible inventory, lotting options, kitting options, refurbishment valuation predictions, refurbishment costs, parts harvest valuation predictions, and parts harvest costs. The AI driven econometric analytics used in making the recommendation regarding how much investment to make in identifying additional details about the at least one asset further utilizes contract and governance rules and constraints in making its recommendations to the extent such rules and constraints dictate specialized information gathering requirements or limit the options available for the disposition of the at least one asset. The models used by the AI driven econometric analytics perform prework and use Crawlers in sourcing relevant market data and either process it into a machine consumable format or present it to a user to format for incorporation into the model.

Once the at least one asset is identified and desired information about it has been captured the system further employs an AI driven econometric analytics engine to make a recommendation regarding the ideal escape path, and if applicable, the initial offering price for the at least one asset based on information available, wherein the at least one asset is at least one piece of medical equipment, wherein the escape path options include: a store path, a redeploy path, a recondition path, a parts harvest path, a direct resale path, a merchandised resale path, a donate path, and a remediate or recycle path. The AI driven econometric analytics engine used in making the escape path and pricing recommendations analyzes at least one of the following factors from data captured from within or outside of the system: supply, manufacturer, model, quantity, condition, specification data, accessories, transaction history, registered demand, terms, quotes, offers, market supply data, market pricing signals, available compatible inventory, lotting options, kitting options, refurbishment valuation predictions, refurbishment costs, parts harvest valuation predictions, parts harvest costs, and potential channels for resale. In making an escape path or pricing recommendation for the at least one asset the AI driven econometric analytics normalizes relevant past transactions, market data, and current demand data by weighting it using available information on recency, product conditions, seasonal timing, volumes, number of historical transactions and data points, actual channels where transactions occurred, and combinations of items previously purchased or quoted simultaneously to determine ultimate potential pocket margin returns from different medical equipment escape path alternatives. When recommending an escape path, the AI driven econometric analytics compare the benefit of making value added investments of labor, logistics, and accessories into the at least one asset versus leaving it as is. The AI driven econometric analytics used in making the escape path recommendation for the at least one asset further utilizes contract and governance rules and constraints from the healthcare system and/or asset owner of the at least one asset in making its recommendations to the extent such rules and constraints dictate or limit the escape path options available for the at least one asset. The AI driven econometric analytics also computes a confidence rating in the escape path and pricing recommendations it has for the at least one asset such that higher confidence recommendations can be automatically acted upon while lower confidence recommendations can require human assisted support to approve actions. The system also utilizes quality control methods to ensure that there are no anomalies in the information used by the system to make the recommendation. The user of the system can dynamically control the factors that the system uses to make the recommendation and adjust or override and recommendation.

Once an escape path is determined for the at least one asset the UME Gateway provides several AI assisted automations to perform, track, course correct, and report on the execution of the escape path process itself. This includes automated interaction with multiple stakeholders including buyers, channels, marketplaces, value added reconditioning and parts vendors, healthcare systems and/or asset owners, and other medical device vendors. These automations help with cost-effectively processing the high volume of relatively low value medical devices healthcare systems and/or asset owners dispose of, allowing more devices to enter the reverse supply chain and avoid being recycled.

The UME Gateway employs additional AI assisted technologies to ensure financial tracking, posting, and compliance occurs across the complex nature of financial relationships that exist with healthcare systems and/or asset owners, trading partners that provide reconditioning and parts harvesting services, and the ultimate buyers of medical devices. These UME Gateway AI assisted technologies are able to combine the at least one asset from multiple sources, track investments of parts and labor from multiple parties into these at least one asset combinations, incorporate bartering arrangements and upstream and downstream consignment relationships, track yields and performance metrics, capture revenue transactions attributable to each at least one asset that may occur multiple times and/or over long periods, and ultimately split all residual earnings and charges back to the healthcare systems and/or asset owners involved while maintaining traceability, auditability, and adherence to established accounting standards.

The UME Gateway provides automated self-service portals, mobile device applications, and a full set of integration and configuration capabilities allowing healthcare systems and/or asset owners to effectively embed the UME Gateway into their preferred CMMS or other asset management systems and processes, automate scheduling of asset evaluations, pickups, and redeployments, generate credit redemptions, and access AI generated analytics and insights regarding the performance of their medical equipment disposition programs relative to industry standards and internal capabilities. These UME Gateway capabilities provide healthcare systems and/or asset owners the ability to uniquely tailor their medical device disposition programs across departments, locations, asset types, and more to meet their unique governance requirements, performance capabilities, organizational structure, and compliance and economic objectives, all at a lower cost than a one-size-fits-all disposition process.

The UME Gateway uses knowledge of a healthcare system's and/or asset owner's medical device inventory and disposition activity to provide AI generated guidance for optimizing capital planning, fleet maintenance and fleet life extension decisions. This guidance is tied to access to an exclusive UME Gateway online marketplace of reconditioned medical devices, parts, supplies and medical equipment services exclusively for UME Gateway healthcare systems and/or asset owners to act upon by exchanging earnings from medical devices they release to the UME Gateway for other needed products and services using financial models to multiply their earnings and automations to streamline cumbersome one-off small capital and operations purchasing events.

Still other benefits and advantages of the present subject matter will become apparent to those skilled in the art to which it pertains upon a reading and understanding of the following detailed specification.

BRIEF DESCRIPTION OF THE DRAWINGS

The disclosure may take physical form in certain parts and arrangement of parts, aspects of which will be described in detail in this specification and illustrated in the accompanying drawings which form a part hereof and wherein.

DETAILED DESCRIPTION

The following detailed description is merely exemplary in nature and is not intended to limit the described aspects or the application and uses of the described aspects. As used herein, the word "exemplary" or "illustrative" means "serving as an example, instance, or illustration." Any implementation described herein as "exemplary" or "illustrative" is not necessarily to be construed as preferred or advantageous over other implementations. All the implementations described below are exemplary implementations provided to enable persons skilled in the art to make or use the aspects of the disclosure and are not intended to limit the scope of the disclosure, which is defined by the claims.

Disclosed is a Reverse Supply Chain Gateway for Used Medical Equipment (UME Gateway). This UME Gateway may include one or more physical storage machines holding instructions executable by one or more logic machines to carry out tasks and methods described herein. For example, the instructions may be executable by the system or subsystems to carry out methods shown in the figures disclosed herein.

Figure 1A:
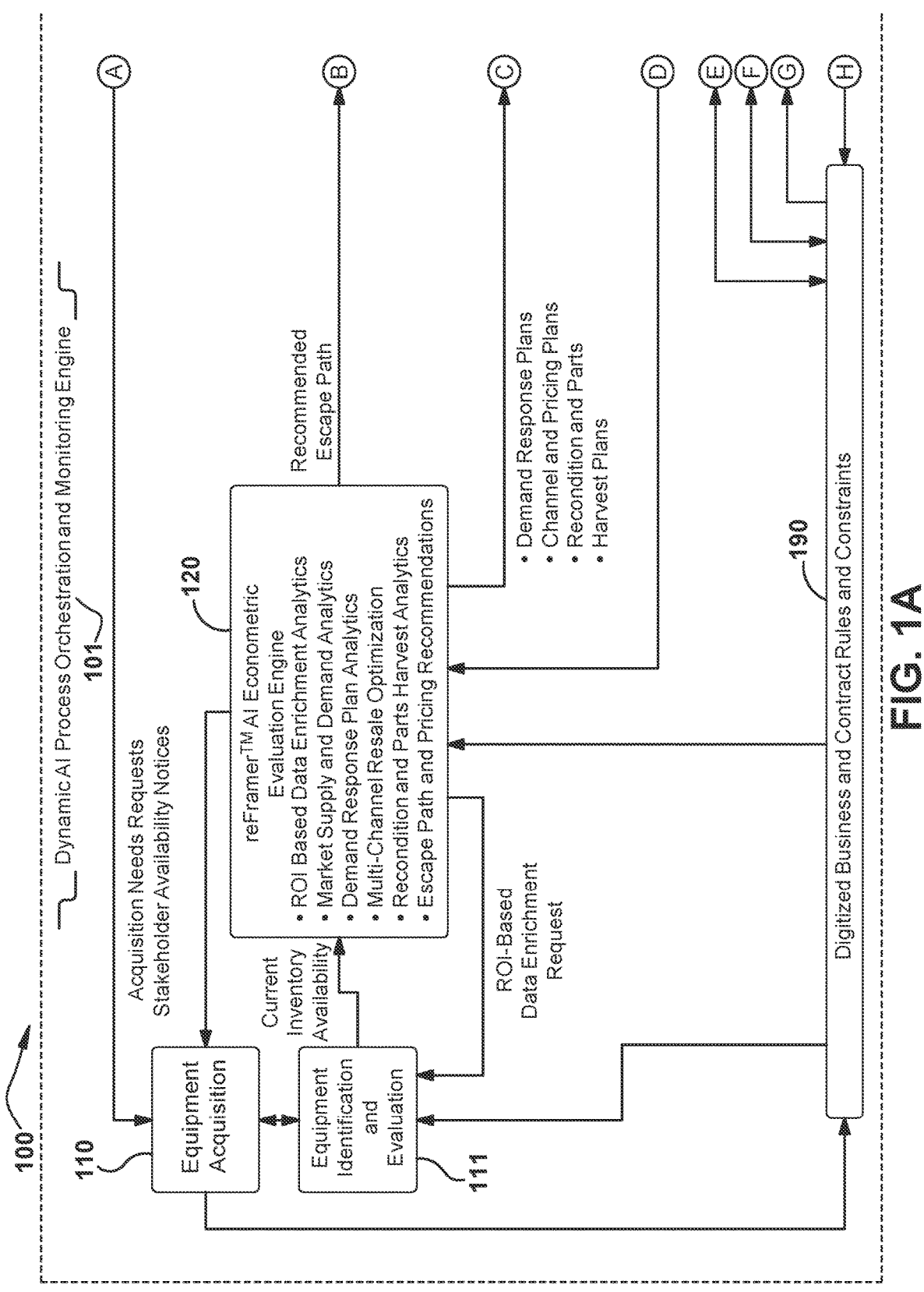
FIGS. 1*a* and 1*b* schematically present a flow chart giving an overview of the UME Gateway in accordance with aspects of the present disclosure.
Figure 1B:
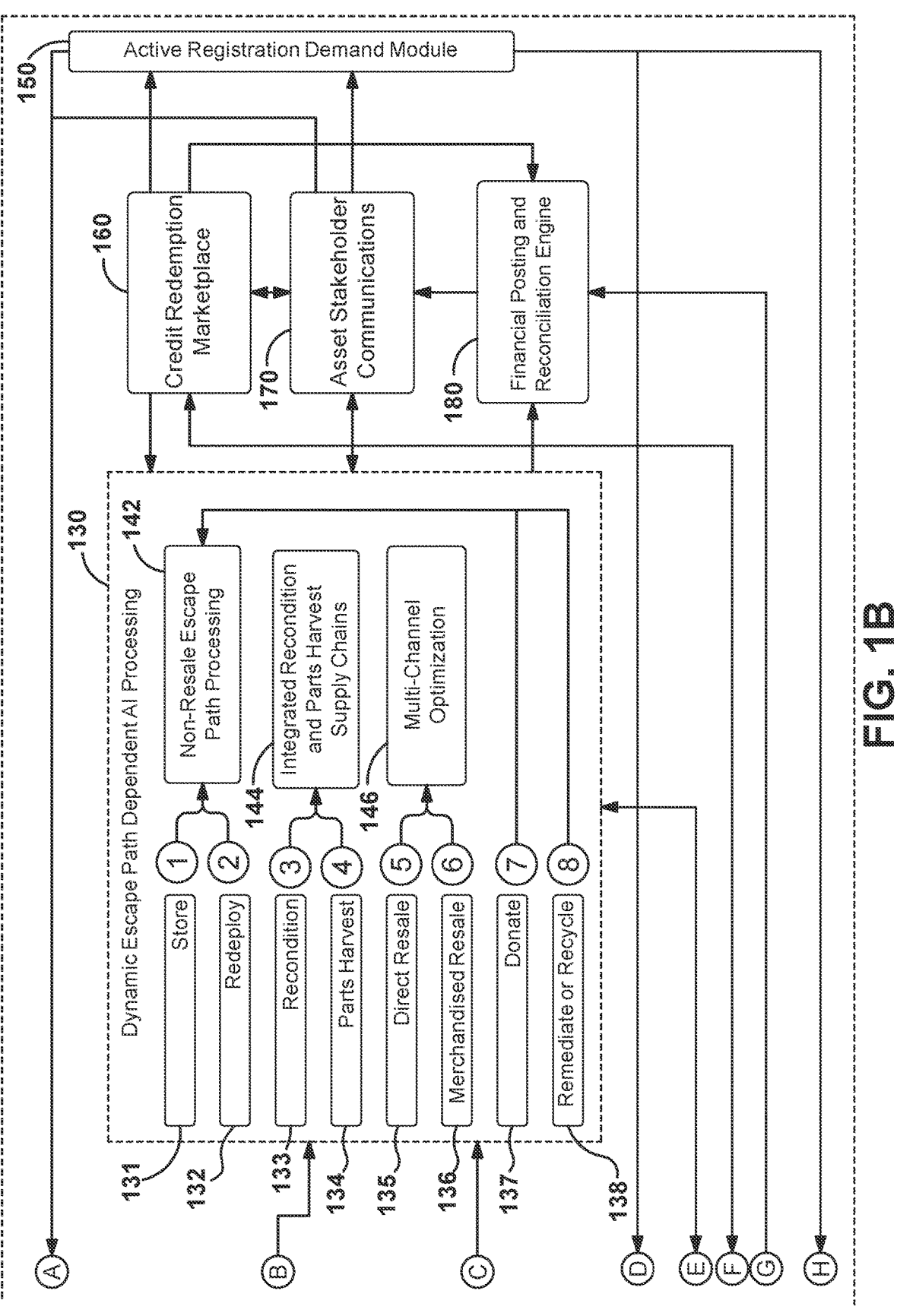

FIGS. 1a and 1b schematically present an Overview of Reverse Supply Chain Gateway for Used Medical Equipment (UME Gateway) flowchart 100 showcasing the high-level operational flow and key features throughout the UME Gateway. The Overview of Reverse Supply Chain Gateway for Used Medical Equipment (UME Gateway) flowchart 100 includes a Dynamic AI Process Orchestration and Monitoring Engine 101, an Equipment Acquisition process 110, an Equipment Identification and Evaluation process 111, a reFramer™ AI Econometric Evaluation Engine 120, a Dynamic Escape Path Dependent AI Processing group 130, an Active Registered Demand Module 150, a Credit Redemption Marketplace 160, an Asset Stakeholder Communications capability 170, a Financial Posting and Reconciliation Engine 180, and a Digitized Business and Contract Rules and Constraints database 190.

The Dynamic Escape Path Dependent AI Processing group 130 includes a Store path 131, a Redeploy path 132, a Recondition path 133, a Parts Harvest path 134, a Direct Resale path 135, a Merchandised Resale path 136, a Donate path 137, a Remediate or Recycle path 138, a Non-Resale Escape Path Processing engine 142, an Integrated Recondition and Parts Harvest Supply Chains processing engine 144, and a Multi-Channel Optimization resale processing engine 146.

The Dynamic AI Process Orchestration and Monitoring Engine 101 is a series of AI models and automations underpinning the entire UME Gateway that creates and guides automated and human assisted tasks, steps, and workflows, and detects and resolves or generates alerts on exceptions occurring during execution of processes throughout the UME Gateway. Details of the Dynamic AI Process Orchestration and Monitoring Engine 101 are described in FIGS. 4a and 4b.

The Equipment Acquisition process 110 is the process and supporting technologies by which medical devices are sourced or made available to the UME Gateway. Details of the Equipment Acquisition process 110 are described in detail in FIG. 3.

The Equipment Identification and Evaluation process 111 is where information about available medical equipment from the Equipment Acquisition process 110 is determined and formatted in a manner that can be processed by the UME Gateway. Image processing is combined with AI and other techniques to efficiently identify makes, models, conditions, system completeness, specifications, included accessories and other basic information about the acquired medical equipment to feed into subsequent analytics and decision making. Any ePHI or hazardous material risks or remediation requirements are detected and can be addressed in this process. Details of the Equipment Identification and Evaluation process 111 are described in FIG. 3.

The reFramer™ AI Econometric Evaluation Engine 120 is a combination of AI models, automations, and steps used by the UME Gateway to continuously evaluate available medical equipment inventory and recommend details for how it should be processed at any given point in time. The reFramer™ AI Econometric Evaluation Engine 120 is also referred to as the reFramer™, which is short for Repurpose Econometrics For Rapidly Analyzing Medical Equipment Reuse. The reFramer™ AI Econometric Evaluation Engine 120 allows the UME Gateway to consider current market conditions, specific compliance requirements of healthcare systems and/or asset owners, the uniqueness of specific device types, states, and combinations of different medical devices, and several other factors in near real-time to automatically determine the optimal level of processing on or recommended escape path and associated execution details for the disposition of medical devices. Additional details regarding the functionality of the reFramer™ AI Econometric Evaluation Engine 120 are described in FIGS. 2a and 2b.

The Dynamic Escape Path Dependent AI Processing group 130 integrates with the Dynamic AI Process Orchestration and Monitoring Engine 101 to define and automate the end-to-end process execution steps for each of the eight disposition escape paths for each medical device processed by the UME Gateway. These eight escape paths include the Store path 131, the Redeploy path 132, the Recondition path 133, the Parts Harvest path 134, the Direct Resale path 135, the Merchandised Resale Path 136, the Donate path 137, and the Remediate or Recycle path 138. The Dynamic Escape Path Dependent AI Processing group 130 provides configurations and instructions to automatically generate necessary transactions, work orders, work instructions, queues, and other content and data to allow the UME Gateway Dynamic AI Process Orchestration and Monitoring Engine 101 to automatically execute the escape path decision for each medical device. The three major variants for process execution by the Dynamic Escape Path Dependent AI Processing group 130 are the Non-Resale Escape Path Processing engine 142, the Integrated Recondition and Parts Harvest Supply Chains processing engine 144, and the Multi-Channel Optimization resale processing engine 146.

The first path included in the Dynamic Escape Path Dependent AI Processing group 130 is the Store path 131. In this path, the UME Gateway has determined that certain medical equipment it received from at least one healthcare system and/or asset owner location may still be valuable to that healthcare system's and/or asset owner's organization at some point in the future. Because medical equipment can be very expensive to repurchase the UME Gateway will hold these devices until either the location releasing it or another location or department within the healthcare system's and/or asset owner's facilities can use it effectively, or a final decision to dispose of the medical equipment is eventually made. Medical equipment that proceeds down this path receives a recommendation from the UME Gateway to be transferred to at least one storage facility controlled by the UME Gateway.

The second path included in the Dynamic Escape Path Dependent AI Processing group 130 is the Redeploy path 132. Still available medical equipment that proceeds down this path has either been recalled from the UME Gateway by the facility and department that initially released it due to a mistake or unforeseen need arising or is actively promoted by the UME Gateway to other facilities and departments within a healthcare system and/or asset owner organization that may wish to claim the equipment for itself prior to it being assigned to another disposition escape path. By facilitating redeployments and cross location and department medical device claims the UME Gateway ensures valuable medical devices are not disposed of by healthcare systems and/or asset owners even when the current facility controlling the device decides it no longer needs it. The healthcare system and/or asset owners set the business rules and timelines for how long and to which other facilities and departments redeployments can take place prior to the equipment automatically moving into another escape path.

The third path included in the Dynamic Escape Path Dependent AI Processing group 130 is the Recondition path 133. Medical equipment that proceeds down this path receives a recommendation from the UME Gateway to be reconditioned back to patient-ready specifications and either returned to service within the healthcare system's and/or asset owner's system or subsequently sold to another healthcare system or third-party entity. In this step, the UME Gateway has determined that the medical equipment in its current form is not usable, but the most economically viable and beneficial path is to invest in applying parts, labor, and testing to perform reconditioning, refurbishments, or repairs to make the medical equipment in question usable with patients again. The UME Gateway then manages all activities, work orders, processes and third-party services associated with the reconditioning escape path processing and subsequent reuse or resale of the reconditioned devices.

The fourth path included in the Dynamic Escape Path Dependent AI Processing group 130 is the Parts Harvest path 134. Medical equipment that proceeds down this path when the UME Gateway has determined the most economically viable and beneficial path for that medical equipment is to invest in labor to harvest usable and valuable parts from the device for reuse by the healthcare system and/or asset owner or sold to other healthcare systems or other third-party entities. The harvested parts may themselves be tested and reconditioned at an additional cost prior to being catalogued for later sale to another healthcare system or third-party entity or for later use within the healthcare system's and/or asset owner's own system. The UME Gateway then manages all activities, work orders, processes and third-party services associated with the parts harvesting escape path processing and subsequent reuse, reconditioning or resale of the harvested parts.

The fifth path included in the Dynamic Escape Path Dependent AI Processing group 130 is the Direct Resale path 135. Medical equipment that proceeds down this path receives a recommendation from the UME Gateway to be listed for sale as-is, with no additional investments, on one or more sales channel mediums providing maximum exposure for the equipment to find productive use elsewhere. The UME Gateway then manages all channel listings, offers, sales, and fulfillments that take place in this escape path.

The sixth path included in the Dynamic Escape Path Dependent AI Processing group 130 is the Merchandised Resale path 136. Medical equipment that proceeds down this path receives a recommendation from the UME Gateway to receive value added investments in lotting or kitting the equipment with other assets, performing more testing on the equipment, and/or generating higher quality photos and descriptions of the assets prior to being listed for sale on one or more sales channel mediums providing maximum exposure for the merchandised equipment to find productive use elsewhere. The UME Gateway then manages all channel listings, offers, sales, and fulfillments that take place in this escape path.

The seventh path included in the Dynamic Escape Path Dependent AI Processing group 130 is the Donate path 137. Medical equipment that proceeds down this path receives a recommendation from the UME Gateway to be donated to another healthcare system or a charitable nonprofit organization which does not necessarily have the means to otherwise obtain the medical equipment in question on their own. In this step, the UME Gateway determines that there is no or minimal economic benefit to processing the medical equipment through any of the reselling or reuse escape path options, but the equipment is still usable in its current form and would be better placed into productive use somewhere to improve quality and access to healthcare instead of being recycled or destroyed.

The eighth and final path included in the Dynamic Escape Path Dependent AI Processing group 130 is the Remediate or Recycle path 138. Medical equipment that proceeds down this path receives a recommendation from the UME Gateway to either remediate or recycle the medical equipment in question. Remediation is the process of removing ePHI or hazardous or other environmentally sensitive materials or waste from the medical equipment in question to make it safe for resale or other disposition options. If remediation is not possible or applicable, and if there are no other economically viable options, the UME Gateway will recommend that the medical equipment in question be responsibly destroyed and recycled. The recycling option is for medical equipment that has reached the end of its life, is beyond economic repair, and is void of any economically viable harvestable parts or components and would offer no useful benefits to even a donation recipient receiving the item for free.

The first major variant for process execution by the Dynamic Escape Path Dependent AI Processing group 130 is the Non-Resale Escape Path Processing engine 142 which is an AI assisted process automation that applies to medical equipment assigned to the Store path 131, the Redeploy path 132, the Donate path 137, or the Remediate or Recycle path 138. For medical equipment assigned to the Store path 131 the UME Gateway logs the exact facility and storage bay where a given piece of medical equipment is stored and sends periodic reminders to the healthcare system and/or asset owner reminding them that the medical equipment is being temporarily stored on their behalf and instructions are expected on whether to reclaim or move that medical equipment to another escape path. Added features of the UME Gateway include the ability to perform legally required preventive maintenance activities while items are being stored and to generate all the necessary compliance documentation for a healthcare system's CMMS so there are no obstacles to quickly reclaiming and reusing a device. For medical equipment assigned to the Redeploy path 132, the UME Gateway manages the entire process for pulling, securing, packing, and delivering redeployed medical equipment to its destination when a redeployment occurs. For equipment assigned to the Donate path 137, the UME Gateway manages the tracking of the donations, receipt of donation letter from recipients, and communication of donation records to the providing healthcare system or asset owner. For medical equipment assigned to the Remediate or Recycle path 138, the UME Gateway creates and manages all work order processes associated with the remediation and recycling activities and automatically generates and communicates any applicable certificates of recycling, disposal, and/or destruction for the healthcare system or asset owner that provided the equipment.

The second major variant for process execution by the Dynamic Escape Path Dependent AI Processing group 130 is the Integrated Recondition and Parts Harvest Supply Chains processing engine 144. Medical equipment assigned by the UME Gateway to the Recondition path 133 or the Parts Harvest path 134 is automatically managed through a series of activities that result in a reconditioning or parts harvesting trading partner converting the medical equipment to patient-ready status or parts for subsequent resale or redeployment. All system integrations, activities, investments, tracking of the original and converted inventory, and financial arrangements and settlements are controlled by UME Gateway automations. The Integrated Recondition and Parts Harvest Supply Chains processing engine 144 moves the UME Gateway beyond standard transactions to enable a "barter economy" where reconditioned devices and parts can be acquired by the UME Gateway and its participants in exchange for as-is disposition assets, and when combined with the UME Gateway's Active Registered Demand Module 150 capabilities, can allow reconditioners and parts harvesters, which are typically relatively small, capital constrained organizations, to access and process significantly more devices than would have otherwise been possible. This strengthens the entire medical equipment supply chain allowing far more equipment to be converted into working systems and parts in much shorter timeframes and at lower costs. Details of the Integrated Recondition and Parts Harvest Supply Chains processing engine 144 are described in FIGS. 7a and 7b.

The third and final major variant for process execution by the Dynamic Escape Path Dependent AI Processing group 130 is the Multi-Channel Optimization resale processing engine 146. Medical equipment assigned by the UME Gateway to the Direct Resale path 135 or Merchandised Resale path 136 is automatically and continuously managed through a series of activities that capture the photos and data needed to best market the equipment, list the equipment in one or more UME Gateway controlled and/or third-party medical and industrial equipment resale channels for maximum exposure, and promote that equipment and offer financial and pricing incentives directly to buyers. The Multi-Channel Optimization resale processing engine 146 enables each UME Gateway medical device to be efficiently matched to the right potential buyers through the right channels, at the right pricing based on current market conditions, buyer preferences, device types and several other relevant factors. The UME Gateway can simultaneously provide maximum marketplace exposure across multiple relevant channels in a way that meets unique information requirements of buyers, complies with the rules and formats of the various marketplaces, and most importantly minimizes the chances of any unique medical device from being sold more than once. Lastly the dynamic resell channel manager incorporates pricing and predictive analytics to automate device channel rotations or reassignments to other disposition escape paths as necessary to provide healthcare systems and/or asset owners with timely completion of the disposition process for their compliance needs. Details of the Multi-Channel Optimization resale processing engine 146 are described in FIGS. 6a and 6b.

The Active Registered Demand Module 150 is a set of demand registration capabilities and automations that allow buyers of medical equipment to move beyond limitations of shopping from only currently available or near-term supply of medical devices to having ongoing, automated, intelligent access to everchanging UME Gateway inventory. Since the exact timing of availability of specific types and configurations of medical devices is unpredictable and dependent on disposition by healthcare systems and/or asset owners, UME Gateway available inventory is regularly changing. By using the Active Registered Demand Module 150 vendors can record interest in different makes and models of medical devices along with specific features, conditions, accessories, and minimum quantities they require. This registered demand can range from general interest all the way through pre-negotiated purchase commitments and terms. Buyers benefit from the UME Gateway acting as a virtual shopping agent that constantly monitors and matches supply for them. This includes AI assisted combinatorial analysis and intelligent holds of assets from multiple sources to combine necessary quantities of components and accessories to create full systems. Healthcare systems and asset owners can use the Active Registered Demand Module 150 to record their demand for small capital purchases of parts, parts units, patient ready devices, rentals, or other services that can be fulfilled via the UME Gateway. By providing awareness of registered potential demand and purchasing terms, the reFramer™ AI Econometric Evaluation Engine 120 can more intelligently recommend the most economically beneficial escape path for a healthcare system's and/or asset owner's assets as soon as they enter the UME Gateway. Details of the Active Registered Demand Module 150 and processing done to respond to the registered demand are described in FIGS. 5a and 5b.

The Credit Redemption Marketplace 160 is a marketplace that allows healthcare systems and/or asset owners to multiply UME Gateway earned residual credits from their medical equipment through a credits conversion model. These credits can be used to procure UME Gateway negotiated discounts on medical devices, parts, supplies, training, and other services allowing them to essentially participate with other parties in the "barter economy". The Credit Redemption Marketplace 160 significantly streamlines difficult to manage one-off small capital procurement events and medical equipment and service marketplace sourcing from smaller vendors for the healthcare systems and/or asset owners. Details of the processing and automation involved in supporting the Credit Redemption Marketplace 160 are described in FIGS. 8a and 8b.

The Asset Stakeholder Communications capability 170 includes UME Gateway technologies that create alerts, offer self-service data access, provide AI generated analytics and insights, enable configuration updates, and support both programmatic and user-based interfaces for healthcare systems and/or asset owners to monitor and control all their UME Gateway related medical devices, services, activities, and financial transactions. The Asset Stakeholder Communications capability 170 provides healthcare systems and/or asset owners with near real-time visibility to control all assets, services, costs, earnings, and actions associated with their disposition medical devices. Access can be through web and mobile device-based interfaces and, to the extent a healthcare system and/or asset owner is able, notifications can be embedded into their own organization's alerting queues or placed directly into their CMMS or asset management systems. The Asset Stakeholder Communications capability 170 plays a critical role in allowing a healthcare system and/or asset owner to uniquely tailor their disposition process and role-based interaction and access controls to provide full control and security over how their medical equipment and residual earnings will be managed throughout the UME Gateway and by whom. When combined with AI and other analytics and reporting methods these capabilities equip healthcare systems and/or asset owners to receive recommendations for process improvements to reduce disposition costs as well as insights for speeding up or down disposition or capital purchases, increasing internal redeployments, generating better returns from assets, and otherwise improving their overall financial outcomes and capital planning strategies by using the UME Gateway. Details of the Asset Stakeholder Communications capability 170 are provided in FIGS. 8*a* and 8*b*.

The Financial Posting and Reconciliation Engine 180 is a set of UME Gateway automations that track and reconcile all financial transactions and settlements associated with the UME Gateway. The Financial Posting and Reconciliation Engine 180 is responsible for handling even the most complex consignment, bartering, lotting, kitting, recondi-tioning, and parts harvesting financial settlements to ensure accurate financial accounting exists in the UME Gateway and all healthcare systems and/or asset owner ledgers, earnings, and charges are accurate, auditable, and up to date.

The Digitized Business and Contract Rules and Con-straints database 190 is a database of digitized contract terms and other business, compliance, and governance constraints that are automatically applied to every applicable decision and transaction in the UME Gateway. This allows every event to be captured and any custom pricing, discounts, and entitlements associated with a given transaction/decision to be applied while avoiding handling a medical device in a way contrary to the desires of a healthcare system and/or asset owner, external and governmental compliance entities, or the business rules of the UME Gateway itself. This database also tracks entitlement pools and event usage to make sure overall contractual compliance and business governance is occurring and provides healthcare systems and/or asset owners with insights to better understand their actual medical device disposition activity.

The flow of the Overview of Reverse Supply Chain Gateway for Used Medical Equipment (UME Gateway) 100 is described herein. The Equipment Acquisition process 110 is taken to source medical equipment for the UME Gateway. If specific medical devices are needed or valuable for the UME Gateway to acquire as determined by known demand from the Active Registered Demand Module 150 and/or the reFramer™ AI Econometric Evaluation Engine 120 analyt-ics priority can be placed on sourcing those devices. Once equipment becomes available to the UME Gateway the Equipment Identification and Evaluation process 111 is performed with regards to each individual piece of medical equipment to determine the make, model, type, condition, specifications, and accessories of that piece of medical equipment as further described in FIG. 3. Once a piece of equipment made available to the UME Gateway has been identified and baseline information about it has been cap-tured via the Equipment Identification and Evaluation pro-cess 111 it passes that current inventory availability infor-mation to the reFramer™ AI Econometric Evaluation Engine 120 which uses AI to attach cost/benefit valuations to the piece of medical equipment for each potential escape path in light of the information received from the Equipment Identification and Evaluation process 111, known available demand for the piece of medical equipment captured through the Active Registered Demand Module 150, any constraints on what cannot or must be done with the piece of medical equipment existing in the Digitized Business and Contract Rules and Constraints database 190, other UME Gateway available data sources as further described in FIGS. 2*a* and 2*b*, and the range of options available for different escape paths. If information from the Equipment Identifi-cation and Evaluation process 111 is deemed insufficient by the reFramer™ AI Econometric Evaluation Engine 120 to reliably recommend any potentially valuable escape path option, the reFramer™ AI Econometric Evaluation Engine 120 will send a data enrichment request to the Equipment Identification and Evaluation process 111 to provide the requested information. If the reFramer™ AI Econometric Evaluation Engine 120 determines that the piece of medical equipment is still useful to the healthcare system and/or asset owner in its current state, but the healthcare system and/or asset owner currently has no economically viable place within its organization to redeploy the piece of medical equipment, the reFramer™ AI Econometric Evaluation Engine 120 will recommend the Store path 131, and have the UME Gateway store that piece of medical equipment where it can be held and maintained for future use. If the healthcare system and/or asset owner by its own volition or the reFramer™ AI Econometric Evaluation Engine 120 deter-mines that the piece of medical equipment is still useful to the healthcare system and/or asset owner in its current state, and that the healthcare system and/or asset owner currently has an economically viable place within its organization to redeploy the piece of medical equipment, the reFramer™ AI Econometric Evaluation Engine 120 will recommend the UME Gateway take the Redeploy path 132. If the reFramer™ AI Econometric Evaluation Engine 120 deter-mines that the piece of medical equipment is not useful to the healthcare system and/or asset owner in its current state but will either be more useful to them or return them more money if it is repaired or reconditioned or harvested for parts, then the reFramer™ AI Econometric Evaluation Engine 120 will recommend the UME Gateway take the Recondition path 133 or the Parts Harvest path 134 as appropriate. If the reFramer™ AI Econometric Evaluation Engine 120 determines that the piece of medical equipment is not useful to the healthcare system and/or asset owner in its current state and spending time, money and resources to either recondition or harvest parts and accessories from the medical equipment would result in a less profitable outcome than selling the medical equipment as-is, the reFramer™ AI Econometric Evaluation Engine 120 will recommend the Direct Resale path 135. If the reFramer™ AI Econometric Evaluation Engine 120 determines that the piece of medical equipment is not useful to the healthcare system and/or asset owner in its current state and spending time, money and resources to either recondition or harvest parts and acces-sories from the medical equipment would result in a less profitable outcome than selling the medical equipment, and that investing time lotting, kitting, rephotographing and testing the medical equipment is more profitable than selling the medical equipment as-is, the reFramer™ AI Economet-ric Evaluation Engine 120 will recommend the Merchan-dised Resale path 136. If the reFramer™ AI Econometric Evaluation Engine 120 determines that the piece of medical equipment has no viable economic benefit to be reused by the healthcare system and/or asset owner, nor through any form of as-is, merchandised, reconditioning, or parts har-vesting resale, but the device is still useful for providing healthcare benefits to others and there are organizations who want it the reFramer™ AI Econometric Evaluation Engine 120 will recommend the Donate path 137. If reFramer™ AI Econometric Evaluation Engine 120 determines there is no economic benefit from any of the other escape paths and there are no known organizations interested in receiving that particular medical equipment as a donation, then the reFramer™ AI Econometric Evaluation Engine 120 will recommend it be responsibly recycled through the Remedi-ate or Recycle path 138. Likewise if the reFramer™ AI Econometric Evaluation Engine 120 determines based on the nature and type of the medical equipment itself or through evaluation of any discoveries that occurred during the Equipment Identification and Evaluation process 111 that the piece of medical equipment may contain ePHI or hazardous or environmentally sensitive material it will also be sent down the Remediate or Recycle path 138 where it will be remediated to remove the threat of disclosure of ePHI and/or exposure of the hazardous or environmentally sensitive materials prior to either being responsibly recycled or sent to an alternative escape path. If the reFramer™ AI Econometric Evaluation Engine 120 recommends the medical equipment proceed down the Store path 131, the Redeploy path 132, the Donate path 137, or the Remediate or Recycle path 138 that information will be visible to the Dynamic AI Process Orchestration and Monitoring Engine 101 which will integrate with the Non-Resale Escape Path Processing engine 142 and the Digitized Business and Contract Rules and Constraints database 190 and ensure all AI generated transactions, work orders, work instructions, queues, configurations, and other content and data relevant to that medical equipment and escape path are performed in the most efficient and effective manner that complies with contracts, business rules, and other legal and governance requirements, and that any exceptions detected are addressed by AI or human actors. If the reFramer™ AI Econometric Evaluation Engine 120 recommends the medical equipment proceed down the Recondition path 133 or the Parts Harvest path 134 that information will be visible to the Dynamic AI Process Orchestration and Monitoring Engine 101 which will integrate with the Recondition and Parts Harvest Supply Chains processing automations engine 144 and the Digitized Business and Contract Rules and Constraints database 190 to ensure all AI generated transactions, system integrations, activities, investments, original and converted inventory tracking, compliance, and financial reporting that result from a reconditioning or parts harvesting trading partner converting the medical equipment to patient-ready status or parts for subsequent resale or redeployment occur as detailed in FIGS. 7*a* and 7*b* in the most efficient and effective manner that complies with contracts, business rules, and other legal and governance requirements, and that any exceptions detected are addressed by AI or human actors. If the reFramer™ AI Econometric Evaluation Engine 120 recommends the medical equipment proceed down the Direct Resale path 135 or the Merchandised Resale path 136 that information will be visible to the Dynamic AI Process Orchestration and Monitoring Engine 101 which will integrate with the Multi-Channel Optimization resale processing engine 146 and the Digitized Business and Contract Rules and Constraints database 190 to ensure all activities necessary to perform lotting or kitting of equipment as applicable, capture the photos and data needed to best market the equipment, list the equipment in one or more UME Gateway controlled and/or third-party medical and industrial equipment resale channels for maximum exposure, and promote that equipment to offer financial and pricing incentives directly to buyers occur in the most efficient and effective manner that complies with contracts, business rules, and other legal and governance requirements until the equipment is sold or transitioned to another escape path. The reFramer™ AI Econometric Evaluation Engine 120 can also provide demand response plans, channel and pricing plans, and recondition and parts harvest plans to the Dynamic Escape Path Dependent AI Processing group 130 if needed to choose a proper escape path for a piece or pieces of medical equipment. In all cases the Dynamic AI Process Orchestration and Monitoring Engine 101 will ensure all necessary alerts, notices, documentation, and data are created and communicated to stakeholders through the Asset Stakeholder Communications capability 170, and all necessary data is passed to the Financial Posting and Reconciliation Engine 180 to accurately account for all relevant transactions and events. Information about every piece of medical equipment processed by the UME Gateway, regardless of the escape path taken, is dynamically made available to the Asset Stakeholder Communications capability 170. This provides healthcare systems and/or other asset owners with visibility on all activities, status, costs, residual value generated, and redeployments, sales, donations, or recycling details associated with their medical equipment. This information can be accessed via the web, mobile devices, or directly integrated into the alerting, reporting and CMMS systems used by the healthcare system or other asset owners. The Credit Redemption Marketplace 160 is integrated with the Dynamic Escape Path Dependent AI Processing group 130 and Active Registered Demand Module 150 to track the supply and demand respectively in real time. When a successful purchase/acquisition/disposition is made, the Dynamic Escape Path Dependent AI Processing group 130, the Active Registered Demand Module 150, and the Credit Redemption Marketplace 160 send that information to the Financial Posting and Reconciliation Engine 180 to ensure that the financial postings are reconciled to reflect that purchase/acquisition/disposition. The Asset Stakeholder Communications capability 170 are also integrated with the Equipment Acquisition process 110, the Dynamic Escape Path Dependent AI Processing group 130, the Active Registered Demand Module 150, and the Credit Redemption Marketplace 160 which together allows healthcare systems and/or asset owners to see the residual earnings generated from processing equipment through the UME Gateway, all associated costs and charges they have incurred, and to redeem any available funds by procuring curated and approved medical devices, parts, training or medical equipment related services at a discounted price. Any orders placed will be detected and processed by the Dynamic AI Process Orchestration and Monitoring Engine 101 in conjunction with the Recondition and Parts Harvest Supply Chains processing engine 144 or the Multi-Channel Optimization processing engine 146 as applicable for the items ordered, with the resulting documented purchases communicated to the Asset Stakeholder Communications capability 170 and the Financial Posting and Reconciliation Engine 180 to accurately account for the credit redemption purchases.

The Dynamic AI Process Orchestration and Monitoring Engine 101 and the Digitized Business and Contract Rules and Constraints database 190 work together to guide, provide information to, track, and govern the actions of the Equipment Acquisition process 110, the Equipment Identification and Evaluation process 111, the reFramer™ AI Econometric Evaluation Engine 120, the Dynamic Escape Path Dependent AI Processing group 130, the Active Registered Demand Module 150, the Credit Redemption Marketplace 160, the Asset Stakeholder Communications capability 170, and the Financial Posting and Reconciliation Engine 180. The information and processing from the Dynamic AI Process Orchestration and Monitoring Engine 101 and the Digitized Business and Contract Rules and Constraints database 190 are used to ensure that all action taken and processing that occurs within the UME Gateway is in compliance with any relevant contract rules, entitlements and/or constraints to ensure medical equipment is processed according to the specific requirements of each healthcare system and/or asset owner, buyer or trading partner, that the business rules of the UME Gateway and any governmental or third-party compliance requirements are enforced, and that all actions are brought to completion in the most efficient and effective manner by methodically guiding the interactions and steps performed by automated and human actors, and any issues or discrepancies are communicated and tracked through resolution.

Figure 2A:
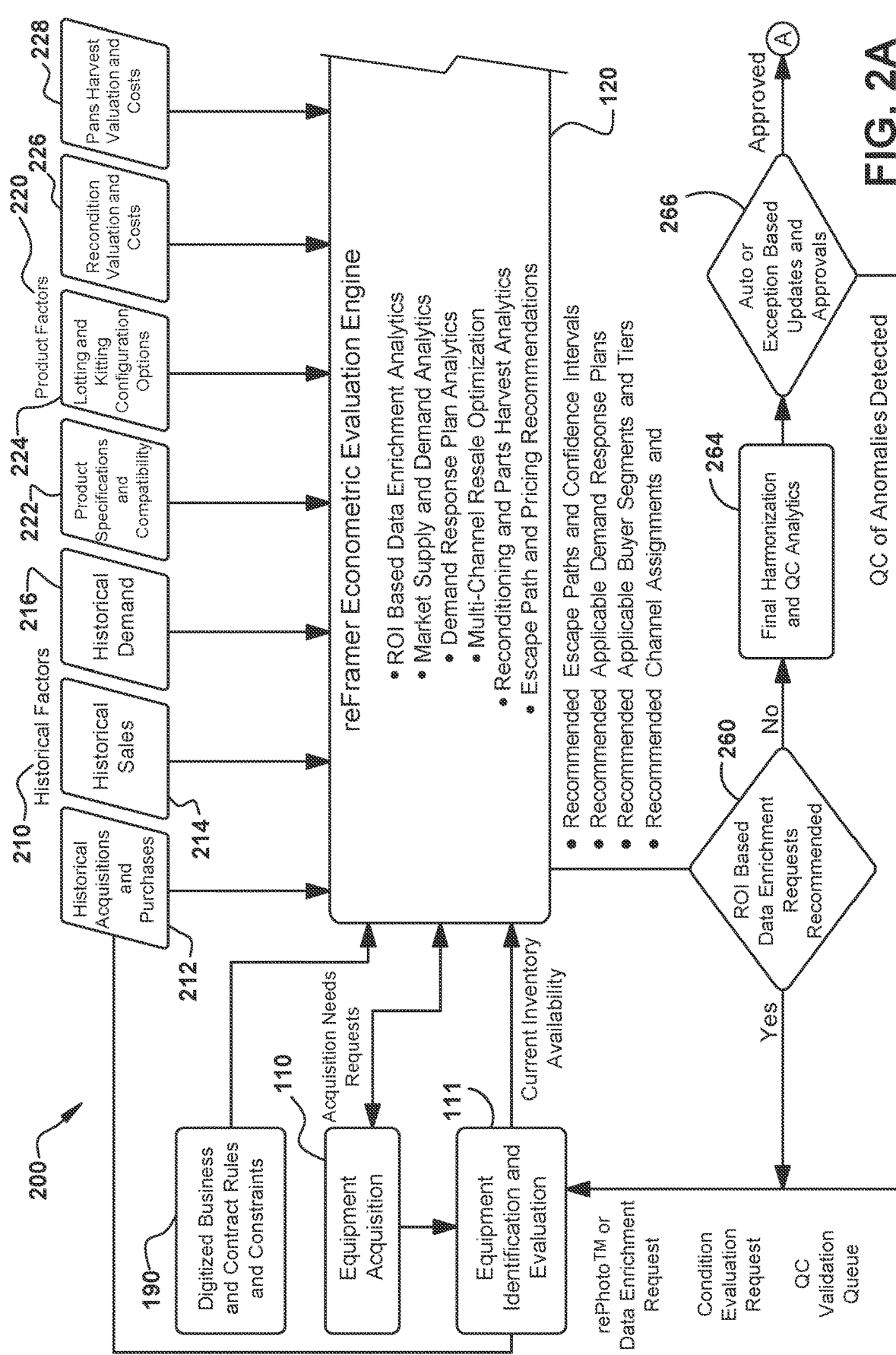
FIGS. 2*a* and 2*b* schematically present a flow chart showcasing the reFramer™ AI Econometric Evaluation Engine in accordance with aspects of the present disclosure.
Figure 2B:
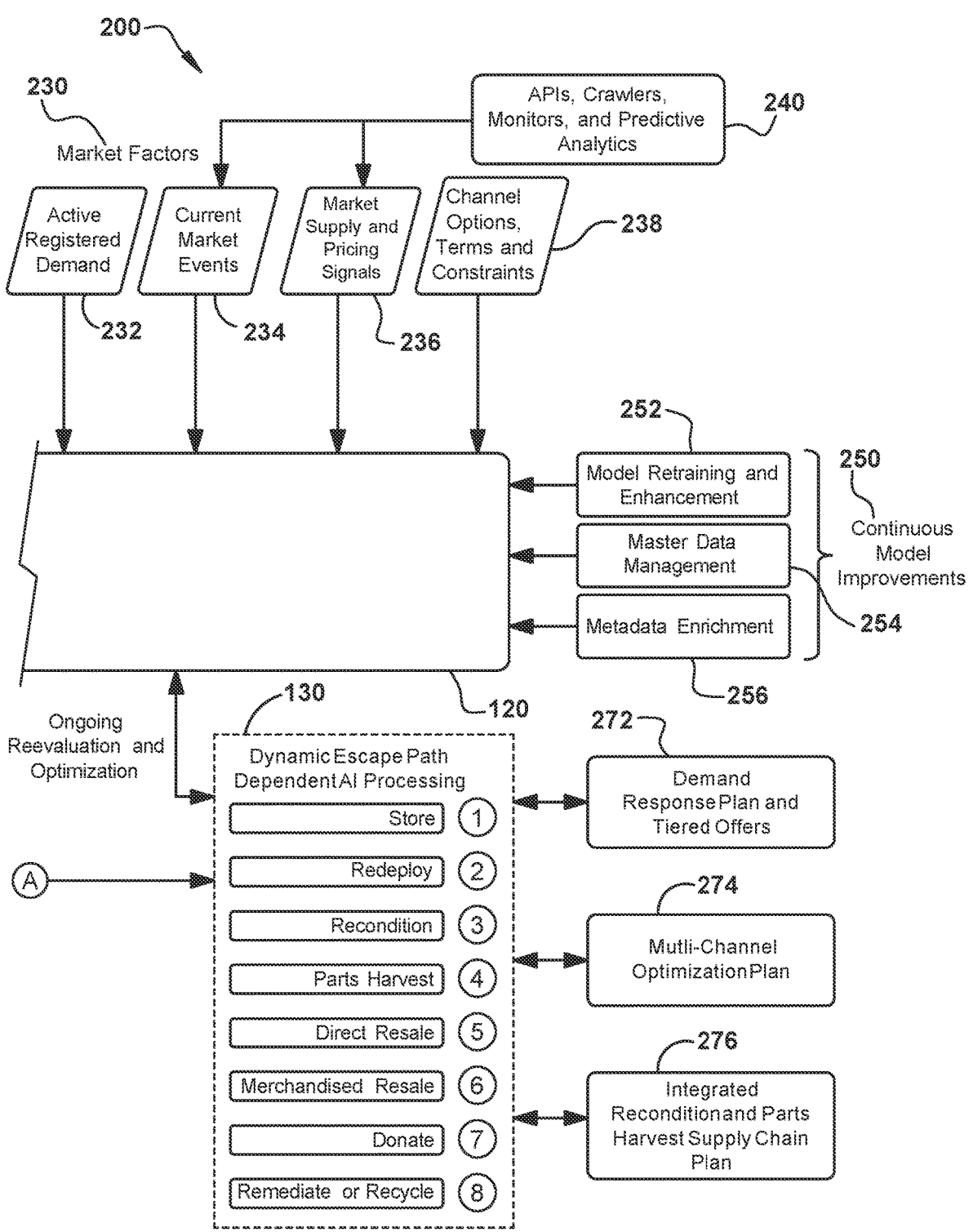

FIGS. 2a and 2b schematically present a reFramer™ AI Econometric Evaluation Engine flowchart 200 showcasing how the reFramer™ Econometric Evaluation Engine 120 from FIG. 1a operates. The reFramer™ Econometric Evaluation Engine Flowchart 200 includes the Digitized Business and Contract Rules and Constraints database 190 which is the same as described in FIG. 1a, the Equipment Acquisition process 110 which is the same as described in FIG. 1a, the Equipment Identification and Evaluation process 111 which is the same as described in FIG. 1a, the reFramer™ AI Econometric Evaluation Engine 120 which is the same as described in FIG. 1a, a Historical Factors group 210, a Product Factors group 220, a Market Factors group 230, an APIs, Crawlers, Monitors and Predictive Analytics engine 240, a Continuous Model Improvements group 250, an ROI Based Data Enrichment Requests Recommended step 260, a Final Harmonization and QC Analytics step 264, an Auto or Exception Based Updates and Approvals step 266, the Dynamic Escape Path Dependent AI Processing group 130 from FIG. 1b, a Demand Response Plan and Tiered Offers output 272, a Multi-Channel Optimization Plan output 274, and an Integrated Recondition and Parts Harvest Supply Chain Plan output 276.

The Historical Factors group 210 includes a Historical Acquisition and Purchases database 212, a Historical Sales database 214, and a Historical Demand database 216. The Product Factors group 220 includes a Product Specifications and Compatibility database 222, a Lotting and Kitting Configuration Options database 224, a Recondition Valuation and Costs database 226, and a Parts Harvest Valuation and Costs database 228. The Market Factors group 230 includes an Active Registered Demand database 232, a Current Market Events database 234, a Market Supply and Pricing Signals database 236, and a Channel Options, Terms and Constraints database 238. The Continuous Model Improvements group 250, which is a group of models that serve to continuously enhance and enrich the data used by the reFramer™ Econometric Evaluation Engine 120, includes a Model Retraining and Enhancement process 252, a Master Data Management process 254, and a Metadata Enrichment process 256.

The Digitized Business and Contract Rules and Constraints database 190 is the same as described as FIG. 1a. It is used by the reFramer™ AI Econometric Evaluation Engine 120 to make sure any contracts, UME Gateway business rules, or third-party legal or government requirements are enforced when determining which escape paths to recommend or whether data enrichment requests are recommended.

The Equipment Acquisition process 110 is the same as described in FIG. 1a and is the process by which medical equipment is made available to the UME Gateway. This process can receive requests from the reFramer™ AI Econometric Evaluation Engine 120 to seek or source specific medical equipment that is in demand or needed for other specific reasons by the UME Gateway when the reFramer™ AI Econometric Evaluation Engine 120 determines such a request is necessary. Additional details about the processes and activities of this step are as described in FIG. 3.

The Equipment Identification and Evaluation process 111 is the same as described in FIG. 1a and is the process by which image processing is combined with AI and other techniques to efficiently identify makes, models, conditions, system completeness, specifications, included accessories, and other basic information about medical equipment to feed into subsequent analysis, databases and automations that can be processed by the UME Gateway. Once the basic information about a piece of medical equipment is known, the information about current available inventory is sent to the reFramer™ AI Econometric Evaluation Engine 120 where it can assess near real-time the financial benefits and compliance requirements to recommend and initiate any best next course of information capture or processing for each unique out of service medical device it determines is worth performing.

The Historical Factors group 210 is a group of databases that assist the reFramer™ AI Econometric Evaluation Engine 120 with evaluating a given piece of medical equipment's likelihood of being able to be resold and in what timeframe, at what price point and though which channels or formats based on past buying and selling activity that has previously taken place within the UME Gateway.

The Historical Acquisition and Purchases database 212 is a database of all medical devices the UME Gateway has ever received either through outright purchases or consignment relationships with healthcare systems and/or asset owners and includes the source of the items and the amounts paid for those devices.

The Historical Sales database 214 is a database of all items the UME Gateway has ever sold including who the buyers were along with the quantities, pricing, discounts, and terms associated with the sale, and the channel or manner the sale was conducted.

The Historical Demand database 216 is a record of past interest from buyers in acquiring products from the UME Gateway regardless of whether this demand resulted in actual transactions. It includes information about the organizations or individuals who had the demand, the products they were interested in at the time, and any proposed details about pricing, terms, and conditions they provided. This information would typically have been previously captured by the Active Registered Demand Module 150 as described in FIG. 1b and as further described in FIG. 5a. While this database's historical demand is no longer current or able to be acted upon it is useful to the AI models in the reFramer™ AI Econometric Evaluation Engine 120 for predicting unknown or future demand.

The Product Factors group 220 is a group of databases that assist the reFramer™ AI Econometric Evaluation Engine 120 in determining when to recommend value added investments be made to medical equipment entering the UME Gateway and/or time should be spent to remediate potential risks and issues associated with that medical equipment.

The Product Specifications and Compatibility database 222 is a database of the device types, specifications and compatible parts and accessories for a piece of medical equipment including the allowable values for the specifications (for example the software version or the existence of an oxygen sensor on a device) and the different manufacturers of compatible parts and accessories. This information assists the reFramer™ AI Econometric Evaluation Engine 120 in ensuring the relevant details it needs about a piece of medical equipment have been captured correctly and, together with information from the Lotting and Kitting Configuration Options database 224, how the reFramer™ might combine different pieces of medical equipment currently available to, or that can be sourced by the UME Gateway into a higher value completed system or lot. The Product Specifications and Compatibility database 222 is also able to alert the UME Gateway whether an item is likely to have risk of containing ePHI or other hazardous materials for the reFramer™ AI Econometric Evaluation Engine 120 to consider in recommending the item be sent to the Remediate or Recycle path 138 in the Dynamic Escape Path Dependent AI Processing group 130.

The Lotting and Kitting Configuration Options database 224 describes the features of a piece of medical equipment and the combination of parts and accessories that are necessary to have a complete, functioning system that can meet a specific medical diagnostic or procedural purpose. It also identifies when similar or related items of a particular device type or manufacturers family make sense to combine for sale as a lot or group where bulk demand exists. Together with the Product Specifications and Compatibility database 222 this information helps the reFramer™ AI Econometric Evaluation Engine 120 identify specific active or available inventory items it recommends combining into a lot or kit for sale to generate a higher return than selling those items individually.

The Recondition Valuation and Costs database 226 is a database of the estimated value of specific refurbished or reconditioned pieces of medical equipment, as well as the estimated costs associated with applying parts and labor for reconditioning specific pieces of medical equipment so that a return on investment calculation can be performed comparing the benefit of reconditioning a UME Gateway held medical device against selling that device as-is.

The Parts Harvest Valuation and Costs database 228 is a database of the estimated value of specific parts that can be harvested from medical equipment contained within the UME Gateway, as well as the estimated costs associated with harvesting those specific parts so that a return on investment calculation can be performed on the benefit of investing in parts harvesting.

The Market Factors group 230 is a group of databases containing information about the current market conditions for a piece of medical equipment that are useful in ascertaining its value and, if there is demand for that piece of medical equipment, the best manner, format, and channels through which to make it available for sale.

The Active Registered Demand database 232 is a database of all the currently registered demand from active buyers for a given medical device, along with any applicable buyers' terms attached to the registered demand. This demand can take the form of interest, quotes, offers and fully pre-negotiated contracts and agreements that can be acted upon. This information would be maintained by the Active Registered Demand Module 150 as described in FIG. 1*b* and as further described in FIG. 5*a*.

The Current Market Events database 234 is a database capturing unusual conditions that could materially impact the supply or demand of a particular device type or make and model. It tracks information such as recalls, supply chain disruptions impacting replacement devices, parts or accessories, epidemiological events and seasons in a country or region that drive a surge in device demand for healthcare providers to respond, new product and technology innovations that obsolete existing medical devices, and other events that impact supply and demand for medical equipment.

The Market Supply and Pricing Signals database 236 is a database of product listings, availability, and actual sales transactions for medical equipment conducted by non-UME Gateway vendors and/or in channels which the UME Gateway does not participate.

The Channel Options, Terms and Constraints database 238 is a database of all channels which the UME Gateway participates in, the types of products typically sold in that channel, any specific types of products that are prohibited by that channel, the buyer segments and geographic areas the channel reaches, the payment and fulfillment methods the channel supports, the costs and fees associated with listing, selling and fulfilling orders in that channel, and other information that can assist the reFramer™ AI Econometric Evaluation Engine 120 in deciding whether to place a piece of medical equipment in a given channel and at what price point to account for the channel's selling and fulfillment terms.

The APIs, Crawlers, Monitors and Predictive Analytics engine 240 is a set of automations and AI assisted processing capabilities that can continuously seek out and capture market events, supply levels, and pricing information. Data points captured are dynamically harmonized and converted into formats useful to the reFramer™ AI Econometric Evaluation Engine 120 to consider the most up to date market conditions impacting the medical equipment reverse supply chain.

The Continuous Model Improvements group 250 is a group of data and analytics-based processes that serve to continuously self-improve the AI capabilities of the reFramer™ Econometric Evaluation Engine 120.

The Model Retraining and Enhancement process 252 is a continuous process running within the reFramer™ AI Econometric Evaluation Engine 120 in which the models used for training the AI within the reFramer™ AI Econometric Evaluation Engine 120 and used for decision-making by the reFramer™ AI Econometric Evaluation Engine 120 are continuously improved through the use of new incoming data and evaluation of the models recommendations against that new data.

The Master Data Management process 254 is a continuous process running within the reFramer™ AI Econometric Evaluation Engine 120 that monitors, enriches, and controls all of the master data related to healthcare systems, asset owners, buyers, vendors, channels, products, and configurations within the reFramer™ AI Econometric Evaluation Engine 120 allowing comparisons to be identified by the AI assisted processing engines.

The Metadata Enrichment process 256 is a continuous process running within the reFramer™ AI Econometric Evaluation Engine 120 that monitors, enriches, and controls all of the metadata within the reFramer™ AI Econometric Evaluation Engine 120 using AI supported recommendations and estimates to fill in any gaps needed to improve models and analytics.

The ROI Based Data Enrichment Requests Recommended step 260 is a step in which the AI interprets the information from the reFramer™ AI Econometric Evaluation Engine 120 to determine whether the return on investment (ROI) would be positive with regards to augmenting or enriching the information presented to the reFramer™ AI Econometric Evaluation Engine 120. If the reFramer™ AI Econometric Evaluation Engine 120 determines more information about a medical device is needed to make better decisions, data enrichment requests can be generated to authorize the time and expense of further information capture from another pass through the Equipment Identification and Evaluation process 111. These additional passes might include capturing more specifications, rephotographing the device, performing more extensive testing and assessments, researching serial numbers and repair histories, or any number of other steps to gather data deemed valuable for the UME Gateway.

The Final Harmonization and QC Analytics step 264 is triggered when the reFramer™ AI Econometric Evaluation Engine 120 determines it has the information it needs to recommend an escape path for a piece of medical equipment, and it does not recommend gathering any additional information on that equipment at this time. The reFramer™ AI Econometric Evaluation Engine 120 recommendation along with an AI model calculated confidence interval in the recommendation is sent to the Final Harmonization and QC Analytics step 264 which automatically ensures the outputs of the reFramer™ AI Econometric Evaluation Engine 120 are interpretable and logically consistent with the rest of the UME Gateway, specifically with regards to form and format and consistency with past recommendations and actions. If any issues or irregularities with the provided information are detected in this step they will be passed on to the Auto or Exception Based Updates and Approvals step 266 along with the recommendations and confidence interval.

The Auto or Exception Based Updates and Approvals step 266 is a step which receives the recommendation and AI generated confidence interval from the reFramer™ AI Econometric Evaluation Engine 120 along with any issues detected during the Final Harmonization and QC Analytics step 264 and then determines whether the recommendation should be automatically approved for transmission to the Dynamic Escape Path Dependent AI Processing group 130 or human assisted intervention should take place to approve or change the information before proceeding. The higher the confidence interval the higher the likelihood the AI recommendation will be auto approved. A request to send the medical equipment back to the Equipment Identification and Evaluation step 111 for further data enrichment can also be made to address low confidence intervals or issues and irregularities in the data.

The Demand Response Plan and Tiered Offers output 272 is an output that can be produced by the reFramer™ AI Econometric Evaluation Engine 120 recommending the order and manner in which the UME Gateway medical equipment inventory should be allocated to or made available to potential buyers to maximize the return generated from that equipment and avoid overpromoting or overselling the equipment. Details of the Demand Response Plan and Tiered Offers output 272 are further described in FIGS. 5a and 5b.

The Multi-Channel Optimization Plan output 274 is an output that can be produced by the reFramer™ AI Econometric Evaluation Engine 120 recommending the channel listing order, timing, pricing, and promotions for a given piece of UME Gateway medical equipment inventory to maximize the return generated from that equipment and avoid overpromoting or overselling the equipment. The Multi-Channel Optimization Plan output 274 is incorporated into the Multi-Channel Optimization resale processing engine 146 in FIGS. 1b and 1s further described in FIGS. 6a and 6b.

The Integrated Recondition and Parts Harvest Supply Chain Plan output 276 is an output that can be produced by the reFramer™ AI Econometric Evaluation Engine 120 recommending the order and manner scarce UME Gateway medical equipment inventory should allocated to or made available to reconditioning or parts harvesting trading partners to maximize the return generated from that equipment and avoid overpromoting or overselling the equipment. The Integrated Recondition and Parts Harvest Supply Chain Plan output 276 is incorporated into Integrated Recondition and Parts Harvest Supply Chains processing engine 144 in FIGS. 1b and 1s further described in FIGS. 7a and 7b.

The flow of the reFramer™ AI Econometric Evaluation Engine flowchart 200 is described herein. When a piece of medical equipment has been identified and made available as current inventory to the UME Gateway via the Equipment Identification and Evaluation step 111 the reFramer™ AI Econometric Evaluation Engine 120 will perform an AI based multi-dimensional assessment to compare the profitability of pursuing different viable escape paths for the equipment. Information about the medical equipment from the Equipment Identification and Evaluation step 111 is evaluated against models that incorporate data from the Historical Acquisition and Purchases database 212, the Historical Sales database 214, the Historical Demand database 216, the Product Specifications and Compatibility database 222, the Lotting and Kitting Configuration Options database 224, the Recondition Valuation and Costs database 226, the Parts Harvest Valuation and Costs database 228, the Active Registered Demand database 232, the Current Market Events database 234, the Market Supply and Pricing Signals database 236, and the Channel Options, Terms and Constraints database 238. The Current Market Events database 234 and the Market Supply and Pricing Signals database 236 continuously receive information regarding current market conditions from the APIs, Crawlers, Monitors and Predictive Analytics engine 240, keeping the Current Market Events database 234 and the Market Supply and Pricing Signals database 236 up to date on current market events, market supply, and pricing signals. The Digitized Business and Contract Rules and Constraints database 190 is also incorporated to enforce or eliminate any escape path options as dictated by the healthcare system or other asset owner that provided the medical equipment to the UME Gateway, or due to other business or third-party compliance and governance requirements that apply to the medical equipment. The reFramer™ AI Econometric Evaluation Engine 120 outputs its escape path, and if relevant, pricing recommendations for the medical equipment along with a confidence interval it has in the recommendations. The confidence interval is based on factors that include the quantity, quality, recency, and degree of fit of the data used, past accuracy of previous AI based recommendations, and known risk factors associated with the type of medical equipment and its perceived value. Depending on the recommended escape path chosen, the reFramer™ AI Econometric Evaluation Engine 120 may also generate a Demand Response Plan and Tiered Offers 272 output, a Multi-Channel Optimization Plan output 274, or an Integrated Recondition and Parts Harvest Supply Chain Plan output 276 as applicable for a piece of medical equipment, via the Dynamic Escape Path Dependent AI Processing group 130. If the reFramer™ AI Econometric Evaluation Engine 120 determines that additional medical equipment is needed to meet demand, the reFramer™ AI Econometric Evaluation Engine 120 will send an acquisition needs request to the Equipment Acquisition process 110 to fulfil that need. The reFramer™ AI Econometric Evaluation Engine 120 outputs pass through a series of checks for the UME Gateway to make a final decision regarding which escape path the medical device will follow. First the ROI Based Data Enrichment Requests Recommended step 260 is performed when the reFramer™ AI Econometric Evaluation Engine 120 determines if it is worth the investment of time and resources to gather additional information about the medical equipment's condition, specifications, and accessories prior to making a recommendation. If so the Equipment Identification and Evaluation step 111 process is repeated, and the medical device is reevaluated in light of the new information. If additional information gathering is not needed the reFramer™ AI Econometric Evaluation Engine 120 passes its recommended escape path and AI computed confidence intervals in the recommendations to the Final Harmonization and QC Analytics step 264 for data validation, quality control, and ensuring the information is in a structured and logical format consistent with the rest of the UME Gateway suitable for continued automated processing. This step also determines if the AI recommended escape path and proposed pricing confidence intervals are within tolerance levels to automatically move to execution of the escape path and that there are no other identified issues or irregularities in the reFramer™ AI Econometric Evaluation Engine 120 outputs that should be investigated. If issues or irregularities are discovered, human assisted support can take place in the Auto or Exception Based Updates and Approvals step 266 to confirm or change the recommendations. In this step any new unique market conditions known generally but not yet input into the supporting databases or AI models such as recalls, epidemiological events, supply chain disruptions and other factors that impact the healthcare industry as well as new information known about certain types, makes and models of medical equipment can be considered in making a final decision. Once this step is complete instructions about the medical equipment including any applicable Demand Response Plan and Tiered Offers 272 output, Multi-Channel Optimization Plan output 274, or Integrated Recondition and Parts Harvest Supply Chain Plan output 276, can be passed to the Dynamic Escape Path Dependent AI Processing group 130 to proceed through the selected escape path processing. In the event the AI models were unable to make a recommendation with any degree of confidence, issues or irregularities were discovered, and/or human assisted evaluations determine an escape path decision cannot be reliably made for the medical equipment without more information gathering, this step can also return the medical equipment to the Equipment Identification and Evaluation step 111 to gather information needed for a subsequent pass through the process. The Model Retraining and Enhancement process 252, the Master Data Management process 254, and the Metadata Enrichment process 256 continuously work in parallel to improve the models used by the AI within the reFramer™ AI Econometric Evaluation Engine 120. They work by improving the quantity and quality of data available to the models as well as provide feedback to the models on the quality of its previous recommendations and what choices ideally would have been made for the known inputs based on actual results.

The UME Gateway relies on the reFramer™ Econometric Evaluation Engine 120 to recommend if and how much investment to make in identifying additional details about an asset, as well as the ideal disposition escape path and, if relevant, the pricing for each medical device based on the information available. In addition to manufacturer and model, the reFramer™ AI Econometric Evaluation Engine 120 considers any available information about the available quantity, condition, specifications, and included accessories of medical equipment in the UME Gateway as these factors can uniquely drive value of a device.

Actual transactional and demand history including past UME Gateway purchases, sales, donation, and recycling events for similar medical equipment are considered by the reFramer™ AI Econometric Evaluation Engine 120 as are historical quotes and offers to buy and sell similar medical equipment that illustrate past valuation and supply and demand conditions even where no transaction occurred. Each of these can help the AI models evaluate the success rate of previous escape paths and price point assignments when making a recommendation on currently available medical equipment. The specific terms, channels, seasonality, timing, and other unique order details such as additional items included that relate to these data sets are also considered by the AI models in weighting and normalizing the information for econometric evaluations for recommending escape paths and pricing at the current time.

Other differentiated inputs to the reFramer™ AI Econometric Evaluation Engine 120 include product data to assess the cost versus benefit of making value added investments of labor, logistics, parts, and accessories into medical devices to merchandise and describe them better, improve their conditions, or transform the devices into complete systems, lots, or harvested parts. Some items such as ultrasound machines, surgical tools, or patient monitors see significant gains in value when available in known working conditions and as compete systems or sets with all relevant items and modules included. The UME Gateway can continuously assess and predict the value of performing more testing and information gathering on a medical device to improve the device's merchandising and provide better information and assurance to potential buyers. Likewise, the UME Gateway can evaluate the feasibility of making higher value combinations of complete systems and sets by analyzing available assets and predicting supply across multiple healthcare systems, asset owners, and UME Gateway locations. By evaluating the potential for creating lotting and kitting combinations of compatible items a return-on-investment value can be computed by the reFramer™ AI Econometric Evaluation Engine 120 against dispositioning the items as is or with only increased merchandising information. In a like manner the return-on-investment from reconditioning a device to patient-ready status or of harvesting and selling device parts can be evaluated against the as-is and merchandised reselling possibilities. This helps the reFramer™ AI Econometric Evaluation Engine 120 to make the most profitable recommendation on disposition escape path for the healthcare system or asset owner while providing medical equipment reverse supply chain vendors with the products, formats, conditions, and information needed to make more informed buying decisions.

In addition to historical events and product information, the reFramer™ AI Econometric Evaluation Engine 120 considers as much information about current market conditions when making the AI based recommendations on how currently available medical equipment should optimally be processed. All active registered demand, quotes, interest, negotiations, and purchase commitments are incorporated into the econometric modeling providing indication of the immediate possibilities to sell or donate currently available for UME Gateway medical equipment. This data provides the reFramer™ AI Econometric Evaluation Engine 120 insight for recommending listing price points, the anticipated result of negotiations, and potential guidance where pricing, quotes and offers may have been set too high or too low in the past. This demand data uniquely incorporates any known fulfillment terms which can add or subtract value from a transaction's profitability depending on location of the buyer, delivery or pickup timing, responsibility for packing and shipping, and payment method used. Considering the ultimate post fulfillment profitability of a device helps the reFramer™ AI Econometric Evaluation Engine 120 provide more accurate product valuation recommendations based on value instead of simply price. As with actual historical transactions any active registered demand will have its terms, channels, seasonality, and timing data considered in the econometric evaluations and recommendations performed by the reFramer™ AI Econometric Evaluation Engine 120.

The reFramer™ AI Econometric Evaluation Engine 120 is also able to uniquely and cost effectively factor in third-party market information from non-UME Gateway controlled data sources including information about current market conditions related to specific makes, models or types of devices, healthcare conditions in specific countries or regions, and current supply and pricing conditions. This information allows the UME Gateway AI models to predict and incorporate where the medical equipment reverse supply chain needs, opportunities and risks stand at the time medical equipment enters the UME Gateway. The UME gateway incorporates external market information in a cost-effective way by automating its collection with a series of APIs, crawlers, and monitors and then applying AI to automatically harmonize that information into a taxonomy used by the UME Gateway and generating predictive analytics to anticipate the direction of market trends and changes. This allows the reFramer™ Econometric Evaluation Engine 120 to consider information such as the predicted availability of medical device supply, manufacturer recalls, manufacturer supply chain disruptions, epidemiological predictions about known disease seasons and spread in national or international markets or regions, end of life support for popular models, and introductions of new medical device technology or regulations that enhance or obsolete existing devices. Each of these factors can cause pricing for related aftermarket medical equipment to skyrocket or plummet in very short timeframes and is important to detect and include in the models used by the reFramer™ AI Econometric Evaluation Engine 120. Similarly, there is often a period where older medical equipment becomes so scarce it can see sudden rapid pricing increases after many months or years of downward trends because global healthcare providers need to keep fleets alive or secure parts. Early detection of these types of changes by the reFramer™ AI Econometric Evaluation Engine 120 can yield significant economic benefit.

Regardless of economic assessments, any UME Gateway contractual commitments to healthcare systems and/or asset owners regarding timing, allowable or required escape paths, ability to combine devices with those from other sources, and other constraints will be enforced first in making the recommendations. These may result in overinvestment in assessing and processing devices to reduce risk to the healthcare system and/or asset owner or limiting disposition escape path alternatives. By allowing healthcare systems and/or asset owners to dynamically control these factors they can ensure their disposition process complies with their unique governance requirements. Similarly, any UME Gateway internal or third-party governance or legal constraints or requirements related to a specific type or source of medical equipment are factored in by the reFramer™ AI Econometric Evaluation Engine 120 where they dictate or change the escape path recommendations.

In addition to outputting recommended valuations and disposition paths the reFramer™ AI Econometric Evaluation Engine 120 evaluates the input data it uses and provides confidence scores for its recommendations. Each record has its own independent score as to confidence and quality of the data the AI models determine based on when, where, and how the information used was collected and whether it relied on firm completed transactions and demand with standard terms or something more interpreted and less typical. The more pricing and cost data points that exist, the more recent they are, the higher their individual confidence scores, and the closeness in fit to the asset in question, the more likely the model can make recommendations with high confidence. Where confidence is low intervention can take place to provide more data inputs or confirm or override any recommendations prior to execution.

AI models make the contribution made by the reFramer™ AI Econometric Evaluation Engine 120 to the UME Gateway economically feasible and differentiated in several ways. First, the models can identify gaps in data, metadata, and master data and automatically fill them in or generate alerts to put intervention where most needed. This overcomes the previously costly and time-consuming barrier of requiring well cleansed and audited data sets for traditional calculation methods to work. Similarly, AI can perform prework in sourcing relevant market data and either process it into a consumable format or present it to users who need to perform only very specific well directed actions to make the data usable. This vastly increases the amount of data input into the model because even if AI cannot fully process and accurately interpret information it can efficiently guide people to do so to augment the econometric data points where the AI can take over. Finally, AI can quickly computationally normalize data across a variety of factors to determine ultimate potential pocket margin returns from different medical equipment escape path alternatives along with assess confidence in the recommendations.

The calculation models of the reFramer™ AI Econometric Evaluation Engine 120 work to meet unique requirements specific to medical devices. Each device is unique in terms of condition, specifications, accessories, sourcing, repair and usage history, compatibility, and other variables. By defining and normalizing baseline equipment definitions any number of weighted adjustments and range interpolations can be used to move price and costs up or down based on actual known variables about the device. Historical transactions, registered demand, and market inputs can be deconstructed into the standardized definitions using the above method in reverse. By normalizing pricing and costs, even unlike devices can be easily compared and value assessed. Composite scoring can be applied to compare identical makes and models, similar makes and models in the same family, and different devices across entire device categories. Confidence intervals are determined based on the degree of exact matching and the number and recency of data points and adjustments applied. When fewer data points exist, data is older, and more assumptions and interpolations are made there is less confidence in the outcome which can trigger review or intervention.

Because of high pricing volatility, sporadic volumes, and relatively fewer demand centers for aftermarket medical equipment ongoing updates to the data and models used by the reFramer™ AI Econometric Evaluation Engine 120 help deliver better and more current value assessments for each medical device to avoid the economic ramifications of overinvesting in an asset or selling it well below its true potential market value.

AI model retraining within the reFramer™ AI Econometric Evaluation Engine 120 occurs through a combination of supervised and semi-supervised learning. Trained human operators with medical device knowledge provide direct training inputs, review AI provided values, and adjust as needed. Tracking the percentage of time intervention or changes are needed identifies whether the model is converging and allows specialists to intervene to enhance poorly performing models. This helps with confidently sourcing and processing unstructured marketplace data which has far more variability. By decoupling the AI models from the UME Gateway rapid changes in technology, learnings, improved data sets, and market insights can be incorporated or used to replace existing components.

In summary, the reFramer™ AI Econometric Evaluation Engine 120 replaces highly limited and very expensive data gathering tasks and human "gut feel" decision making about a relatively complex set of alternatives for deciding the right level of investment to make in understanding or improving a medical device and setting a disposition path based on rapidly changing time-sensitive market conditions. Humans can continue to support, guide, teach and intervene with the results generated by the reFramer™ AI Econometric Evaluation Engine 120 as needed while eliminating many of the error prone data sourcing and metadata completion tasks that were traditionally required.

Figure 3:
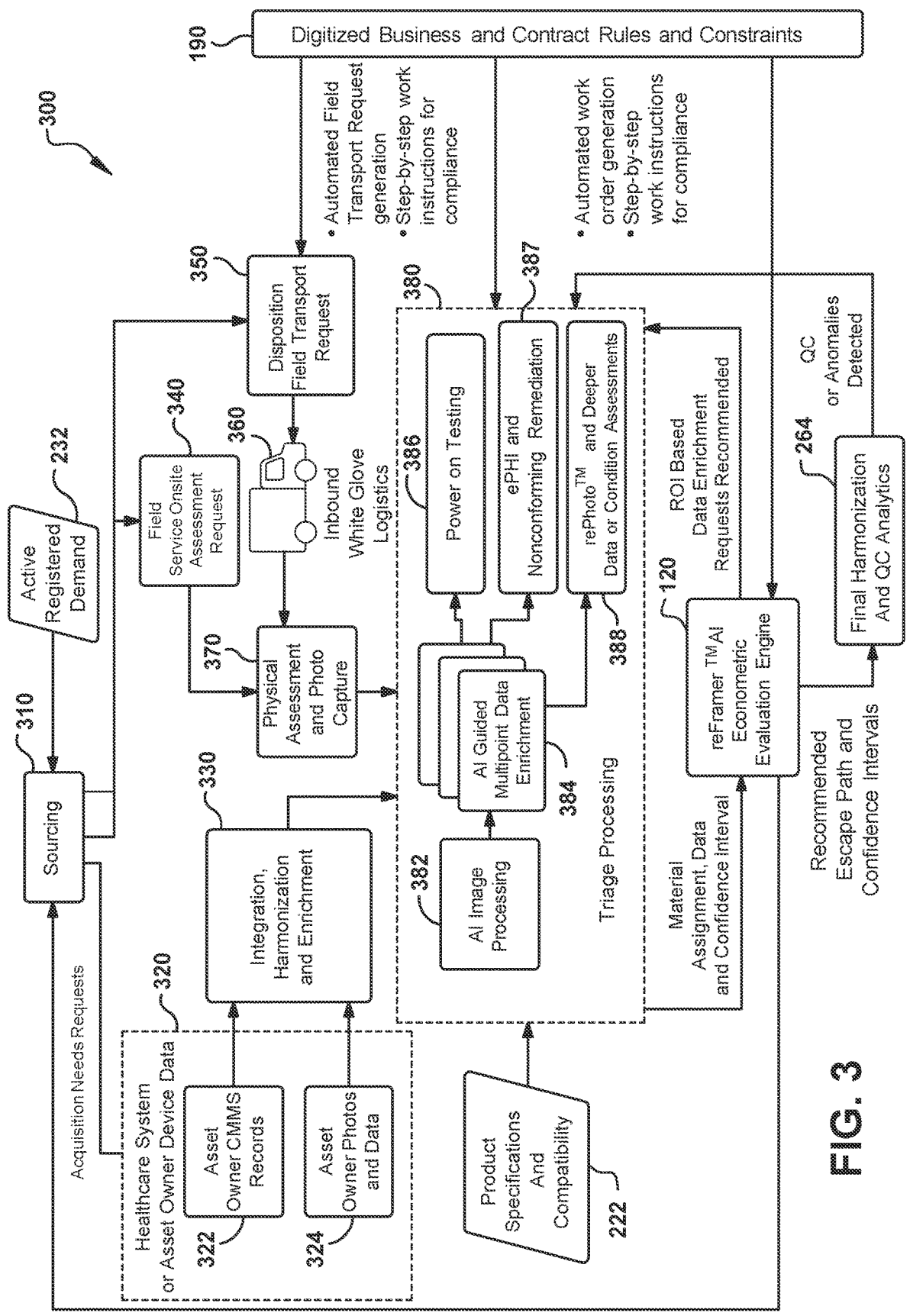
FIG. 3 schematically presents a flow chart showcasing the UME Gateway Optimized Medical Equipment Acquisition, Identification, and Evaluation system in accordance with aspects of the present disclosure.

FIG. 3 schematically presents a UME Gateway Optimized Medical Equipment Acquisition, Identification and Evaluation process flowchart 300, showcasing how the UME Gateway streamlines and optimizes processing to provide a fast initial identification of medical equipment to determine optimal levels of further data gathering or investment in each device to improve returns for healthcare systems and/or asset owners while increasing information available to buyers to lower their risk and make more informed decisions when acquiring medical equipment. The UME Gateway Optimized Medical Equipment Acquisition, Identification and Evaluation process flowchart 300 includes a Sourcing step 310, the Active Registered Demand database 232 which is the same as described in FIG. 2b, a Healthcare System or Asset Owner Device Data group 320, an Integration, Harmonization and Enrichment engine 330, a Field Service Onsite Assessment Request step 340, a Disposition Field Transport Request step 350, an Inbound White Glove Logistics step 360, a Physical Assessment and Photo Capture process 370, the Digitized Business and Contract Rules and Constraints database 190 which is the same as described in FIG. 1a, the Product Specifications and Compatibility database 222 which is the same as described in FIG. 2a, a Triage Processing Group 380, the reFramer™ AI Econometric Evaluation Engine 120 which is the same as described in FIG. 1a, and the Final Harmonization and QC Analytics step 264 which is the same as described in FIG. 2a.

The Healthcare System or Asset Owner Device Data group 320 includes an Asset Owner CMMS Records process 322 and an Asset Owner Photos and Data process 324.

The Triage Processing group 380 includes an AI Image Processing step 382, a set of AI Guided Multipoint Data Enrichment steps 384, a Power On Testing step 386, an ePHI and Nonconforming Remediation step 387, and a rePhoto™ and Deeper Data or Condition Assessments step 388.

The Sourcing step 310 is a set of AI generated automated communications and work queues of activities performed by the UME Gateway to secure medical equipment. Healthcare systems and/or asset owners respond to these communications by providing information about equipment they might assign to the UME Gateway through the Healthcare System or Asset Owner Device Data group 320 submission, a Field Service Onsite Assessment Request 340, and/or a Disposition Field Transport Request 350.

The Active Registered Demand database 232, which is the same as described in FIG. 2b informs the Sourcing step 310 of known demand for medical equipment so the Sourcing step 310 can prioritize generating communications for the more needed equipment.

The Healthcare System or Asset Owner Device Data group 320 is a set of processes by which healthcare systems and/or asset owners submit information about medical equipment they might make available to the UME Gateway if necessary. This might be in the form of CMMS data sets or other forms of data records and images about that medical equipment.

The Asset Owner CMMS Records process 322 is a process by which the UME Gateway automatically integrates with a healthcare system and/or asset owners CMMS system to either pull or receive pushed records of medical equipment which may enter the UME Gateway including makes, models, asset numbers, serial numbers, condition records, maintenance history and other end of life information known by the healthcare system and/or asset owner. This gives the UME Gateway access to information about the medical equipment that can be used throughout the rest of the identification and disposition process.

The Asset Owner Photos and Data process 324 is a process by which Asset owners provide a compilation of semi-structured or unstructured photographs and/or data about medical equipment they may make available to the UME Gateway and the UME Gateway ingests this information to use throughout the rest of the identification and disposition process.

The Integration, Harmonization and Enrichment engine 330 works to integrate a healthcare system's and/or asset owner's system into the UME Gateway's system in such a way that data originating from the healthcare system's and/or asset owner's system is transformed into formats and taxonomies readable and usable by the UME Gateway's system.

The Field Service Onsite Assessment Request step 340 allows healthcare systems and/or asset owners to arrange for the UME Gateway to schedule onsite assessments for a given piece of medical equipment at that healthcare system and/or asset owner's location to gather information necessary to determine how to process that medical equipment.

The Disposition Field Transport Request step 350 allows healthcare systems and/or asset owners to arrange for the UME Gateway to schedule transportation for a given piece of medical equipment from a healthcare system or other asset owner's location to a location controlled by the UME Gateway.

The Inbound White Glove Logistics step 360 is a transportation option usable by the UME Gateway to ensure the safe and sanitary transportation of a given piece of medical equipment to a physical location controlled by the UME Gateway.

The Physical Assessment and Photo Capture process 370 is a process in which human triage staff follows a UME Gateway AI guided process to capture pictures of a piece of medical equipment and to visually assess that piece of medical equipment, looking for and noting in the UME Gateway system any visual damage, missing pieces, or abnormalities, as well capturing identifying characteristics such as healthcare system and/or asset owner tags, serial numbers and part numbers.

The Product Specifications and Compatibility database 222 which is the same as described in FIG. 2a includes data regarding the device types, specifications and compatible parts and accessories for a piece of medical equipment including the allowable values for the specifications (for example the software version or the existence of an oxygen sensor on a device) and the different manufacturers of compatible parts and accessories which is used as input to guide the activities of the Triage Processing group 380.

The Triage Processing group 380 is a series of dynamically orchestrated medical device information capture and handling steps, utilizing both human and AI agents to complete the necessary steps required to safely handle medical equipment and cost-effectively produce the data needed by the UME Gateway to make the optimal escape path decision for that equipment.

The AI Image Processing step 382 is a step in which the AI processes any images gleaned from the Asset Owner Photos and Data process 324 or the Physical Assessment and Photo Capture process 370 to automatically identify the type make, model, accessories and specifications of the medical equipment and validate that the photos and information captured in the previous steps appears complete and accurate for the device type it determined. The AI further assigns a confidence interval to the medical equipment identification related to how confident the AI is that the assigned identification is accurate. Accurate auto assignments make it financially viable to process even low value equipment through the UME Gateway and provide better information to potential buyers so they can make more informed decisions about their interest in a piece of medical equipment. This step also determines if the quality of the photos is suitable for downstream merchandising and presentation back to the healthcare system or other asset owner, and that if any confidential or private information appears present in those photos it is tagged and blocked to avoid public disclosure.

The AI Guided Multipoint Data enrichment steps 384 are a series of steps the UME Gateway follows to determine if it should automatically seek any additional information from within the UME Gateway or instruct human staff to follow a guided process to augment or update the photos or data related to a medical device in order to optimize the downstream escape path decision making and processing and improve the content available for potential buyers. The AI models evaluate the confidence intervals from the AI Image Processing step 382 and compare available information against the Product Specifications and Compatibility database 222 which is an objective source of determining the completeness and consistency of product information. To the extent information is provided by the healthcare system and/or asset owner via processes in the Healthcare System or Asset Owner Device Data group 320 less effort is needed by human staff. These automations make UME Gateway processing viable for even lower value medical equipment increasing the throughput and benefits to all UME Gateway medical equipment reverse supply chain participants. An updated confidence interval related to the information about the medical equipment is assigned by the AI after any of the AI Guided Multipoint Data enrichment steps 384 are performed.

The Power On Testing step 386 is a step in which human triage staff test a given piece of medical equipment to see if it powers on when the power button/switch is engaged as one confirmation of potential working condition of that medical equipment if necessary.

The ePHI and Nonconforming Remediation step 387 is a step in which either human triage staff during the Physical Assessment and Photo Capture process 370 or AI during the AI Image Processing step 382 (or both, depending on the situation) assess whether a piece of medical equipment may have risk of containing ePHI or biohazards of environmentally sensitive materials, and if so checks to see if those issues are present. If detected these issues need to be eliminated in this process prior to moving into a disposition escape path and a Certificate of Destruction or Certificate of Disposal is generated by the UME Gateway to provide the healthcare system or other asset owner confirmation that the remediation took place.

The rePhoto™ and Deeper Data or Condition Assessments step 388 is a step in which the AI or a human actor has determined whether the piece of medical equipment should be rephotographed to provide better merchandising to potential buyers, or if the system needs more information regarding the piece of medical equipment for the reFramer™ AI Econometric Evaluation Engine 120 to make an escape path or pricing recommendation as described in FIGS. 2a and 2b. The system will make these determinations if it needs the information to assign a more accurate monetary value to the piece of medical equipment or to determine an escape path for the piece of medical equipment or to meet contractual commitments it discerns from the Digitized Business Contract Rules and Constraints database 190.

The reFramer™ AI Econometric Evaluation Engine 120 which is the same as described in FIG. 1a uses the output from the Triage Processing group 380 to perform its evaluations and assign recommended escape paths for each medical device. The reFramer™ AI Econometric Evaluation Engine 120 may also determine the return on investment (ROI) would be positive with regards to augmenting or enriching the information about the medical equipment through further processing in the Triage Processing group 380.

The Final Harmonization and QC Analytics step 264 which is the same as described in FIG. 2a is a step that uses AI to evaluate the reFramer™ AI Econometric Evaluation Engine 120 recommendations and confidence intervals along with all other available product data and photos in the UME Gateway to validate the recommendations. This step determines if any issues, inconsistencies, or quality concerns are detected with regards to data form, format, and consistency with past recommendations and actions to merit validating or enriching the information about the medical equipment through further processing in the Triage Processing group 380.

The Digitized Business and Contract Rules and Constraints database 190 is the same as described in FIG. 1a and is incorporated during the Disposition Field Transport Request step 350, during activities conducted by members included in the Triage Processing group 380, and during the reFramer™ AI Econometric Evaluation Engine 120 escape path decision making to ensure all commitments made for any specific or additional information capture, deeper or specific ePHI and nonconforming remediation steps and processes, or other requirements or constraints of a healthcare system and/or asset owner or other governance or regulatory agency are performed efficiently and effectively. Where needed the Digitized Business and Contract Rules and Constraints database 190 will provide information for the UME Gateway to automatically generate work orders and step-by-step instructions for the Inbound White Glove Logistics step 360 and the Triage Processing group 380 to facilitate compliance.

The flow of the UME Optimized Medical Equipment Acquisition, Identification and Evaluation process flowchart 300 is described herein. The Sourcing step 310 communicates with healthcare systems and/or asset owners to identify and secure medical equipment for the UME Gateway. The Sourcing step 310 seeks all types of medical equipment while prioritizing finding the most needed medical devices as identified in the Active Registered Demand database 232 and/or determined by the reFramer™ AI Econometric Evaluation Engine 120. The Sourcing step 310 results in healthcare systems and/or asset owners making equipment available to the UME Gateway through a combination of sending in device data via the Asset Owner CMMS Records process 322 and/or the Asset Owner Photos and Data process 324 in the Healthcare System or Asset Owner Device Data group 320, by initiating a Field Service Onsite Assessment Request 340 for medical equipment to be evaluated at the healthcare system's or asset owner's facilities, and/or requesting a pickup of the devices for transport to a UME Gateway controlled location via a Disposition Field Transport Request 350 which triggers an Inbound White Glove Logistics step 360 to perform the equipment transport. Medical equipment data and photos directly sent in or pulled from a healthcare system or asset owner's CMMS systems or other means (via the Asset Owner CMMS Records process 322 and/or the Asset Owner Photos and Data process 324) goes through an Integration, Harmonization, and Enrichment step 330 to convert the content to the formats and taxonomy needed by the UME Gateway to process the information via the Triage Processing group 380. Medical equipment sourced through a Field Service Onsite Assessment Request 340 will have a UME Gateway representative visit the healthcare system or asset owner facilities to perform an AI guided physical assessment and photograph the equipment via the Physical Assessment and Photo Capture process 370 to get pictures and information about the equipment including any visual damage, missing pieces, or abnormalities, as well capturing identifying characteristics such as healthcare system and/or asset owner tags, serial numbers and part numbers into the UME Gateway. Similarly, the AI guided Physical Assessment and Photo Capture process 370 will be performed at a UME Gateway controlled facility for equipment received via the Inbound White Glove Logistics step 360 to get the pictures and above information into the UME Gateway via the Triage Processing group 380. Once the initial set of information and photographs about medical devices entering the UME Gateway is captured an AI Image Processing step 382 occurs to automatically identify the type make, model, accessories and specifications of the medical equipment, validate that the photos and information captured in the previous steps appears complete and accurate for the device type it determined, and tag any photos containing confidential information to avoid public disclosure. The AI models in the Triage Processing group 380 incorporate data from the Product Specifications and Compatibility database 222 in performing the identification and validation tasks in the AI Image Processing step 382 and then further assigns a confidence interval during to the medical equipment identification assignment related to how confident the AI is that the assigned identification is accurate. Information and photos about the medical equipment are then passed to a series of AI Guided Multipoint Data Enrichment steps 384 which automatically seek any additional information from within the UME Gateway or instruct human staff to follow a guided process to augment or update the photos or data related to a medical device when deemed necessary to optimize the downstream escape path decision making and processing and improve the content available for potential buyers. Two additional human assisted information gathering steps that might be requested include performing the Power On Testing step 386 to confirm any electronic medical devices are capable of powering up when connected to appropriate power source or charged batteries and/or the rePhoto™ and Deeper Data or Condition Assessments step 388 which provides AI guided instructions as to what additional information gathering or device testing and condition assessments should be performed. An updated confidence interval related to the information about the medical equipment is assigned by the AI after any of the AI Guided Multipoint Data enrichment steps 384 are performed. If the Physical Assessment and Photo Capture process 370 or AI during the AI Image Processing step 382 (or both, depending on the situation) determine from the photos or available data that a medical device may contain ePHI, biohazards, environmental risks or other hazardous materials the AI Guided Multipoint Data Enrichment steps 384 will generate a work order to perform the ePHI and Nonconforming Remediation step 387 to address these risks and generate certificates documenting the remediation that took place prior to moving forward with escape path selection and processing. After all Triage Processing group 380 steps are complete the information about the medical equipment is passed to the reFramer™ AI Econometric Evaluation Engine 120 which performs the AI based analytics and generates escape path and, if relevant, pricing recommendations as described in FIGS. 2a and 2b. The reFramer™ AI Econometric Evaluation Engine 120 then passes its recommendation(s) to the Final Harmonization and QC Analytics step 264 to perform a final AI assisted verification of the recommendation(s) as described in FIG. 2a before escape path processing on the medical equipment takes place. If either the reFramer™ AI Econometric Evaluation Engine 120 or the Final Harmonization and QC Analytics step 264 deem it necessary to revalidate or gather more information about a piece of medical equipment because that information may improve the profitability of the medical equipment, resolve any anomalies, or be needed to make recommendations, they can send data enrichment or validation requests back to the Triage Processing group 380 for completion. The Digitized Business and Contract Rules and Constraints database 190 will be evaluated to provide information for the UME Gateway to automatically generate work orders and step-by-step instructions for the Inbound White Glove Logistics step 360 and Triage Processing group 380 activities to ensure compliance. The Digitized Business and Contract Rules and Constraints database 190 will also be evaluated by the reFramer™ AI Econometric Evaluation Engine 120 based decision-making models to ensure recommendations are in compliance.

There are tens of thousands of combinations of medical equipment brands, models, and device configurations and hundreds of thousands of related sub-assemblies and parts. Every medical device in whatever state of completeness entering the UME Gateway needs to be identified and evaluated to both support the healthcare system's and/or asset owner's asset disposition tracking and to determine what to do with it. Traditional acquisition and identification of medical equipment requires investment in a combination of systems integrations, logistics, labor, warehousing, and inventory management services all of which can outweigh any increase in value the information provides. In the mobile medical segment, most used devices carry as-is values of less than $250 and many are well under $100. This means the new AI models and techniques capable of performing extremely efficient device acquisition and identification by the UME Gateway are critical to generating maximum device reuse and repurposing into the reverse supply chain and yielding more value from disposition for healthcare systems and/or asset owners.

To the extent healthcare systems and/or asset owners can provide information about their assets either through automated integrations with their medical equipment computerized maintenance management system (CMMS) or via more informal email, photos, and spreadsheets, the data will be ingested by the UME Gateway and used to support the initial asset identification and attribution process. As healthcare systems and asset owners often have difficulty efficiently providing this information directly the more typical process will be for them to request field service onsite assessment requests for photographing information about their assets to be captured onsite at their facility or field transport requests for the assets moved to one of the UME Gateway's Operations Centers for photographing and initial information ingestion. In all cases the available data, physical assessment information, and photos will be submitted to a triage process that automatically performs and/or cost effectively determines and guides make, model, accessory, specification, and condition assessments and makes other processing and remediation decisions regarding the medical equipment.

Four specific AI augmented capabilities will be applied during acquisition and identification phase processing to automate very specific tasks that are otherwise economically infeasible to perform on low value medical equipment. First, to the extent any information is provided by healthcare systems or asset owners the Integration, Harmonization and Enrichment engine 330 will be used to match these unique nomenclature makes, model numbers, and features to the standard taxonomy used by the UME Gateway. Matches made and gaps identified will be logged for verification as well as stored for future translations and communications with that specific healthcare system or asset owner as well as incorporated as learning into the overall AI identification capabilities in order to self-improve its taxonomy. Secondly and most common in the absence of data from healthcare systems and/or asset owners, AI image processing models attempt to suggest asset categories, manufacturers, models, included accessories and validate serial numbers and asset owner tag numbers directly from photos. Human triage staff follow a guided process to capture the photos and verify and update the minimal baseline information for medical equipment entering the UME Gateway. Third, the initial data and photos are analyzed to make sure accurate identification and matching to the UME Gateway nomenclature occurred and what additional attributes, specifications, assessments, and questions might be useful to ask about the device as part of the AI Guided Multipoint Data Enrichment Steps 384. Potential exception queues are built for review and human actors will correct or update the information as needed such as when a new device type enters the UME Gateway for the first time. This allows the UME Gateway to continue processing while also retraining the AI models. Fourth, the reFramer™ AI Econometric Evaluation Engine 120 will be applied to recommend when to invest in additional information capture, reshooting photos for merchandising, testing devices for items based on the potential increase in known condition value, and other ROI driven information enrichment dictated by near real-time discernment of market conditions. Depending on the asset, light, heavy, or no additional information will be recommended to be gathered and any applicable work orders will be generated for augmenting the information.

These AI models will be continually retrained and evaluated using a combination of supervised and semi-supervised learning where trained operators specify identification data on healthcare system and/or asset owner data, photos, and other data sets directly and then review and verify machine driven assignments for accuracy. As the models converge in automated accuracy, exception-based inspections can take place using confidence intervals where the system itself identifies where it recommends intervention. The models can be retrained and enhanced as core technology libraries and capabilities evolve in a plug and play manner.

In addition to value-based analysis, contractual, legal and governance requirements will be automatically applied to determine the work performed and information to be captured during activities conducted by members of the Triage Processing group 380. For example, some healthcare systems and/or asset owners may require ePHI checks be formally performed on all electronic devices, extra photos be captured on their devices, or additional detailed data be captured on all assets designated for recycling. These requirements will be inserted into workflows to ensure they are met regardless of the econometric valuation or other determinations related to the assets themselves. Contractual and legal requirements will also be applied to ensure compliance during onsite visits to pick up equipment during the Inbound White Glove Logistics step 360 to make sure devices are cleared through healthcare system protocols, any legal matters associated with potential hazardous materials on the devices and transport regulations are enforced, and charging takes place according to agreed upon entitlement management.

In summary the result of this phase is assets are specifically identified with proper classification, manufacturer, and model numbers along with baseline photos, serial numbers, and asset tags for healthcare system and/or asset owner recordkeeping. Any applicable details about functional condition, cosmetic condition, specifications, accessories, ePHI cleansing, biohazard or environmentally sensitive material remediation, value-added merchandising photo and data capture or otherwise that are justified economically, mandated for regulatory compliance, or required contractually by the healthcare system and/or asset owner will be applied prior to escape path selection and processing.

Figure 4A:
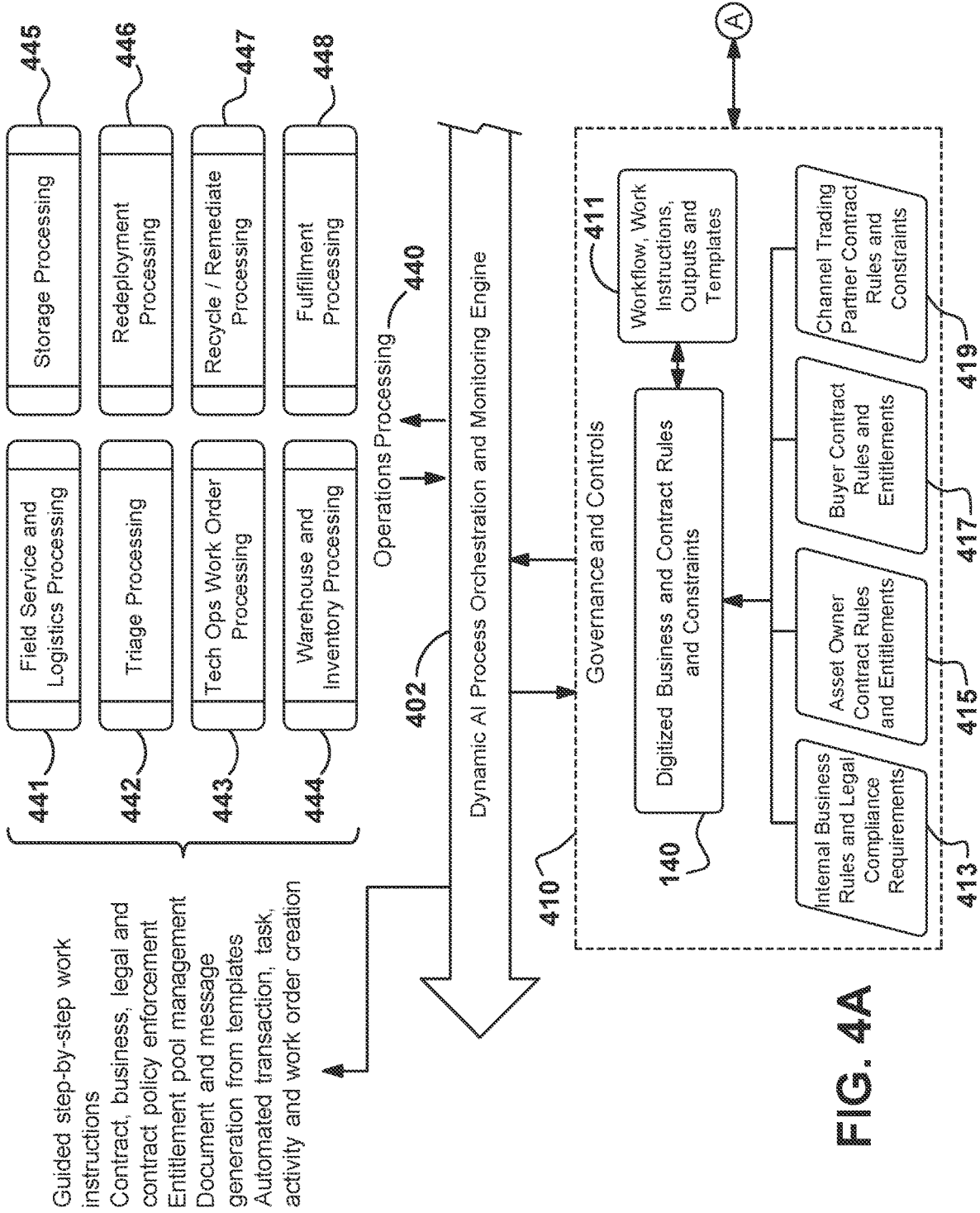
FIGS. 4*a* and 4*b* schematically present a flow chart showcasing the UME Gateway Dynamic AI Process Orchestration and Monitoring Engine system in accordance with aspects of the present disclosure.
Figure 4B:
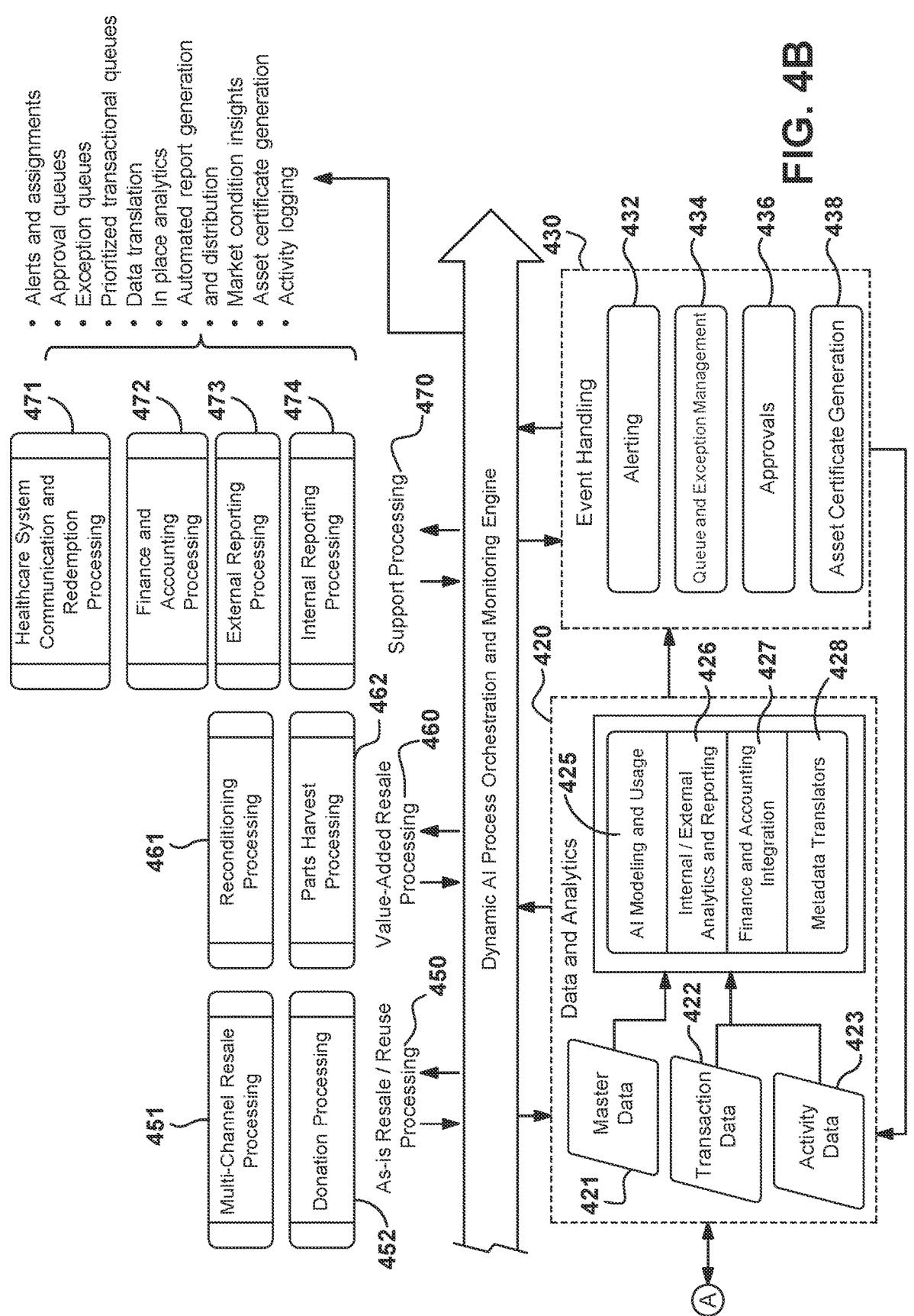

FIGS. 4a and 4b schematically present a UME Gateway Dynamic AI Process Orchestration and Monitoring Engine flowchart 400, showcasing how the UME Gateway relies on this embedded AI enabled business process orchestration method to enable it to process a high-volume of medical equipment in an economically viable way. The UME Gateway Dynamic AI Process Orchestration and Monitoring Engine flowchart 400 includes a Dynamic AI Process Orchestration and Monitoring Engine 402, a Governance and Controls group 410, a Data and Analytics group 420, an Event Handling group 430, an Operations Processing group 440, an As-Is Resale/Reuse Processing group 450, a Value-Added Resale Processing group 460, and a Support Processing group 470.

The Governance and Control group 410 includes a Digitized Business and Contract Rules and Constraints database 190 which is the same as described in FIG. 1a, a Workflow, Work Instructions, Outputs and Templates library 411, an Internal Business Rules and Legal Compliance Requirements database 413, an Asset Owner Contract Rules and Entitlements database 415, a Buyer Contract Rules and Entitlements database 417, and a Channel Trading Partner Contract Rules and Constraints database 419.

The Data and Analytics group 420 includes a Master Data engine 421, a Transaction Data engine 422, an Activity Data engine 423, an AI Modeling and Usage set 425, an Internal/External Analytics and Reporting engine 426, a Finance and Accounting Integration engine 427, and a Metadata Translators engine 428.

The Event Handling group 430 includes an Alerting event handler 432, a Queue and Exception Management event handler 434, an Approvals event handler 436, and an Asset Certificate Generation engine 438.

The Operations Processing group 440 includes a Field Service and Logistics Processing activity 441, a Triage Processing activity 442, a Tech Ops Work Order Processing activity 443, a Warehouse and Inventory Processing activity 444, a Storage Processing activity 445, a Redeployment Processing activity 446, a Recycle/Remediate Processing activity 447, and a Fulfillment Processing activity 448.

The As-Is Resale/Reuse Processing group 450 includes a Multi-Channel Resale Processing activity 451 and a Donation Processing activity 452.

The Value-Added Resale Processing group 460 includes a Reconditioning Processing activity 461 and a Parts Harvesting Processing activity 462.

The Support Processing group 470 includes a Healthcare System Communication and Redemption Processing activity 471, a Finance and Accounting Processing activity 472, an External Reporting Processing activity 473, and an Internal Reporting Processing activity 474.

The Dynamic AI Process Orchestration and Monitoring Engine 402 facilitates, tracks, monitors, and reports on all transactions, data, and activity flowing through the UME Gateway to ensure efficient, effective, and accurate performance is achieved. This includes launching, guiding, and tracking unique individual processes and steps to ensure intended execution, facilitating workflows, generating alerts, reminders, and tasks for addressing exceptions and escalations, dynamically tracking entitlements, usage, approvals, and triggering all cost allocations, charging, discounts, and ledger updates for healthcare systems and/or asset owners including generating any necessary documentation, reports, or transaction integrations required for the UME Gateway's own internal recordkeeping.

The Governance and Controls group 410 is a collection of databases and content templates that contain information relating to digitized business rules, contract rules and requirements, legal compliance requirements, entitlements, constraints, step-by-step process flows and instructions, and standard presentation formats to be used throughout the UME Gateway.

The Digitized Business and Contract Rules and Constraints database 190, which is the same as described in FIG. 1*a*, is a database of digitized contract terms and other business, compliance, and governance constraints that are automatically applied to every relevant decision and transaction in the UME Gateway. This database consolidates, normalizes, harmonizes, and reformats information from the Internal Business Rules and Legal Compliance Requirements database 413, the Asset Owner Contract Rules and Entitlements database 415, the Buyer Contract Rules and Entitlements database 417, and the Channel Trading Partner Contract Rules and Constraints database 419 so a single prioritized and harmonized set of governance information can be efficiently incorporated into AI processing and other automations in the UME Gateway.

The Workflow, Work Instructions, Outputs and Templates library 411 is a content management system and repository containing information regarding the step-by-step workflow and work instructions to be consistently applied in the UME Gateway along with stakeholder approved templates for documents, emails, SMS messages, asset certificates, agreements and terms, reports, and other outputs generated by and sent from the UME Gateway.

The Internal Business Rules and Legal Compliance Requirements database 413 is a database containing information regarding the internal business rules and legal compliance requirements of the UME Gateway and as applicable to the medical device disposition industry and the UME Gateway's unique need to efficiently and comprehensively handle the volume of equipment and device types and escape paths.

The Asset Owner Contract Rules and Entitlements database 415 is a database containing information regarding the agreements, entitlements, pricing, service levels, templates, and unique medical device asset handling, governance, processing, and compliance requirements that need to be enforced for each healthcare system and asset owner contributing medical equipment to the UME Gateway.

The Buyer Contract Rules and Entitlements database 417 is a database of all UME Gateway medical equipment buyers' master agreements and transaction specific contract terms and constraints which can be automatically applied to and updated by every decision and transaction in the UME Gateway. This allows every event to be captured and any custom pricing, discounts, fulfillment requirements, and entitlements associated with a given transaction/decision to be automatically applied on a buyer's behalf.

The Channel Trading Partner Contract Rules and Constraints database 419 is a database containing information regarding the contract rules, terms, pricing, warranties, inclusions, exclusions, and other constraints of resale channels and medical equipment trading partners of the UME Gateway that provide ancillary services, parts harvesting, equipment reconditioning, training, and other value added inputs and capabilities to the UME Gateway for use in AI based escape path, channel selection, and pricing decisions for medical equipment.

The Data and Analytics group 420 is a group of databases, processes, and automations that provide data, analytics, integration, business intelligence, reporting, and AI capabilities to the UME Gateway for automated decision making, anomaly or issues detection, business performance management, communications, integration and monitoring, and specifically with regards to AI model development and usage, stakeholder business and activity reporting, data integration and data harmonization, financial controls, and business reporting.

The Master Data engine 421 captures, consolidates, cleans, and builds relationships between all master data in the UME Gateway covering areas like product information, buyer, seller, and partner accounts and contacts hierarchies, channel configurations, addresses and geography coding, agreements, facilities, and other core entities.

The Transaction Data engine 422 generates and captures large amounts of information regarding all transactions made by the UME Gateway, both historical and current and summarizes and formats this information into a structure suitable for consumption by AI and other analytics methods.

The Activity Data engine 423 generates and captures large amounts of information regarding the non-transactional activity within the UME Gateway, specifically with regards to things such as workflows, queues, approvals, work orders, logistics events, tasks, quoting, lotting, kitting, reconditioning, parting, and other medical device processing and formats this information into a structure suitable for consumption by AI and other analytics methods.

The AI Modeling and Usage set 425 is a set of models that the UME Gateway uses to train, implement, and optimize its AI capabilities.

The Internal/External Analytics and Reporting engine 426 generates automated and on-demand internal and external analytics reports and alerts regarding transactional and activity data received from the Dynamic AI Process Orchestration and Monitoring Engine 402, the Transaction Data engine 422, and the Activity Data engine 423.

The Finance and Accounting Integration engine 427 works to convert UME Gateway data received from the Dynamic AI Process Orchestration and Monitoring Engine 402, the Transaction Data engine 422, and the Activity Data engine 423 into financial transactions that can be processed and audited by financial and cost accounting systems and processes.

The Metadata Translators engine 428 works to translate and harmonize data received from the Dynamic AI Process Orchestration and Monitoring Engine 402, the Transaction Data engine 422, the Activity Data engine 423, and other third-party systems into a format usable by the UME Gateway, or, in the event the data is being sent from the UME Gateway to a third-party system, it will translate and harmonize to a format required by the third-party system.

The Event Handling group 430 is a group of event handlers that respond to certain events that occur within the UME Gateway and generate a signal, message, alert, task, process or workflow trigger, approval step, or other response corresponding to a given event for the Dynamic AI Process Orchestration and Monitoring Engine 402 to incorporate and manage the execution of by assigning it to another AI or human agent.

The Alerting event handler 432 creates an alert in response to certain information or events and sends it to the Dynamic AI Process Orchestration and Monitoring Engine 402 and/or a user or automated AI agent of the UME Gateway with in-context information needed for automated or human assisted responses to take place based on the nature of the information or event.

The Queue and Exception Management event handler 434 monitors the work queues in near-real time to dynamically reprioritize workloads and tasks that need to be addressed in a timely manner, as well as managing exceptions and notifying a user or automated AI agent of the UME Gateway or creating tasks and alerts about the exception so it can be dealt with.

The Approvals event handler 436 monitors activity within the UME Gateway to request and confirm approvals are taking place from authorized personnel when necessary prior to a human or AI agent making a decision or undertaking an action.

The Asset Certificate Generation engine 438 dynamically creates an asset certificate to serve as compliance documentation for healthcare systems and other asset owners when donations, recycling, ePHI destruction work orders, hazardous or environmentally sensitive material remediation work orders, or other similar types of events are completed.

The Operations Processing group 440 is a group of processes related to the day-to-day operational moves, storage, and other handling of medical equipment processed in the UME Gateway.

The Field Service and Logistics Processing activity 441 is a set of steps in which labor and equipment is scheduled and provided for onsite medical equipment assessments, inventory capture, moves within a healthcare system or other asset owner's facilities, or logistics transport to a UME Gateway Operations Center location.

The Triage Processing activity 442 is a set of steps in which photos and information about a piece of medical equipment are captured and enriched to determine the best course of action for a given piece of medical equipment entering the UME Gateway. Details of triage processing activities are included in the descriptions from FIG. 3 including the Physical Assessment and Photo Capture step 370 and the activities in the Triage Processing group 380.

The Tech Ops Work Order Processing activity 443 is a set of steps in which work orders for technical operations such as repairing, testing, kitting, data destruction, and other special medical device processing steps are created, performed, tracked, handled, and completed by trained, certified biomedical technicians and all relevant data about the work order events is captured.

The Warehouse and Inventory Management processing activity 444 is a set of steps in which the medical equipment enters, moves within, is processed and held temporarily by, and ultimately leaves a UME Gateway location including all near real-time tracking of inventory stage, status, and location within the UME Gateway location to ensure efficient and expedient movement and storage of medical equipment.

The Storage Processing activity 445 is a set of steps in which the longer-term storage of medical equipment at a UME Gateway location is managed for the convenience of a healthcare system or asset owner to ensure safe, secure, efficient, and expedient holding of medical equipment while in storage and return of the medical equipment or its transition to another disposition escape path when the storage period ends.

The Redeployment Processing activity 446 is a set of steps in which visibility and analytics are provided for authorized healthcare system and/or asset owners to see their available medical equipment held in a UME Gateway location and select and trigger single push button redirection of that equipment back to the location it was sourced from or any other facility the healthcare system and/or asset owner chooses and then ensures the Fulfillment Processing activity 448 for that medical equipment is performed.

The Recycling and Remediation Processing activity 447 is a set of steps in which work orders are processed to detect and destroy or remove ePHI or hazardous or environmentally sensitive materials and/or convert, tear down, and sort medical devices into their constituent commodities, and/or transfer medical equipment to recyclers authorized by the UME Gateway to process the materials in compliance with local, state and federal legal requirements and responsible recycling standards appropriate for each medical device type. This processing is automatically integrated with the Asset Certificate Generation engine 438 to generate compliance certificates for healthcare systems or other asset owners of the medical devices being processed.

The Fulfillment Processing activity 448 is a set of steps in which orders made by buyers or requests from the Redeployment Processing activity 446 are pulled, packaged, palletized, and shipped in an efficient manner with special care and handling needed to protect sensitive medical devices that are no longer in their original packaging.

The As-Is Resale/Reuse Processing group 450 is a group of processes related to the efficient resale and reuse of medical equipment in essentially the same condition and format it was received by the UME Gateway.

Figure 6A:
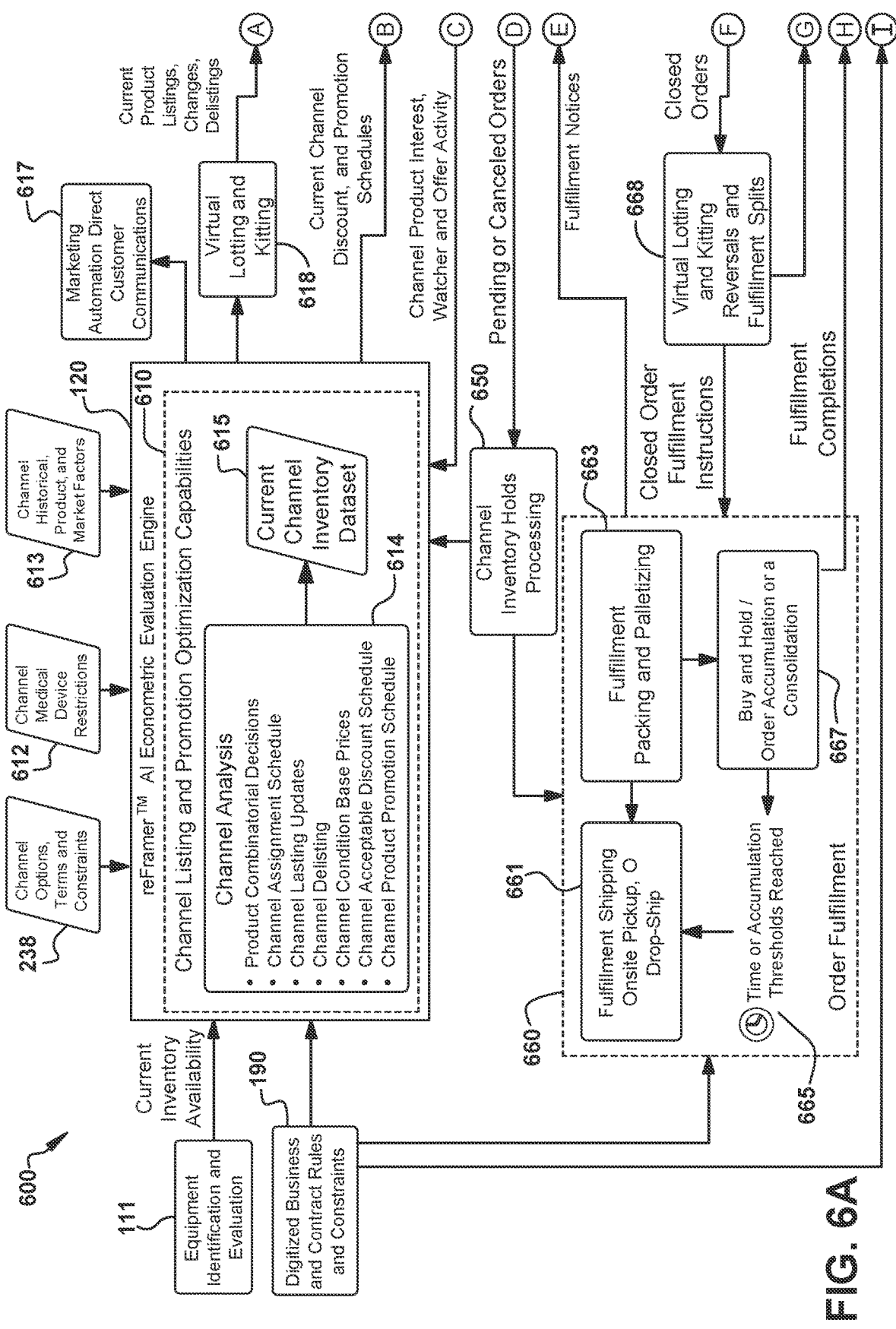
FIGS. 6*a* and 6*b* schematically present a flow chart showcasing the UME Gateway Multi-Channel Optimization system in accordance with aspects of the present disclosure.
Figure 6B:
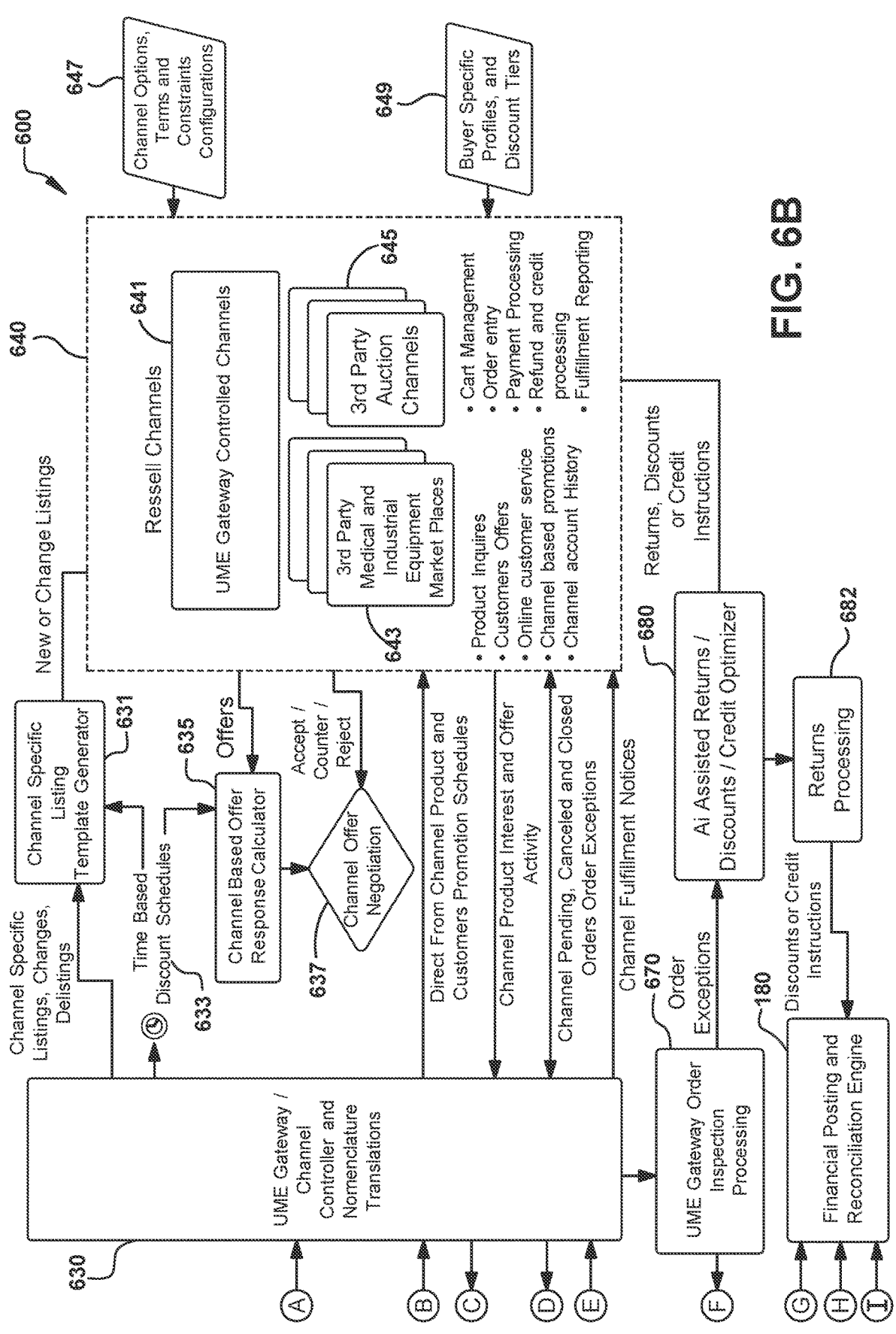

The Multi-Channel Resale Processing activity 451 is a set of steps in which pieces of medical equipment are listed for sale on multiple channels and is further described in detail in FIGS. 6*a* and 6*b*.

The Donation Processing activity 452 is a set of steps in which the ownership of medical equipment is transferred at no cost to a nonprofit or other entity approved by the UME Gateway. This processing is automatically integrated with the Asset Certificate Generation engine 438 to generate compliance certificates for healthcare systems or other asset owners of the medical devices being processed, and all relevant records are created for the healthcare system or other asset owner that provided the medical equipment.

The Value-Added Resale Processing group 460 is a group of processes related to increasing the net value that can be generated from pieces of medical equipment through investments of labor and materials that recondition or harvest parts from the medical equipment with the resulting working equipment and parts being made available for sale. The activities in this group are further described in detail in FIGS. 7a and 7b.

The Reconditioning Processing activity 461 is a set of steps in which parts, labor, and materials are applied to a piece of medical equipment to restore it to working and/or patient-ready condition that meets manufacturer specifications allowing the medical equipment to be sold at a higher price point that more than offsets the added costs.

The Parts Harvest Processing activity 462 is a set of steps in which pieces of medical equipment are systematically taken apart according to an AI guided process in order to systematically protect and catalog the valuable parts that can then be sold or used by the UME Gateway to repair and extend the life of other medical equipment.

The Support Processing group 470 is a group of processes related to tracking, accounting for, summarizing, and providing management level reporting and governance for the other processes performed within the UME Gateway Dynamic AI Process Orchestration and Monitoring Engine flowchart 400.

The Healthcare System Communications and Redemption Processing activity 471 is a set of steps including self-service portals, mobile interfaces, and integrations in which healthcare systems and/or asset owners can see and spend or collect the earnings they receive from having their medical equipment processed through and resold by the UME Gateway as well as track all other UME Gateway medical equipment records and service records. The steps in the Healthcare System Communications and Redemption Processing activity 471 are further described in detail in FIGS. 8a and 8b.

The Finance and Accounting Processing activity 472 is a set of steps in which entitlements and usage are dynamically tracked and in which all cost allocations, charging, discounts, and ledger updates are performed/executed in the UME Gateway's financial and accounting systems and databases and then provided to healthcare systems and/or asset owners, buyers, and other trading partners for their financial tracking and reporting.

The External Reporting Processing activity 473 is a set of activities in which necessary documentation, reports, or data and system integrations required by a given healthcare system and/or asset owner, buyer, trading partner, governing agency, or other stakeholders are generated and transmitted for their own internal record keeping. Self-service reporting and mobile apps are made available for healthcare systems and asset owners to perform this task as further described in detail in FIGS. 8a and 8b.

The Internal Reporting Process 474 is a process in which necessary documentation, reports, or system integrations required by the UME Gateway for its own internal business performance management, record keeping, and optimization analysis are generated and transmitted to appropriate UME Gateway users or AI automations that consume this data.

The flow of the UME Gateway Dynamic AI Process Orchestration and Monitoring Engine flowchart 400 is described herein. Thousands of medical devices and associated transactions are processed through the UME Gateway every day representing the different types of processes, transactions, and activities within the Operations Processing group 440, the As-Is Resale/Reuse Processing group 450, the Value-Added Resale Processing group 460, and the Support Processing group 470. The Dynamic AI Process Orchestration and Monitoring Engine 402 is continuously tracking, facilitating, and monitoring all of these processes, transactions, and activities and passing information and analytics to and from these groups in near real-time as part of the normal course of business. This allows the UME Gateway to cost effectively handle all types of medical equipment, regardless of value, according to the unique needs and requirements of stakeholders involved. The Dynamic AI Process Orchestration and Monitoring Engine 402 facilitates by guiding users and automations through detailed step-by-step work instructions required for each type of process, transaction and activity, dynamically applying different business, legal and contract rules and compliance requirements and managing entitlement pools from the Governance and Controls group 410 to make sure every execution follows the unique rules and documentation requirements associated with what activity is being done, the type of medical device, the healthcare systems or other asset owners involved, the buyer's expectations, and any other specific requirements from governance agencies and third-party trading partners. The Dynamic AI Process Orchestration and Monitoring Engine 402 also facilitates by ensuring all documents and messages generated from AI and other automations use the appropriate templates and messages in the Workflow, Work Instructions, Outputs and Templates library 411 based on the type of transaction or activity and stakeholders involved. The Dynamic AI Process Orchestration and Monitoring Engine 402 can further facilitate by determining when additional actions are needed based on what is happening within existing processes and then automatically generate transactions, activities, tasks, and work orders to trigger those actions. The Dynamic AI Process Orchestration and Monitoring Engine 402 enables more focused, timely and accurate work is performed by human actors and AI automations by using capabilities in the Event Handling Group 430 to automatically generate alerts and assignments and by building queues for approvals, exception handling events, and prioritized transaction workloads to make sure the most important actions occur first and time is not wasted determining where a process is and what needs to occur next. As processes cross organizational boundaries and systems, the Metadata Translators engine 428 enables the Dynamic AI Process Orchestration and Monitoring Engine 402 to translate and communicate across those boundaries and systems. The Dynamic AI Process Orchestration and Monitoring Engine 402 uses the capabilities from the Data and Analytics group 420 to provide relevant in-place analytics to humans, automated agents and AI users of the UME Gateway to make quicker decisions when performing and approving tasks, to generate and communicate internal and external reports and data needed by each process, and to provide early awareness of changing market conditions and insights that should lead to investigation and potential changes in the UME Gateway processes, business rules, and AI models. Where needed in a process or reporting activity, the Dynamic AI Process Orchestration and Monitoring Engine 402 is able to produce and present asset certificates for ePHI removal, hazardous material remediation, recycling activity, donations, and other compliance events by accessing the Asset Certificate Generation engine 438. In performing its work, the Dynamic AI Process Orchestration and Monitoring Engine 402 continuously reads from the Master Data engine 421 and pushes available data through the Transaction Data engine 422 and the Activity Data engine 423 to funnel all relevant business activity through the AI Modeling and Usage set 425 and the Metadata Translators engine 428 so they can help facilitate its work. Likewise The Dynamic AI Process Orchestration and Monitoring Engine 402 continuously pushes available data through the Transaction Data engine 422 and the Activity Data engine 423 to funnel all relevant business activity through the Internal/External Analytics and Reporting engine 426 and Finance and Accounting Integration engine 427 so other reporting and analytics can be performed and financial system transactions can be created to perform financial and cost accounting tasks and govern the UME Gateway finances. The Dynamic AI Process Orchestration and Monitoring Engine 402 monitoring capabilities are enhanced by using AI and other algorithms to detect and communicate potential anomalies, risks, concerns, high value opportunities, or business, contractual, or compliance breaches using the data from the Governance and Controls group 410, the capabilities of the Data and Analytics group 420, and Event Handling group 430. The Data and Analytics group 420 is also in communication with the Governance and Controls group 410 and the Event Handling group 430 to facilitate and aid their functionalities.

Central to the UME Gateway's process orchestration is the digitization of baseline business rules, workflows, expected outputs, templates, and contractual commitments unique to the disposition of medical equipment. As transactions and activities flow through the UME Gateway these rules, required templates, and contractual commitments with healthcare systems, asset owners, buyers, and other stakeholders are dynamically applied to determine and initiate tasks, check and verify workflows are performed correctly, proper documentation is created, exception and approval notifications and alerts are generated and handled, and customized data capture and reporting is performed. By handling and automating decision making this automated technology allows healthcare systems and/or asset owners to adopt and enforce their own unique disposition process, funnel significantly more medical equipment through individual product device category requirements and satisfy the unique needs of buyers in an economically feasible way. Because process orchestration is embedded throughout every aspect of the UME Gateway the following are some examples of how these capabilities are used in the present teaching.

Business process orchestrations will guide operations processes by generating contract and business rule compliant work instructions to guide acquisition, processing, warehousing, storage, and escape path release for each piece of medical equipment inventory. For example, the system can automatically specify the number, angles, and types of photos required for each specific device type during triage; determine whether equipment quarantining, remediation, or returns should take place if biohazards, ePHI or nonconforming materials are discovered based on the healthcare system and/or asset owner's unique governance requirements and then automatically process the corresponding work orders, notifications, and/or certificates of destruction as applicable; require or prevent recycling of a piece of medical equipment depending on contractual commitments; or determine how much logistics will be charged for an inbound field service request and automatically process the related financial and if applicable discount transactions and update entitlement pools. The comprehensive data driven process orchestrations allow the UME Gateway to adapt to any number of other situations that might require different handling based on unique contractual commitments.

Storage specific processes are executed for medical devices for a healthcare system's and/or asset owner's assets where they are either unsure of what to do with the equipment at the time of release or are certain that they want the assets back at some future point. Examples of how the process orchestration capabilities of the UME Gateway support the storage process include prohibiting stored assets from entering other disposition escape paths until such determination has been made by an authorized representative, providing transparency alerts, and reports to healthcare systems and/or asset owners of what is being held to make timely decisions and to not forget about and continue paying for devices that are stored offsite, triggering notifications, and required work orders and tracking if and when items must be made available in a UME Gateway Operations Center for the healthcare system's and/or asset owner's staff to perform their scheduled legally required preventive maintenance tasks, and performing all work order creation and tracking for medical device redeployments or transitions to other disposition escape paths.

Redeployment process orchestrations provide visibility and analytics for authorized healthcare system capital planners and supply chain professionals to evaluate and trigger single push button redirection of any of their available disposition assets back to source locations or direct them to any other facility they operate when needs arise. Customized work orders needed to properly pull, pack, and provide white glove transportation services for different types of sensitive medical devices are triggered and monitored through execution while all service records and financial charging transactions for the redeployment service are automatically processed by the system into healthcare system ledgers.

Recycling or other remediation process orchestrations determine contractual or legal requirements necessary for each medical device and trigger work orders and vendor communications for any needed support. Any required remediation certificates for healthcare system and/or asset owner compliance are also automatically generated. For example, devices discovered to contain biohazards, gases, or controlled pharmaceuticals require quarantining and specialized vendor remediation services to prevent accidental release, while devices with batteries, mattresses, and Cathode Ray Tube (CRT) monitors need specialized environmental processing to avoid entering a landfill. The process orchestration rules further dynamically identify based on near real-time resource availability the optimal amount of pre-processing and tear down labor investments to perform on assets to minimize expenses from downstream recycling vendors with the supporting work orders being generated and tracked to ensure compliance.

The UME Gateway provides donation process orchestrations to avoid recycling medical equipment that cannot be profitably resold, but still offers value to improve quality and access to healthcare services offered by nonprofit organizations. This recycling avoidance also helps healthcare systems and/or asset owners achieve goals for sustainability and reuse. These process orchestrations ensure items can be donated according to rules provided and managed by healthcare systems and/or asset owners including their designated approval steps, tax reporting compliance requirements, and preferred beneficiaries who can receive donated medical equipment. Items targeted for donation are communicated to registered nonprofit partners who are qualified to participate in the UME Gateway. Donation transactions are automatically processed, records are recorded and donation letters from the beneficiary to the healthcare systems and/or asset owners are published through the UME Gateway. Donation recipients are also able to move their own assets through disposition workstreams effectively exchanging medical devices unsuitable for their specific nonprofit beneficiaries for other assets that are necessary and appropriate for the countries, facilities, or types of care they support.

Examples of the business process orchestration capabilities associated with the multi-channel resale process, the reconditioning and parts harvesting processes, and the healthcare system communications and redemption process are shown in FIGS. 6a and 6b, 7a and 7b, and 8a and 8b, respectively.

The process orchestration capabilities of the UME Gateway include finance and accounting processes and transaction creation to make sure all financial transactions are properly posted according to Generally Accepted Accounting Principles (GAAP) and that all earnings and expenses associated with every healthcare system and/or other asset owner's transactions can be reviewed and traced back to the specific medical device handling, resale, processing, or service event performed. This includes integrations into finance and accounting systems controlled by the UME Gateway used to generate external financial reports as well as financial transaction records that can be automatically imported or manually entered into a healthcare system and/or other asset owner's financial systems.

The process orchestration capabilities of the UME Gateway provide data capture, logging, posting, and integration necessary for improving the underlying AI models and providing internal and external business reporting beyond what is required for finance and accounting. This provides stakeholders with access to all operating details, business events, and information in the UME Gateway in near real-time for short and long-term analysis, decision making, compliance tracking, and process and asset management optimization needed to improve performance. The UME Gateway's process orchestration activities are uniquely suited to quickly detect, communicate, and respond to market condition changes related to a specific device or device type due to manufacturer, supply chain, or other business and epidemiological issues or events to make sure the healthcare system and/or asset owner priorities for their medical equipment are best served and they can adjust their capital planning and disposition plans accordingly in response to this information.

The process orchestration capabilities of the UME Gateway dynamically track entitlements, usage, and perform all cost allocations, charging, discounts, and ledger updates for healthcare systems and/or asset owners including generating any necessary documentation, reports, or transaction integrations they require for their own internal recordkeeping. Alerts are generated to authorized approvers when activities such as recycling volumes, redeployment, asset remediation events, logistics volumes, or other actions exceed thresholds. Any added costs and customer charging generates additional background work order transactions and approval processes for these events.

In summary the process orchestration elements of the UME gateway enable economically efficient processing of extremely high volumes of a healthcare system's and/or asset owner's medical devices while ensuring all legal, contractual, and business policy compliance requirements are met by automating dynamic processes and leveraging AI in a way that limits human intervention to managing priority-based queues, reviewing integrity reports, and performing step-by-step instructions to fulfill work orders. This consistent execution also ensures human intervention and labor investments are targeted to areas of greatest need and value. Simultaneously the extensive structured data capture and logging from the processes is used to train and support both AI driven models and other analytics, systems integration, and reporting needs.

Figure 5A:
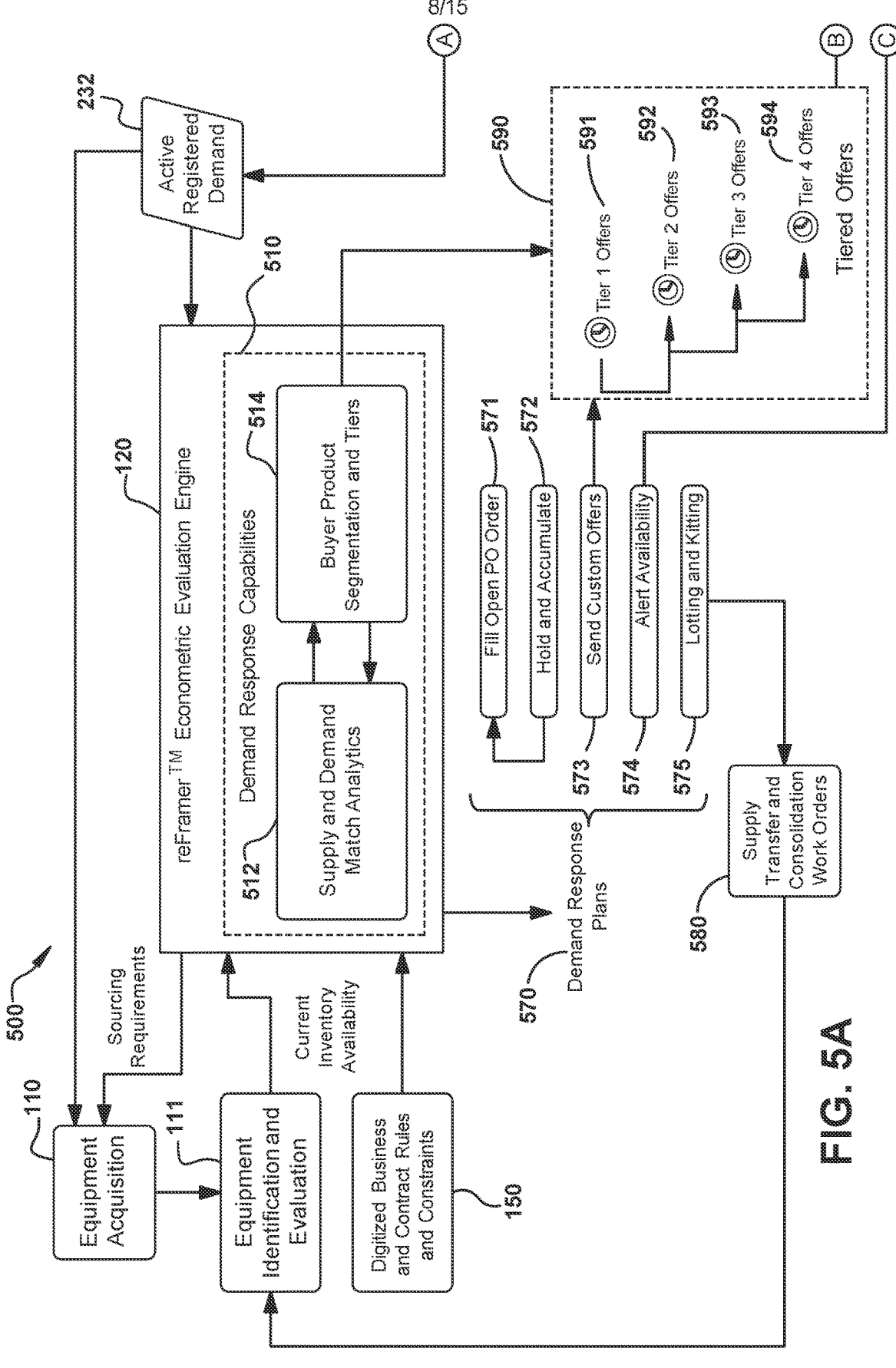
FIGS. 5*a* and 5*b* schematically present a flow chart showcasing the UME Gateway Active Registered Demand Module and Demand Response Plans system in accordance with aspects of the present disclosure.
Figure 5B:
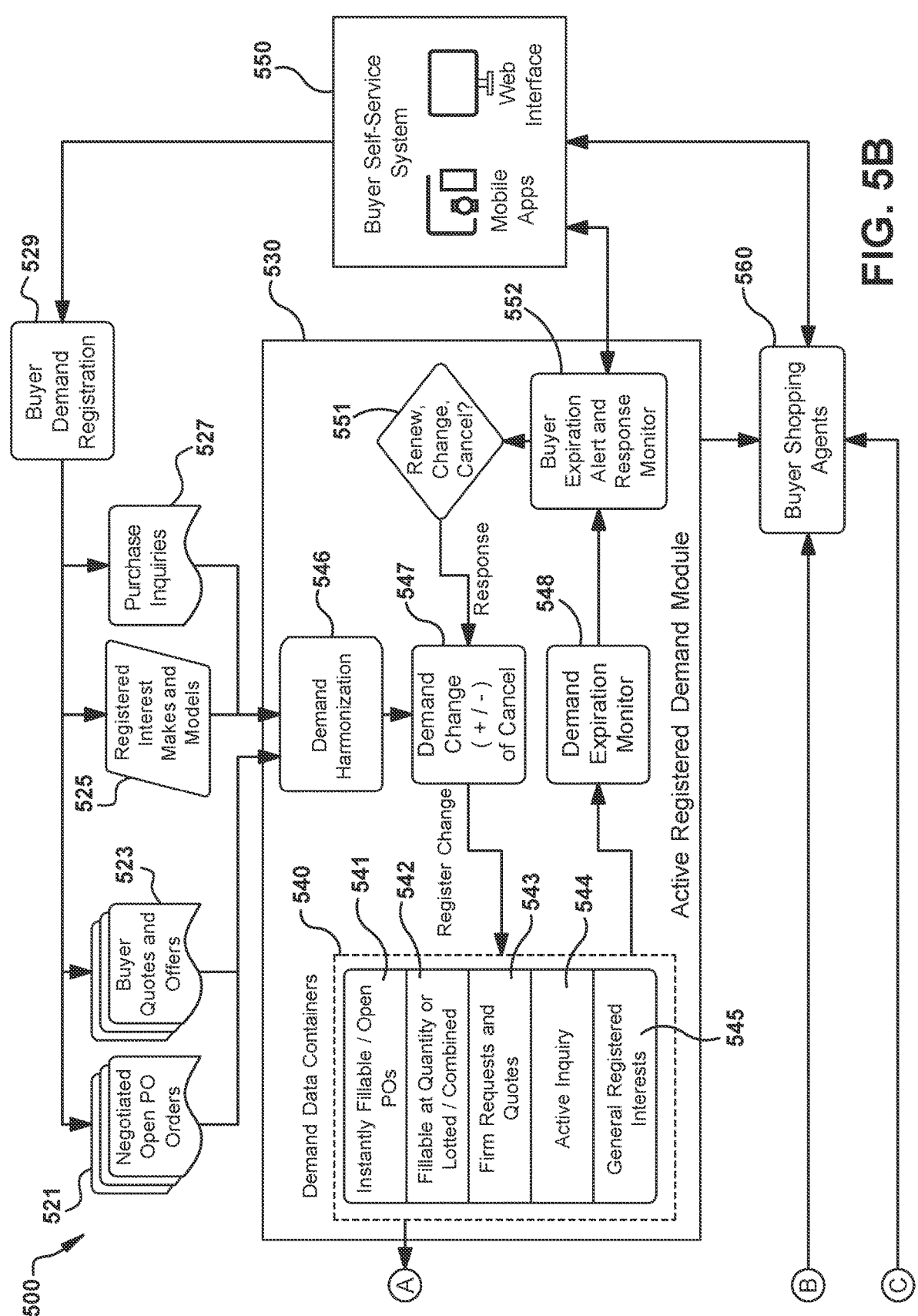

FIGS. 5a and 5b schematically present a UME Gateway Active Registered Demand Module and Demand Response Plans flowchart 500, showcasing how the demand registration functions of the UME Gateway operate. The UME Gateway Active Registered Demand Module and Demand Response Plans flowchart 500 includes the Equipment Acquisition process 110 found in FIG. 1a, the Equipment Identification and Evaluation process 111 found in FIG. 1a, the Digitized Business and Contract Rules and Constraints database 190 found in FIG. 1a, the reFramer™ AI Econometric Evaluation Engine 120 found in FIG. 1a, a Demand Response Capabilities group 510 within the reFramer™ AI Econometric Evaluation Engine 120, the Active Registered Demand database 232 found in FIG. 2b, a Negotiated Open PO Orders database 521, a Buyer Quotes and Offers database 523, a Registered Interest Makes and Models database 525, a Purchase Inquiries database 527, a Buyer Demand Registration process 529, an Active Registered Demand Module group 530 which contains details about the Active Registered Demand Module 150 found in FIG. 1b, a Buyer Self-Service Systems capability 550, a Buyer Shopping Agents engine 560, a Demand Response Plans group 570, a Supply Transfer and Consolidation Work Orders process 580, and a Tiered Offers group 590.

The Demand Response Capabilities group 510 includes a Supply and Demand Match Analytics engine 512 and a Buyer Product Segmentation and Tiers engine 514.

The Active Registered Demand Module group 530 includes a Demand Data Containers subgroup 540, a Demand Harmonization engine 546, a Demand Change (+/−) or Cancel step 547, a Demand Expiration Monitor engine 548, a Renew/Change/Cancel step 551, and a Buyer Expiration Alert and Response Monitor step 552. The Demand Data Containers subgroup 540 includes an Instantly Fillable/Open POs container 541, a Fillable at Quantity or Lotted/Combined container 542, a Firm Requests and Quotes container 543, an Active Inquiry container 544, and a General Registered Interests container 545.

The Demand Response Plans group 570 includes a Fill Open PO Order response 571, a Hold and Accumulate response 572, a Send Custom Offers response 573, an Alert availability response 574, and a Lotting and Kitting response 575.

The Tiered Offers group 590 includes a Tier 1 Offers list 591, a Tier 2 Offers list 592, a Tier 3 Offers list 593, and a Tier 4 Offers list 594.

The Equipment Acquisition process 110 found in FIG. 1a is the process by which medical equipment is made available to the UME Gateway. This step can receive sourcing requests related to known active demand from the Active Registered Demand database 232 and the reFramer™ AI Econometric Evaluation Engine 120 to seek or source specific medical equipment that has known current demand. Additional details about the processes and activities of this process are as described in FIG. 3.

The Equipment Identification and Evaluation process 111 found in FIG. 1a is the process by which image processing is combined with AI and other techniques to efficiently identify makes, models, conditions, system completeness, specifications, included accessories, and other basic information about medical equipment to feed into subsequent analysis, databases, and automations that can be processed by the UME Gateway. Once the basic information is known, the information about current available inventory is sent to the reFramer™ AI Econometric Evaluation Engine 120 where among other things it can determine if newly available UME Gateway inventory could be used to satisfy active demand. Additional details about the processes and activities of this process are as described in FIG. 3.

The Digitized Business and Contract Rules and Constraints database 190 found in FIG. 1*a* contains among other things buyer and channel trading partner contract rules, entitlements, and constraints that specify blanket terms and conditions which may apply to known active demand from a given buyer or trading partner. These terms and conditions need to be considered when deciding whether and how the UME Gateway should respond to known active demand for medical devices.

The reFramer™ AI Econometric Evaluation Engine 120 found in FIG. 1*a* performs, among other things, the prioritized identification of the most needed inventory to fulfill demand so it can be sourced by the UME Gateway, the matching of UME Gateway medical equipment supply against active registered demand for AI econometric modeling to recommend disposition escape paths and pricing, and the segmentation and tiering of buyers to assign prioritized sequences for making current UME Gateway inventory available to those buyers. Note the reFramer™ AI Econometric Evaluation Engine 120 may or may not choose to act upon active registered demand when recommending an escape path and/or pricing for a given piece of medical equipment as it considers many other factors as described in FIGS. 2*a* and 2*b*.

The Demand Response Capabilities group 510 is a group of AI driven models and automations within the reFramer™ AI Econometric Evaluation Engine 120 that analyzes information to determine what UME Gateway available inventory matches known active demand and assigns buyers to segments and tiers to prioritize the order and method of allocating, offering, or communicating scarce UME Gateway inventory to those buyers if applicable.

The Supply and Demand Match Analytics engine 512 uses AI models to continuously match the rapidly changing medical equipment supply of available UME Gateway medical devices, parts, and accessories to all potential data from the Active Registered Demand database 232 which that inventory can fulfill including any lotting, kitting, reconditioning, or parts harvesting that would be required to be performed on that medical equipment to meet such demand. Other AI capabilities in the reFramer™ AI Econometric Evaluation Engine 120 use this information to make escape path and pricing recommendations as well as any applicable detailed demand response plans.

The Buyer Product Segmentation and Tiers engine 514 is an AI based set of models and automations that assign buyers to segments and tiers based on their known active registered demand, stated preferences, and actual historical behavior when it comes to purchasing medical equipment from the UME Gateway. Subsequent AI models incorporate this information when recommending the timing and manner in which available medical equipment should be allocated to, held for, offered to, and/or communicated to specific buyers.

The Active Registered Demand database 232 found in FIG. 2*b* contains details of all known and actionable active registered demand for medical equipment for use by the reFramer™ AI Econometric Evaluation Engine 120 and can be accessed by the sourcing steps of the Equipment Acquisition process 110 to focus resources on communicating known needs to acquire medical equipment that is currently demanded from healthcare systems and/or asset owners.

The Negotiated Open PO Orders database 521 is a database containing information regarding current, legally binding detailed open purchase orders that are submitted by buyers to the UME Gateway with all information necessary to complete a sales transaction.

The Buyer Quotes and Offers database 523 is a database containing information regarding current nonbinding quotes and offers for specific medical equipment submitted by buyers into the UME Gateway that contain details on required quantities, specifications, accessories, conditions, and other terms useful to negotiate and complete a sales transaction.

The Registered Interest Makes and Models database 525 is a database containing information regarding a buyer's ongoing interest in specific makes and models of medical equipment along with any required features or conditions to the UME Gateway so supply can be communicated as it is made available.

The Purchase Inquiries database 527 is a database containing information regarding current inquiries from buyers of items they are actively and immediately looking to purchase if supply were to be available from UME Gateway and suitable terms could be agreed on. These are often followed up on by the UME Gateway and either converted directly into sales transactions or into the Negotiated Open PO Orders database 521 or the Buyer Quotes and Offers database 523 with details necessary to actively identify supply.

The Buyer Demand Registration process 529 is a process where information communicated from buyers via surveys and forms directly completed by the buyer using UME Gateway portals, web sites and mobile apps, or via buyer phone calls and messaging with UME Gateway AI or human customer service agents, is automatically entered into either the Negotiated Open PO Orders database 521, the Buyer Quotes and Offers database 523, the Registered Interest Makes and Models database 525, and/or the Purchase Inquiries database 527 as applicable.

The Active Registered Demand Module group 530 which contains details about the Active Registered Demand Module 150 found in FIG. 1*b* includes a set of automations and processes to convert information from buyers into the specific structure, format, content, quality, and type of data that can be entered into the Active Registered Demand database 232 and otherwise used and acted upon by the AI and other automations within the UME Gateway.

The Demand Data Containers subgroup 540 is a partitioned database that formats and organizes the various types of buyer demand based on type and action that can be taken upon that buyer demand.

The Instantly Fillable/Open POs container 541 is a database of pre-negotiated purchase orders (POs) that are open and instantly fillable such that the UME Gateway may choose to instantly complete a sales transaction for any medical device, part, or accessory according to the predefined terms and conditions of the PO any time a single item that matches demand on the PO becomes available.

The Fillable at Quantity or Lotted/Combined container 542 is a database of pre-negotiated purchase orders (POs) that are open and automatically fillable by the UME Gateway only when the UME Gateway has supply necessary to combine multiple products together to meet minimum quantities or combinations of products a buyer specifies in a PO.

If the minimum required product combinations are available the UME Gateway may choose to instantly complete a sales transaction for that combination or lotting of medical devices, parts and/or accessories according to the predefined terms and conditions of the PO.

The Firm Requests and Quotes container 543 is a database where very detailed, but nonbinding requests or quotes that include the major proposed terms and conditions for buying specific medical equipment are catalogued. The UME Gateway can facilitate converting matching supply into sales transactions via AI or human agent communications with the buyer but cannot automatically legally do so or fill this type of demand.

The Active Inquiry container 544 is a database where a buyer's active demand for specific makes and models of products that might become available from the UME Gateway are catalogued, but this demand does not contain specific negotiated details from the buyer as to quantities, price points, timing conditions, and other key terms. The UME Gateway can still match supply against this type of registered demand and alert the buyer and stakeholder of availability of supply to allow the parties to negotiate specific, fillable sales transactions for matched items.

The General Registered Interests container 545 is a database where general registered product interests from buyers are catalogued by product type, brand, family, or other general information, but no specific details as to makes, models, conditions, specifications, accessories, or other information is available to precisely match supply against. For example, a buyer may express general interest in infusion pumps. The UME Gateway can still match supply against this type of general registered demand and alert the buyer and other stakeholders of availability to allow them to attempt to negotiate sales transactions on specific items via communication with UME Gateway controlled AI or human agents.

The Demand Harmonization engine 546 operates to harmonize the various demand formats submitted from buyers into the UME Gateway's compatible nomenclature and then enriches the data to allow the AI models, business process orchestrations, and other analytics and automations to work off the buyer's active registered demand.

The Demand Change or Cancel engine 547 determines whether any new, harmonized, and enriched demand information from a buyer entering the Active Registered Demand Module group 530 represents new demand, changed demand which can be in the form of added or decreased quantities or changes in other product specific details or transaction terms, or a cancellation of open registered demand.

The Demand Expiration Monitor engine 548 monitors existing active registered demand from the Demand Data Containers subgroup 540 to see if any of the records are approaching expiration so proactive action can be taken in conjunction with the Buyer Expiration Alert and Response Monitor step 552 and the Renew, Change, Cancel step 551. Demand expiration dates can be based on a need by timeframes communicated by a buyer, contract, or PO terminations or stated end dates, or by other means where the UME Gateway automatically determines a demand record needs reconfirmed or cancelled based on the age, nature, products, pricing, and market conditions associated with that demand record.

The Buyer Expiration Alert and Response Monitor step 552 alerts a buyer when any portion of their registered demand is approaching expiration as determined by the Demand Expiration Monitor engine 548. The alert methods can be configured by a buyer to include email, SMS messages, phone calls, mobile app notifications, and/or web portal notifications, and the alert includes options for the buyer to provide responses so they can extend the expiration dates on items still needed, propose new prices, quantities, and other terms associated with their demand, add additional needed items, allow their demand to expire, and/or make other changes. Responses are automatically captured and passed to the Renew, Change, Cancel step 551 for processing.

The Renew, Change, Cancel step 551 is a step in which any buyer responses from the Buyer Expiration Alert and Response Monitor step 552 is processed and applied against the active registered demand so that the active registered demand databases reflect the updated accurate details related to products, pricing, quantities, and other terms. If a buyer fails to respond, any expiring demand is moved to an expired status on its expiration date and removed from the Demand Data Containers subgroup 540 and the Active Registered Demand database 232.

The Buyer Self-Service Systems capability 550 includes all portals, mobile apps, web sites, messaging systems, and AI or human customer service agents available directly from the UME Gateway or via third-party channels which a buyer can interact with to submit surveys, update profiles, or communicate new or updated demand information to the UME Gateway. Some of these systems may also allow buyers to shop or take other actions as it relates to the UME Gateway.

The Buyer Shopping Agents engine 560 takes outputs from the Active Registered Demand Module group 530 and converts them into automations and data that run in near real-time monitoring the UME Gateway's ever-changing supply of medical equipment and automatically informs a buyer when demanded products become available to them. This allows buyers to have near real time awareness of newly available medical equipment they are interested in without buyers themselves having to spend time and resources repeatedly searching for, inquiring about, or being made aware of the medical devices, parts and accessories that are being added to the UME Gateway on an ongoing basis. The alerts can be surfaced in the Buyer Self-Service Systems capability 550 or configured by buyers to be sent via SMS, email, or other messaging methods.

The Demand Response Plans group 570 is a group of potential actions that can be recommended by the reFramer™ AI Econometric Evaluation Engine 120 be taken on available medical equipment in the UME Gateway which matches buyer demand. Since a specific piece of medical equipment can be sold only once the goal is to pursue the recommended demand response plans in order of priority so the UME Gateway can generate the best overall outcomes for the healthcare system or asset owner of the medical equipment as well as overall buyer needs.

The Fill Open PO Order response 571 is a response to the demand response plan generated by the reFramer™ AI Econometric Evaluation Engine 120 in which an open PO order is filled, and an automatic sale transaction is processed with no additional intervention or negotiations.

The Hold and Accumulate response 572 is a response to the demand response plan generated by reFramer™ AI Econometric Evaluation Engine 120 in which inventory is held and accumulated in order to fill an open PO or other firm demand at a later time once all conditions for minimum quantities or product lotting and kitting combinations are met. As examples a patient monitor might be held until compatible working batteries and requested modules are also available, or an infusion pump might be held until the UME Gateway has at least twenty of the same make and model available because an open PO or other firm demand requires all items to complete the transaction.

The Send Custom Offers response 573 is a potential demand response plan generated by the reFramer™ AI Econometric Evaluation Engine 120 in which custom offers about available supply are sent to buyers based on their tier level. This may occur if an immediate automated transaction for a piece of medical equipment does not take place. By tiering buyers the better and more active participants of the UME Gateway are given earlier access and opportunities to purchase available supply and if, after time passes and no transaction occurs, new offers are prepared and automatically sent from the UME Gateway to the next tier of buyers with the cycle automatically repeating until the supply is no longer available or all buyers in all tiers have passed on the supply.

The Alert Availability response 574 is a demand response plan action generated by the reFramer™ AI Econometric Evaluation Engine 120 in which buyers are alerted to the availability of a given piece of medical equipment, but no specific offer or buyer priority is made. This general availability communication allows all buyers to connect to the UME Gateway in their preferred manner and attempt to procure items in which they are interested.

The Lotting and Kitting response 575 is a response to the demand response plan generated by the reFramer™ AI Econometric Evaluation Engine 120 in which a piece of medical equipment is recommended to be lotted or kitted with other supply in the UME Gateway in order to communicate availability of newly converted and combined sets of products through the Send Custom Offers response 573 or Alert Availability response 574 with the analytics showing this investment in time will lead to a better outcome. The items may first be combined, rephotographed, and merchandised as a new unit via the Supply Transfer and Consolidation Work Orders step 580 before the communication takes place.

The Supply Transfer and Consolidation Work Orders step 580 is a step in which work orders are automatically generated from the Lotting and Kitting response 575 in order for the physical supply to be transferred to a single location, the actual lotting and kitting consolidation to take place, and the lot or kit to be photographed and presented for sale.

The Tiered Offers group 590 is an automated prioritization and sequencing method for promoting custom offers for UME Gateway supply to buyers with known active demand giving earlier access and opportunities to purchase available supply to the buyers the reFramer™ AI Econometric Evaluation Engine 120 determines is most beneficial and later adding opportunities to other buyers as time passes and no transaction occurs.

The Tier 1 Offers list 591 is a list of the most valuable buyers in the UME Gateway for a specific piece of medical equipment at the time it is available.

The Tier 2 Offers list 592 is a list of the next most valuable buyers in the UME Gateway underneath those in the Tier 1 Offers list 591 for a specific piece of medical equipment at the time it is available.

The Tier 3 Offers list 593 is a list of the next most valuable buyers in the UME Gateway underneath those in the Tier 1 Offers list 591 and the Tier 2 Offers list 592 for a specific piece of medical equipment at the time it is available.

The Tier 4 Offers list 594 is a list of the next most valuable buyers in the UME Gateway underneath those in the Tier 1

Offers list 591, the Tier 2 Offers list 592, and the Tier 3 Offers list 593 for a specific piece of medical equipment at the time it is available.

The flow of the UME Gateway Active Registered Demand Module and Demand Response Plans flowchart 500 is described herein. The Equipment Acquisition process 110 brings new medical equipment into the UME Gateway where the Equipment Identification and Evaluation process 111 ensures the relevant photos and information about that medical equipment inventory are captured and made available to the reFramer™ AI Econometric Evaluation Engine 120 to make recommendations regarding the disposition of that medical equipment. Any known active demand in the Active Registered Demand database 232 or as prioritized and determined by the reFramer™ AI Econometric Evaluation Engine 120 is communicated to the Equipment Acquisition process 110 to prioritize sourcing of the most needed medical equipment to meet demand. The reFramer™ AI Econometric Evaluation Engine 120 continuously evaluates current UME Gateway inventory availability against information in the Active Registered Demand database 232 as one factor in making recommendations. Specifically, the reFramer™ AI Econometric Evaluation Engine 120 performs AI based matchmaking of to see if currently available inventory can be used to meet known active demand either as-is or though lotting, kitting, reconditioning, or parts harvesting of available medical equipment using its Supply and Demand Match Analytics engine 512. The Supply and Demand Match Analytics engine 512 consults the Digitized Business and Contract Rules and Constraints database 190 to ensure all buyer relevant contract terms and conditions can bet met when making demand matches and tags the demand match records with those terms and conditions. Simultaneously the reFramer™ AI Econometric Evaluation Engine 120 employs AI models and automations in the Buyer Product Segmentation and Tiers engine 514 to prioritize which buyers with active demand to consider responding to, at what price and in what order to maximize returns on UME Gateway medical equipment inventory without overselling constrained supply. Both steps feed their results into other AI models in the reFramer™ AI Econometric Evaluation Engine 120 which ultimately makes recommendations on escape paths and pricing for available UME Gateway medical equipment. Where the reFramer™ AI Econometric Evaluation Engine 120 recommends allocating inventory to respond to known active demand it will produce one or more detailed demand response plans as shown in the Demand Response Plans group 570. The five responses include the Demand Response Plans group 570 are the Fill Open PO Order response 571, the Hold and Accumulate response 572, the Send Custom Offers response 573, the Alert Availability response 574, and the Lotting and Kitting response 575. If the Fill Open PO Order response 571 is chosen an automated transaction will immediately occur and ownership of the inventory will be transferred to the buyer of that open PO. If the Hold and Accumulate response 572 is chosen, inventory will be held in the UME Gateway and prevented from being sold, marketed or otherwise disposed of as the reFramer™ AI Econometric Evaluation Engine 120 AI predicts additional compatible inventory will come in that can be combined with the held inventory to generate sufficient quantities, combinations, lots or kits to meet known demand before it expires and fill an open PO. At any time, the reFramer™ AI Econometric Evaluation Engine 120 can reverse a hold decision and recommend a different demand response plan or escape path alternative for a piece of medical equipment if the known demand changes or market conditions warrant. If the Send Custom Offers response 573 is chosen the recommendations of the Buyer Product Segmentation and Tiers engine 514 will be passed to the Tiered Offers group 590 where automations will send the buyer specific offers to the first tier of buyers in the Tier 1 Offers list 591. If no transaction occurs after a certain amount of time buyer specific offers will be sent to buyers in the Tier 2 Offers list 592, and later the Tier 3 Offers list 593, and later still the Tier 4 Offers list 594. At any time, the reFramer™ AI Econometric Evaluation Engine 120 AI models can choose to revise and send new offers to buyers in any tier or reverse the Send Custom Offers 573 choice and end offers that have been sent in order to move the inventory to a different demand response plan or escape path. If the Alert Availability response 574 is chosen general availability of that medical equipment is communicated to all buyers with known active demand with no regard to special pricing or sequencing through whatever approved communication methods they have provided to the UME Gateway. If sufficient active registered demand and supply exists to warrant the Lotting and Kitting response 575 be chosen, the Supply Transfer and Consolidation Work Orders step 580 is taken to lot and kit the inventory into a new inventory items which then goes through the Equipment Identification and Evaluation Process 111 so they can be made available to reFramer™ AI Econometric Evaluation Engine 120 for matching to active registered demand. The Active Registered Demand database 232 is being continuously updated to support the above processing as follows. The Buyer Demand Registration process 529 captures information communicated from buyers via surveys and forms directly completed by the buyer using UME Gateway integrated portals, web sites and mobile apps in the Buyer Self-Service Systems capability 550, or via buyer phone calls and messaging with UME Gateway AI or human customer service agents. Depending on the nature and specificity of the information provided by the buyer as to product details, quantity, timelines, terms, and other transaction related factors the information from the Buyer Demand Registration process 529 is automatically entered into either the Negotiated Open PO Orders database 521, the Buyer Quotes and Offers database 523, the Registered Interest Makes and Models database 525, and/or the Purchase Inquiries database 527 as applicable. The Demand Harmonization engine 546 ingests the data from the Negotiated Open PO Orders database 521, the Buyer Quotes and Offers database 523, the Registered Interest Makes and Models database 525, and the Purchase Inquiries database 527 and converts it into the taxonomy and format needed by the UME Gateway and determines the type and specificity of the demand. The Demand Change or Cancel step 547 receives this harmonized demand information from the Demand Harmonization engine 546 and determines if it represents new demand, changed demand in terms of products, quantities, pricing, terms, or other factors, and/or cancelled demand, and then sends the appropriate record additions or updates to the Demand Data Containers subgroup 540. Based on the type of demand determined by the Demand Harmonization engine 546, the Demand Change or Cancel step 547 will update either the Instantly Fillable/Open POs container 541 if a transaction can be processed for a matching piece of UME Gateway medical equipment inventory with no additional requirements, the Fillable at Quantity or Lotted/Combined container 542 if a transaction can be completed for a matching piece of UME Gateway medical equipment inventory provided other inventory is also available to meet the conditions of demand, a Firm Requests and Quotes container 543 which requires final negotiation and completion of sale for a transaction to occur, an Active Inquiry container 544 which is specific as to immediate product interest but missing key terms and details such as to potential product pricing, conditions, specifications and accessories, and a General Registered Interests container 545 which contains high level interest form buyers to be informed when certain types, makes, or models of medical equipment are available. Information from these demand containers in the Demand Data Containers subgroup 540 is periodically pushed into the Active Registered Demand database 232 for use as described above and in other parts of the UME Gateway. The Demand Expiration Monitor engine 548 is continuously monitoring the datasets in the Demand Data Containers subgroup 540 to detect when any demand is expiring due to dates set by buyer, termination of buyer contracts, passage of time, and/or changing market conditions and informing the Buyer Expiration Alert and Response Monitor step 552 to communicate the upcoming expiration to the buyer. The communications to the buyer include a method to respond back to the Buyer Expiration Alert and Response Monitor step 552 as to whether they want to extend, change, or cancel the expiring demand and the Renew Change or Cancel step 551 will alert the Demand Change or Cancel step 547 which will process the necessary changes. At any time, a buyer may use the Buyer Self-Service Systems capability 550 to update expiring or other demand information in the UME Gateway and/or trigger changes to the Buyer Shopping Agents engine 560. The Buyer Shopping Agents engine 560 generates alerts for all UME Gateway offers or inventory specifically made available to that buyer, and/or uses AI to match the buyer's demand records to all generally available UME Gateway inventory and inventory sourcing opportunities. These alerts generated by the Buyer Shopping Agents engine 560 are made visible through the Buyer Self-Service Systems capability 550 or can be sent through any SMS, email, mobile app alerting, or other messaging method the buyer prefers. The Buyer Shopping Agents engine will also generate alerts when either the Alert Availability response 574 is given or when an offer from the Tiered Offers group 590 is offered.

The Supply and Demand Match Analytics engine 512 features of the reFramer™ AI Econometric Evaluation Engine 120 uses AI and other analytics methods to repeatedly evaluate rapidly changing available medical equipment inventory against known active buyer demand to provide options to consider when recommending escape paths and pricing for that equipment. These options can be direct matches or require existing inventory to be lotted, kitted, reconditioned, and/or harvested for parts in order to match known demand. These analytics may also optimize maximizing the net return on each individual piece of medical equipment against a slightly lower return for a single asset that is simultaneously made available or purchased with other assets in the same transaction thereby increasing the overall return to the UME Gateway. The Supply and Demand Match Analytics engine 512 also applies all known relevant channel terms, product terms, fulfillment terms, minimum fill quantities, condition and specification requirements, warranties and any special buyer agreements found in the Digitized Business and Contract Rules and Constraints database 190 that relate to the demand and passes them to other reFramer™ AI Econometric Evaluation Engine 120 AI models which evaluate the economic viability and profitability prior to recommending matching any inventory to demand. Automated predictions are also made as to the likelihood pursuing a supply/demand match will result in an actual transaction and are factored into confidence intervals associated with the recommendations. This ensures supply and demand matches are only pursued when they represent the best escape path option and generate the best outcome for the healthcare system or asset owner.

Since the secondary market for medical devices is highly fragmented and constrained by unpredictable supply, buyers who recondition and resell patient-ready equipment or provide parts harvesting and testing services must constantly scour multiple vendors hunting for availability of the specific assets they need. Often buyers miss out on equipment which was sold to someone else right before they checked for its availability, or potentially comes in stock shortly after their search. Similarly, just one hospital closure or healthcare system's and/or asset owner's fleet conversion can lead to an immediate spike in supply that is difficult to quickly generate demand for organically. The UME Gateway solves these procurement and timing challenges by allowing buyers to register demand for specific devices, conditions, specifications, quantities, completeness, and other factors relevant specifically to used medical equipment. This pre-registered demand and interest management enables buyers to offload their procurement responsibilities to the UME Gateway. Simultaneously, to the degree the UME Gateway has access to a healthcare system or asset owner's CMMS records it can predict and notify buyers of potential upcoming supply well before the medical equipment is actually released to the UME Gateway for disposition.

The UME Active Registered Demand and Demand Response Plans feature transforms the downstream reverse supply chain for medical devices by providing buyers with automated self-service procurement tools that can be used by the reFramer™ AI Econometric Evaluation Engine 120 and the disposition process orchestrations to automate supply and demand matching and determine if the match should be pursued as the best escape path. This results in faster disposition and yields more value for healthcare systems and/or asset owners while ensuring buyers do not miss out on desired assets due to their own timing and procurement resource limitations.

Demand can be registered as a binding open purchase order commitments with pre-negotiated pricing, terms, conditions and expiration dates or as non-binding quotes or even simple expressions of product interest. The UME Gateway is able to partition these types of demand into different datasets and act upon the demand information to the extent of the information available in each demand type. This registered demand then acts as a software buying agent representing a buyer allowing the UME Gateway to identify matches on inventory that is available to that buyer. Software agents in the UME Gateway can also use registered demand to recommend and present buyers with offers for compatible or alternative manufacturers or model numbers where quantity is available to generate interest in other medical devices and increase resale value for other medical devices. This automated communication to buyers of changing supply available to them provides significant time and cost savings to their procurement process.

When demand matches are made for UME Gateway medical equipment inventory the reFramer™ Econometric Evaluation Engine 120 then performs an economic assessment and recommends whether to automatically allocate and process a pre-negotiated sale, hold and accumulate assets for registered orders that require preset volume thresholds or combinations which it predicts can be met, present buyers with customized offers to purchase at an acceptable price, simply alert buyers of availability for their personnel to follow up and compete for the asset if interested, create a new product by lotting or kitting the medical equipment with other inventory that is in higher demand, or pursue alternative disposition escape paths entirely.

The UME Gateway provides self-service portals, web sites, and mobile apps as well as AI and human customer service agents to enable buyers to easily register their specific product interests and demand. These same self-service capabilities can be used to update demand information by adding, changing, or canceling requests, as well as receive and easily respond to automated alerts about expiring demand that they wish to keep active. AI converts all captured buyer input into content and formats useable by the UME Gateway via the Demand Harmonization engine 546, partitions it by type, and ultimately updates the Active Registered Demand database 232 that is used for multiple purposes throughout the UME Gateway.

Because of the high risk of stock outs and overselling scarce medical equipment supply the UME Gateway is able to segment and prioritize buyers into tiers to sequence which customers are notified about product availability and when. These segments and tiers are created in the reFramer™ AI Econometric Evaluation Engine 120 by the AI capabilities of the Buyer Product Segmentation and Tiers engine 514 considering all active registered demand, product interests as well actual historical purchase behavior of UME Gateway buyers. By considering both stated intent and actual behavior the AI predictive models of whether matched demand is likely to result in a profitable transaction for medical equipment inventory are much more accurate. Once buyers are segmented and clustered into tiers, medical equipment inventory is then made available through marketing automation tools to the most valuable buyer tiers first. Over time slow moving assets can be released to less valuable segments and tiers to attempt to generate at least a minimal return prior to considering donation or recycling escape paths.

FIGS. 6a and 6b schematically present a UME Gateway Multi-Channel Optimization flowchart 600, showcasing how the UME Gateway's capabilities to maximize exposure and provide more buyers access to medical equipment operates. The UME Gateway Multi-Channel Optimization flowchart 600 includes the Equipment Identification and Evaluation process 111 found in FIG. 1a, the Digitized Business and Contract Rules and Constraints database 190 found in FIG. 1a, the reFramer™ AI Econometric Evaluation Engine 120 found in FIG. 1a, a Channel Listing and Promotion Optimization Capabilities group 610 within the reFramer™ AI Econometric Evaluation Engine 120, the Channel Options, Terms and Constraints database 238 found in FIG. 2b, a Channel Market Device Restrictions database 612, a Channel Historical Product and Market Factors database 613, a Marketing Automation Direct Customer Communications engine 617, a Virtual Lotting and Kitting engine 618, a UME Gateway/Channel Controller and Nomenclature Translations engine 630, a Channel Specific Listing Template Generator 631, a Time Based Discount Schedules engine 633, a Channel Based Offer Response Calculator 635, a Channel Offer Negotiation step 637, a Resell Channels group 640, a Channel Options, Terms and Constraints Configurations database 647, a Buyer Specific Profiles and Discount Tiers database 649, a Channel Inventory Holds Processing engine 650, an Order Fulfillment group 660, a Virtual Lotting and Kitting Reversals and Fulfillment Splits engine 668, a UME Gateway Order Ingestion Processing engine 670, an AI Assisted Returns/Discounts/Credits Optimizer 680, a Returns Processing process 682, and the Financial Postings and Reconciliation Engine 180 found in FIG. 1*b*.

The Channel Listing and Promotion Optimization Capabilities group 610 includes a Channel Analytics engine 614 and a Current Channel Inventory Dataset 615.

The Resell Channels group 640 includes a UME Gateway Controlled Channels set 641, a 3*rd* Party Medical and Industrial Equipment Marketplaces set 643, and a 3*rd* Party Auction Channels set 645.

The Order Fulfillment group 660 includes a Fulfilment Shipping, Onsite Pickup, or Drop-Ship process 661, a Fulfillment Packing and Palletizing step 663, a Time or Accumulation Thresholds Reached engine 665, and a Buy and Hold/Order Accumulation and Consolidation process 667.

The Equipment Identification and Evaluation process 111 is the same as described in FIG. 1*a* and is the process by which image processing is combined with AI and other techniques to efficiently identify makes, models, conditions, system completeness, specifications, included accessories, and other basic information about medical equipment to feed into subsequent analysis, databases, and automations that can be processed by the UME Gateway. Once the basic information is known, the information about current available inventory is sent to the reFramer™ AI Econometric Evaluation Engine 120 where among other things it can recommend the best channels and pricing to list inventory designated for resale.

The Digitized Business and Contract Rules and Constraints database 190 is the same as described in FIG. 1*a* and contains among other things healthcare system and asset owner commitments and other terms and conditions that need to be considered when deciding which channels the UME Gateway may place their products in, as well as the pricing and fulfillment options necessary to meet their requirements. This database is also consulted for contract terms to perform required financial settlements and postings as transactions occur in the multi-channel resale channels via the Financial Posting and Reconciliation Engine 180 found in FIG. 1*b*.

The reFramer™ AI Econometric Evaluation Engine 120 which is the same as described in FIG. 1*a* contains AI capabilities to match available UME Gateway medical equipment inventory designated for resale to the specific channels it predicts that inventory will sell in as well as the timeframe and pricing most likely to lead to a successful sale. These capabilities are detailed in the Channel Listing and Promotion Optimization Capabilities group 610.

The Channel Listing and Promotion Optimization Capabilities group 610 within the reFramer™ AI Econometric Evaluation Engine 120 uses AI models and automations to perform, among other things, the matching of available medical equipment inventory to the specific channels they should be listed in, the appropriate pricing, discounts, promotions, and negotiation strategies to employ for those products in each selected channel, when to present individual pieces of medical equipment inventory as virtual lots or kits within a channel, and when to remove or update product listings.

The Channel Analytics engine 614 is a set of AI models that continuously monitor UME Gateway available medical equipment inventory designated for resale and assigns the inventory to and from the channels it believes will be most effective in reaching buyers at that point in time as well as generating channel specific virtual merchandising, pricing, promotion, and negotiation plans for those products in a format that can be acted upon by other UME Gateway automations. These analytics consider information in the Digitized Business and Contract Rules and Constraints database 190, the Channel, Fee, Payment and Fulfillment Capabilities database 238, the Channel Market Device Restrictions database 612, and the Channel Historical Product and Market Factors database 613 to determine what is allowable, what has been successful in the past, and what will be the final net profitability for any given product listing in each channel it is assigned to.

The Current Channel Inventory Dataset 615 is continuously updated by the Channel Analytics engine 614 augmenting UME Gateway medical equipment inventory records with all relevant channel assignments, pricing and related information produced by the Channel Analytics engine 614 for automated processing by other AI models and automations in the UME Gateway.

The Channel Options, Terms and Constraints database 238 is the same as described in FIG. 2*b* and is a database of all channels which the UME Gateway participates in, the types of products typically sold in that channel, any specific types of products that are prohibited by that channel, the buyer segments and geographic areas the channel reaches, the payment and fulfillment methods the channel supports, the costs and fees associated with listing, selling, and fulfilling orders in that channel, and other information that can assist the reFramer™ AI Econometric Evaluation Engine 120 in deciding whether to place a piece of medical equipment in a given channel and at what price point to account for the channel's selling and fulfillment terms.

The Channel Market Device Restrictions database 612 is a database of the specific types and brands of medical devices restricted for sale in certain channels either in whole or conditionally in terms of restrictions for certain countries or markets. These restrictions may be set by the channels themselves, the manufacturers of the medical equipment, the UME Gateway itself due to past experience, or other third-party regulations.

The Channel Historical Product and Market Factors database 613 is a database of how channels have previously performed including listing times, sales prices, discounts, returns, and post order processing exceptions for certain types, makes and models of products. It informs the Channel Analytics engine 614 regarding channels to prefer or avoid for specific types of medical devices based on experience.

The Marketing Automation Direct Customer Communications engine 617 is a set of AI assisted automations that trigger communications to potential buyers notifying them of any new or updated product listings or pricing they might be interested in as well as links to find those products in the channels they prefer.

The Virtual Lotting and Kitting engine 618 is technology that enables the UME Gateway to present individual medical equipment inventory items as a combined lot or kit to buyers in one or more channels for their shopping and buying convenience without actually performing physical lotting or kitting of the items. This works in conjunction with the Virtual Lotting and Kitting Reversals and Fulfillment Splits engine 668 when a buyer purchases virtually lotted and kitted items.

The UME Gateway/Channel Controller and Nomenclature Translations engine 630 works to translate information about products, orders, and fulfillments the UME Gateway sends to third-party resale channels into formats those channels uniquely understand and require, as well as translates information received from the third-party resales channels into structures the UME Gateway requires for processing.

The Channel Specific Listing Template Generator 631 formats UME Gateway product data that was translated by the UME Gateway/Channel Controller and Nomenclature Translations engine 630 into the specific listing formats and presentations required to present the products in a given channel.

The Time Based Discount Schedules engine 633 is an automation that periodically reviews listings in each channel on a scheduled basis and automatically applies any current UME Gateway designated discounts to those listings based on the channel and how long the items have been listed without being sold.

The Channel Based Offer Response Calculator 635 is an AI model that analyzes buyer offers to determine the overall predicted post fulfillment profitability of completing a transaction for the set of medical equipment proposed by the buyer at that time along with what minimally acceptable and target pricing should be for those products if sold in the channel the offer was made.

The Channel Offer Negotiation step 637 is a step that can be automatically performed by AI or by a human actor to respond to a given buyer offer in a given channel. Based on the results of the Channel Based Offer Response Calculator 635 an offer can be automatically accepted or rejected or a counterproposal made to the buyer through the channel.

The Resell Channels group 640 is the set of online channels, apps, and marketplaces UME Gateway products are made available for purchase. The Resell Channels group 640 is also a group of both UME Gateway controlled and third-party resale channels available on the UME Gateway to list products and services for sale. The design of the UME Gateway allows for channels to be easily added to increase exposure of UME Gateway products and make it easier for buyers to find UME Gateway products in their preferred buying channel.

The UME Gateway Controlled Channels set 641 are channels owned and operated by the UME Gateway itself including online portals, mobile apps, direct sales agents, and authorized reseller networks.

The 3$^{rd}$ Party Medical and Industrial Equipment Marketplaces set 643 is a set of various industry marketplaces the UME Gateway can automatically offer and sell products in around the world with each specializing in different types of products and categories.

The 3$^{rd}$ Party Auction Channels set 645 is a set of third-party auction channels UME Gateway products may be listed in and with those listings and sales subject to special government regulations for auctions as well as the particular bidding rules and capabilities set by the auction channel. UME Gateway products listed in these channels are placed under additional restrictions while auction bidding is underway as a result and any sales, payment processing and fulfillment is performed by the UME Gateway in compliance with the regulations.

The Channel Options, Terms and Constraints Configurations database 647 is used to configure the allowable options and settings that control fees, allowable payment methods, allowable fulfillment and shipping methods, return policies, fulfillment requirements, and the resulting charges in each channel.

The Buyer Specific Profiles and Discount Tiers database 649 is a database that tells one or more channels whether buyers are charged different types of taxes or fees, and what discounts a buyer may be automatically entitled to in that channel based on their profile status (for example a certified nonprofit) or their past purchase history tier in that channel.

The Channel Inventory Holds Processing engine 650 is a feature that informs different parts of the UME Gateway when a buyer has an in-process order for a one or more pieces of medical equipment inventory to prevent other parts of the UME Gateway from otherwise selling or moving that medical equipment inventory into a different escape path.

The Order Fulfillment group 660 is a set of activities to transfer products purchased in a channel to the buyer in a manner most efficient for and preferred by the buyer.

The Fulfilment Shipping, Onsite Pickup, or Drop-Ship process 661 is a process where purchased products are shipped directly from a UME Gateway location to a location a buyer chooses, drop-shipped from a healthcare system or asset owner location to a location a buyer chooses, or picked up directly by the buyer.

The Fulfillment Packing and Palletizing step 663 is a step where medical devices are prepared for shipment in a specialized manner to protect the sensitive nature of the instruments and equipment involved.

The Time or Accumulation Thresholds Reached engine 665 is an automation that tracks how long the UME Gateway is holding purchased products for a buyer while waiting for them to arrange shipment or pickup of the items, and ultimately can lead to items being placed in storage or considered abandoned after timeframes designated at purchase.

The Buy and Hold/Order Accumulation and Consolidation process 667 is a process where orders are held from shipping for a period of time by agreement from the UME Gateway in order to consolidate multiple orders into one single shipment or group of shipments or otherwise for the convenience of the buyer.

The Virtual Lotting and Kitting Reversals and Fulfillment Splits engine 668 translates any virtually lotted or kitting sales from a channel back into the specific pieces of inventory the virtual lot or kit included so the items can be fulfilled and accounted for correctly.

The UME Gateway Order Ingestion Processing engine 670 is an automation that processes orders received by the UME Gateway after they have been translated to the UME Gateway formats by the UME Gateway/Channel Controller and Nomenclature Translations engine 630 and ensures the orders are processed according to UME standards so they can be fulfilled and accounted for.

The AI Assisted Returns/Discounts/Credits Optimizer 680 is an AI model that addresses order exceptions and proposes the financially best outcome for the UME Gateway to resolve whether by refunding a customer in whole or in part and/or requiring items to be returned or allowing them to be kept by a customer because of the high logistics cost to ship them back.

The Returns Processing process 682 tracks items expected to be returned to the UME Gateway as a result of an order exception to ensure they are received back and re-inventoried for processing prior to issuing any discounts or refunds.

The Financial Posting and Reconciliation Engine 180 which is the same as described in FIG. 1*b* processes all completed sales, refunds, discounts, and credits for the UME Gateway to have accurate financial accounting integrity and reporting. It applies postings to healthcare systems and asset owners' ledgers for their share of all sales and credits based on their agreements and rules for the channel each sale took place as specified in the Digitized Business and Contract Rules and Constraints database 190.

The flow of the UME Gateway Multi-Channel Optimization flowchart 600 is described herein. Currently available UME Gateway medical equipment from the Equipment Identification and Evaluation process 111 is continuously evaluated by the reFramer™ AI Econometric Evaluation Engine 120, and any equipment recommended for as-is or merchandised reselling escape paths is processed by the Channel Listing and Promotion Optimization Capabilities group 610. The Channel Analytics engine 614 applies AI in considering information about UME Gateway channels in the Channel Options, Terms and Constraints database 238, the Channel Market Device Restrictions database 612, and the Channel Historical Product and Market Factors database 613, along with any relevant requirements or constraints in the Digitized Business and Contract Rules and Constraints database 190, to assign the medical equipment inventory to one or more channels for sale. The Channel Analytics engine 614 further considers current channel performance for products such as the level of product interest and views, number of watchers, and frequency of offers for products currently listed in channels and then determines recommended methods for channel-based promotions, pricing, and discounting the inventory at the current time to seek the best resale outcome. The Channel Analytics engine 614 passes this information along with the channel assignments to the Current Channel Inventory Dataset 615 where the Marketing Automation Direct Customer Communications engine 617 executes direct communication to recommended buyers informing them of the latest product and pricing availability and directing them to one or more preferred channels to see the listings. Updates to the Current Channel Inventory Dataset 615 are pushed to the UME Gateway/Channel Controller and Nomenclature Translations engine 630 which converts all UME Gateway product listing and promotion data into formats consumable by the resale channels. If necessary, the Current Channel Inventory Dataset 615 updates will first pass through the Virtual Lotting and Kitting engine 618 to digitally combine items for sale in a single listing even though they remain physically separate and distinct, before passing them to the UME Gateway/Channel Controller and Nomenclature Translations engine 630. Converted listing data from the UME Gateway/Channel Controller and Nomenclature Translations engine 630 is pushed through the Channel Specific Listing Template Generator 631 which generates the new or updated channel specific listings (or tags current listings for removal) and then passes the results to the relevant channels in the Resell Channels group 640 for each channel to perform applicable adds, updates, or listing removals. The UME Gateway/Channel Controller and Nomenclature Translations engine 630 may also send channel product and customer promotion schedules to the Resell Channels group 640 directly. The UME Gateway/Channel Controller and Nomenclature Translations engine 630 also sends information from the channels regarding channel product interests and watcher and offer activities to the reFramer™ AI Econometric Evaluation Engine 120 for processing. All UME Gateway controlled and third-party channels in the Resell Channels group 640 operate autonomously to present listings to potential buyers, provide customer service, and execute channel-based promotions and pricing changes according to rules setup in the Channel Options, Terms and Constraints Configurations database 647 and the Buyer Specific Profiles and Discount Tiers database 649. As buyers make offers on products within the various channels the Channel Based Offer Response Calculator 635 receives them and uses AI models to calculate desired and minimally acceptable outcomes for automated or human agents to send an offer acceptance, counter, or rejection back to the buyer via the channel in the Channel Offer Negotiation step 637. A Time Based Discount Schedules engine 633 runs autonomously and periodically makes pricing changes to applicable listings that have not sold in a given timeframe and is also considered by the Channel Based Offer Response Calculator 635 in its calculations. The Time Based Discount Schedules engine 633 may also send information regarding discounts to the Channel Specific Listing Template Generator 631 for inclusion with listings generated in a channel using information from the UME Gateway/Channel Controller and Nomenclature Translations engine 630. Any interest or offer activity, along with any pending, closed, or cancelled orders or order exceptions happening in the Resale Channels group 640 are passed by the channel to the UME Gateway/Channel Controller and Nomenclature Translations engine 630 which converts the information and passes it to the Channel Inventory Holds Processing engine 650, the UME Gateway Order Ingestion Processing engine 670 and/or the Fulfillment Group activities 660 as applicable in formats they can process. The Channel Inventory Holds Processing engine 650 will inform the reFramer™ AI Econometric Evaluation Engine 120 to add or remove holds on current UME Gateway inventory related to pending or cancelled orders as applicable so the reFramer™ AI Econometric Evaluation Engine 120 can ensure held items are pulled from other channels and blocked from other escape path processing and released holds allow the impacted inventory to have channel assignments and escape path recommendations reconsidered. The Fulfillment Group activities 660 will receive information on cancelled orders from the Channel Inventory Holds Processing engine 650 in order to cancel any pending fulfillment activities and restock items as necessary. The Fulfillment Group activities 660 also receives information regarding business and contract rules and constraints from the Digitized Business and Contract Rules and Constraints database 190 to ensure that any orders that are fulfilled are done in a compliant manner. The UME Gateway Order Ingestion Processing engine 670 will create fulfillment instructions and work orders that include the performance requirements and turnaround times specific to each channel and order and pass them to the Order Fulfillment group 660 activities for closed orders. Any orders containing virtually lotted or kitted items will first pass through the Virtual Lotting and Kitting Reversals and Fulfillment Splits engine 668 so the UME Gateway can convert the order back into the individual serialized inventory items in order to provide specific fulfillment instructions for the Order Fulfillment group 660 activities and allocation information to the Financial Posting and Reconciliation Engine 180 to properly credit healthcare systems and/or asset owners providing inventory sold in a virtual lot or kit. Activities in the Order Fulfillment Group 660 can then be performed to package and ship, dropship, or hold and combine purchased inventory with future orders according to the buyer's instructions offering them cost savings and convenience through flexible fulfillment schedules. The Time or Accumulation Thresholds Reached engine 665 is an automation that tracks unfilled orders and sends UME Gateway alerts to buyers that their items are awaiting shipment or pickup, or, if the Buy and Hold/Order Accumulation and Consolidation process 667 is utilized, may be placed in storage or considered abandoned after timeframes designated in the channel listing agreement are reached. If necessary, the Fulfillment Packing and Palletizing step 663 will be performed to pack up and/or palletize the medical equipment for shipment or storage. Once orders are shipped or picked up the Order Fulfillment Group activities 660 will send fulfillment information to the Financial Posting and Reconciliation Engine 180 for revenue recognition and back to the appropriate resell channel via the UME Gateway/Channel Controller and Nomenclature Translations engine 630 so the channel can inform the buyer and provide a tracking number. Any order exceptions passed from the UME Gateway/Channel Controller and Nomenclature Translations engine 630 to the UME Gateway Order Ingestion Processing engine 670 are routed through the AI Assisted Returns/Discounts/Credits Optimizer 680 which uses AI models to determine the least costly way to respond to the issue whether it be to issue a full or partial refund and/or require the items in question be returned or allow a buyer to keep them due to high shipping costs. The AI Assisted Returns/Discounts/Credits Optimizer 680 step uses automations and/or human agents to directly process the resolution in the relevant Resell Channels group 640 channel to inform the buyer and to update the Financial Posting and Reconciliation Engine 180 which can remit funds back to the buyer and update all relevant UME Gateway Ledgers. If a return is instructed by the AI Assisted Returns/Discounts/Credits Optimizer 680 it will inform the Returns Processing process 682 which tracks items expected to be returned to the UME Gateway to ensure they are received back and re-inventoried for processing prior to issuing any discounts or refunds.

Assuming a direct purchase or hold allocation is not made against active registered demand as described in FIGS. 5a and 5b, this portion of the UME Gateway is responsible for merchandising, listing, transacting, and fulfilling of sales of medical equipment to buyers "as-is", meaning no reconditioning or expectation of patient readiness takes place and no harvesting or conversion of parts occur. The goal of this portion of the UME Gateway is to maximize overall returns for healthcare systems and/or asset owners by matching medical equipment to the right potential buyers at the right time, through the right channels, at the right price.

The UME Gateway can support any number of channels where medical equipment can be sold. Some are directly managed and operated by the UME Gateway. Others are controlled by third parties and range from established and branded multibillion dollar marketplaces for industrial equipment to very small niche online and offline sellers specific to auction channels or sales of specific categories of medical devices. By supporting so many channels and alerting buyers of new products of interest, the exposure for UME Gateway medical equipment inventory is significantly increased allowing far more items to be sold on behalf of healthcare systems and asset owners. At the same time buyers are able to more efficiently find UME Gateway medical equipment they need and process the orders in the channels they are most comfortable with rather than being restricted to UME Gateway only direct sales. This makes buyer procurement easier to manage and reduces their overall costs to make the reverse supply chain for medical equipment more efficient.

Each third-party channel has its own product nomenclatures, financial terms, integrations, data formats, fulfillment options, and merchandising capabilities for items that need to be honored. For example, it is customary in auction channels to charge buyers a lower product price along with a premium for auction platform services, payment processing fees, and for item storage or fulfillment. Other channels may charge the UME Gateway listing fees, success fees, promotion fees, or require free or discounted shipping and other added charges that make even a higher product sales price less profitable for the UME Gateway. Certain UME Gateway controlled channels offer named customers discounts based on purchase history and negotiated agreements that also need consideration. Hence product price alone is not the best determinant of whether a given sale in a given channel is the most profitable outcome for the healthcare system and/or asset owner and the UME Gateway's AI models and analytics are required to set channel specific pricing and negotiating thresholds accordingly.

The UME Gateway works with the reFramer™ AI Econometric Evaluation Engine 120 to analyze and recommend which channels items should be listed in and incorporates its knowledge of each channel's listing, fulfillment, and financial requirements into the above-mentioned AI and business analytics models. In addition to channel selection, the recommended list prices, acceptable negotiated minimum offer prices, and promotion budgets for each channel are uniquely defined based on the final bottom line net margin of a fulfilled transaction.

Once channels are determined listings are created in them. The UME Gateway will automatically perform all the taxonomy and translation work to match product nomenclatures, condition values, shipping and payment policies, merchandising fields, and other content to what is needed for each channel. The UME Gateway is also able to virtually lot, kit, combine, and split products to structure channel listings differently than actual inventory configurations to increase sales prices and volumes. Depending on a channel's integration capabilities the listings will be automatically generated in near real-time or go through batch processing and uploads. For channels such as auctions where exclusive availability may be required for a product during the bidding period the UME Gateway will enforce and delist those items from all other channels to protect availability for the required period.

The UME Gateway then promotes relevant products and directs buyers to shop in different channels based on their preferred and allowable communication methods, buying profiles, channel preferences, and discounts. Promotions can range from email and SMS messages, paid ads, outbound calling, time-based discounts, and, depending on a channel's capabilities, channel specific promotions, communications, special offers, and messaging.

Due to the serialized nature of medical equipment with every item being unique, interest and activity in each device is monitored by tracking engagement with all catalog listings including views, inquiries, and offers taking place in each channel. Some channels also allow users to register as watchers or tag products as favorites giving further indication of demand. The UME Gateway summarizes the unique serialized medical device interest registrations into overall near real-time interest and activity levels for makes, models, and product categories providing early detection queues of demand spikes and drops. This information is also considered in terms of re-evaluating listings over time and whether to raise or lower price, change discounts, and/or rotate items to different channels or escape paths.

Since haggling negotiations are common in used medical equipment markets, products rarely sell for their listed price. Automated and human customer service agents monitor channel activity and can respond to inquiries and offers using the AI based acceptable pricing and negotiation rules provided by the Channel Based Offer Response Calculator 635. This includes automated offer acceptance or counter offering according to predefined rules. Exceptions require human intervention and logged approval audit trails to make sure market values of assets are preserved for healthcare systems and/or asset owners and any discounts beyond the standard UME Gateway rules are properly authorized.

While products sit in the multi-channel marketplace the UME Gateway and reFramer™ AI Econometric Evaluation Engine 120 monitor resale activity and market conditions as described in FIGS. 2*a* and 2*b*. New information can lead to recommendations to trigger changes in channel-based pricing, acceptable offers, or where and how products are listed. This could include pulling a piece of medical equipment from or adding it to other channels. For example, automatically pulling items for periodic auctions and relisting them if not sold is a common UME Gateway practice. Similarly, if changes in pricing or third-party channel fees exceed certain thresholds, items might be pulled from high-cost channels and placed into liquidation channels. Examples of other factors that could drive channel rotations or price and acceptable offer adjustments are new registered demand opportunities, new channels, new demand requests from healthcare systems, asset owners, or loyal buyers, age of inventory as assets often need to be disposed of in certain timeframes according to healthcare system and/or asset owner policies, or detected changes in market conditions such as emergency disease outbreaks or disasters requiring emergency response.

When a product is sold, orders from the various channels need to be ingested, processed, and fulfilled by the UME Gateway. AI and business process orchestrations perform the reverse mapping of channel taxonomies for products, payments, and fulfillments using the UME Gateway standards. Depending on the capabilities of the channel this ingestion is fully automated and near real-time or goes through semi-automated batch processing to feed into a generic order ingestion processor. Any virtual lotting or kitting is converted back to serialized inventory for processing fulfillments and paying healthcare systems and/or asset owners. The UME Gateway also combines auction lots and other individual line items purchased from the same buyer into a single virtual order for easier processing and fulfillment.

Order execution and delivery then follows process orchestration rules. Work orders are generated and managed by the UME Gateway's process orchestration engine to match the unique requirements of the transaction and selling channels, as each can have different rules for timing, holds, billing, packing, shipping, handling, and payment. Buyers are automatically alerted of the order process status when orders are received, ready to ship or pick up, and fulfillment is complete. Depending on the channel's rules and integration capabilities these alerts are performed directly by the UME Gateway or passed through to the channel itself to inform the buyer.

While most high volume medical equipment sellers require buyers to manage their own fulfillments, the UME Gateway offers buyers full-service logistics and fulfillment options. Used medical devices rarely come with manufacturer packaging and devices range in size from tiny handheld instruments to large medical beds or imaging equipment the size of a small room that needs de-installed. The thousands of different shape and size combinations associated with an order along with the need to protect sensitive medical equipment means custom de-assembly, packaging and crate construction is typically performed on demand. The UME Gateway makes this economically feasible at scale by automatically scanning orders, identifying optimal packing configurations, and identifying and taking necessary steps to protect sensitive medical devices, and then triggers work orders and process orchestrations to ensure proper fulfillment.

Frequent buyers are presented options for the UME Gateway to automatically control the consolidation and timing of their fulfillments. AI, analytics, and business rules can automatically combine multiple orders into single fulfillments saving the downstream reverse supply chain time and money on shipping, handling, and order tracking, which in turn make a healthcare system's and/or asset owner's medical devices more valuable in the UME Gateway. Buyers especially benefit from having the UME Gateway hold purchases until shipping thresholds, such as specific need dates, planned pickup routes, ideal freight cost timing, or full containers are met. The UME Gateway can process, track, and charge for advanced fulfillment services while running an automated abandonment processes when breaches occur.

The UME Gateway addresses the unique serialized nature of medical equipment items in order to avoid double selling any asset. There are no substitution options when it comes to medical devices that are purchased based on specific serial numbers, conditions, and related data. Swapping one item of the same make and model for another cannot normally be done without buyer approval according to most channel rules and sensible customer service in the medical equipment market. Hence the UME Gateway incorporates near real-time automations with all channels to identify when specific serialized items have been ordered or held in a channel and then pulls the listings from all other channels and places the products on hold in the UME Gateway until the order is completed or cancelled such that the item is safe to relist. Similar processes are performed if an item becomes unavailable for other reasons such as healthcare system and/or asset owner redeployments, recycling, loss, damage, or otherwise. Those medical devices are removed from all assigned channels in near real-time to prevent selling something that cannot be fulfilled.

Post order exceptions, returns, discounts, and credits are very common in the used medical equipment marketplace for "as-is" items. These scenarios also run through AI models and analytics in the AI Assisted Returns/Discounts/Credits Optimizer 680 allowing customer service queues to evaluate and recommend the best course of action based on the value of the item and likelihood of selling it again, cost of physically returning the items, policies of third-party channels and payment processors, seller reputation scores, and the potential that the buyer claim is fraudulent. The UME Gateway then applies its decision-making capabilities and executes the necessary communications, case escalations, logistics, financial transactions, or other necessary actions to bring these cases to conclusion. Optimization of these common scenarios preserves residual value for healthcare systems and/or asset owners and improves the integrity of the reverse supply chain markets.

In addition to processing all the above, every UME Gateway sale and credit requires accounting for fees, revenue share, and channel allocations to healthcare systems and/or asset owners. The UME Gateway has algorithms to assign and split revenues and costs when multi-order items and discounts occur from different sources to fairly compensate the healthcare systems and/or asset owners according to their contracts. In addition, the UME Gateway supports processing credits and subsequent resales with allocations back to the healthcare system's and/or asset owner's ledgers ensuring fair accounting through the entire disposition lifecycle of a medical device.

Figure 7A:
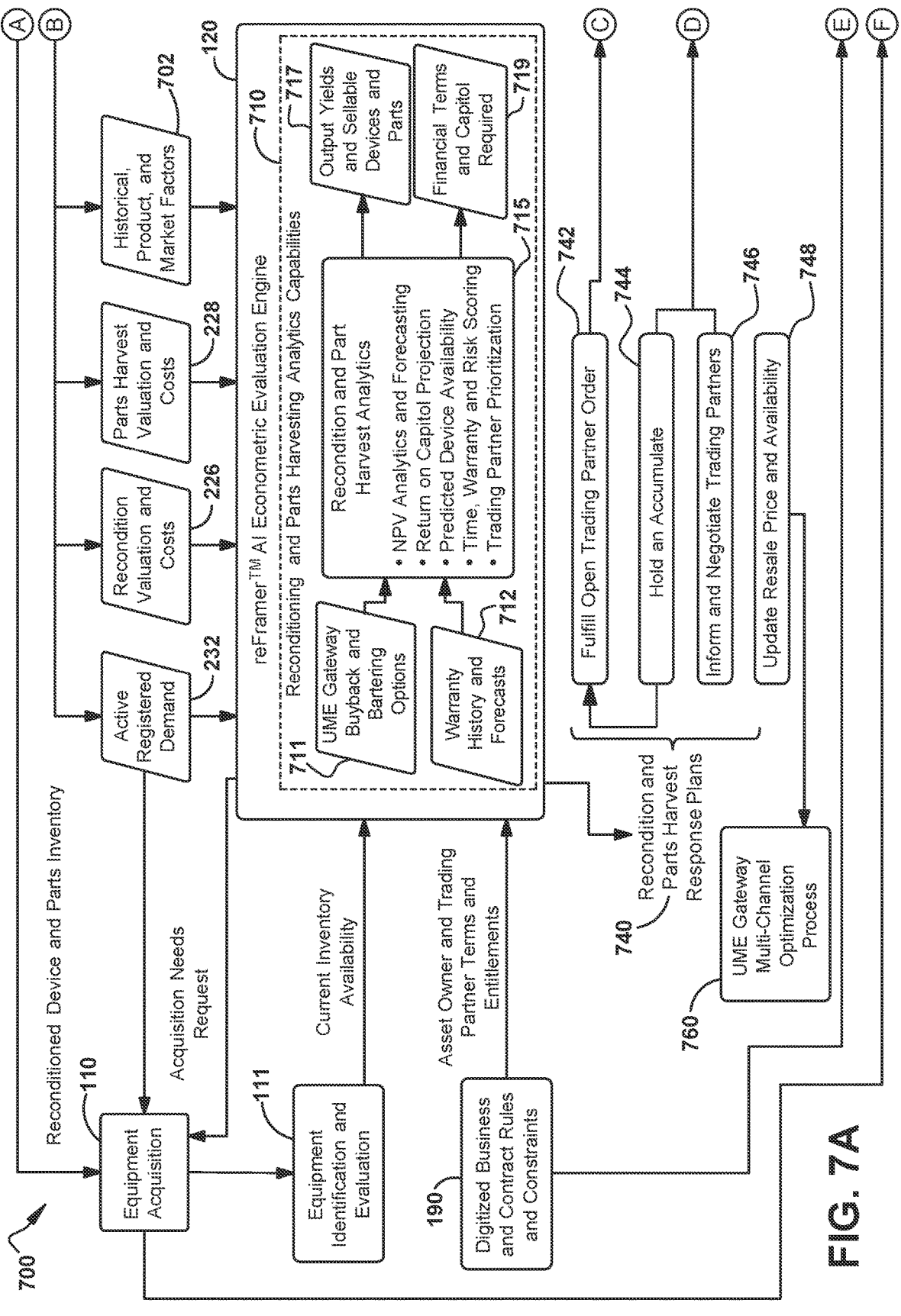
FIGS. 7*a* and 7*b* schematically present a flow chart showcasing the UME Gateway Integrated Recondition and Parts Harvest Supply Chains in accordance with aspects of the present disclosure.
Figure 7B:
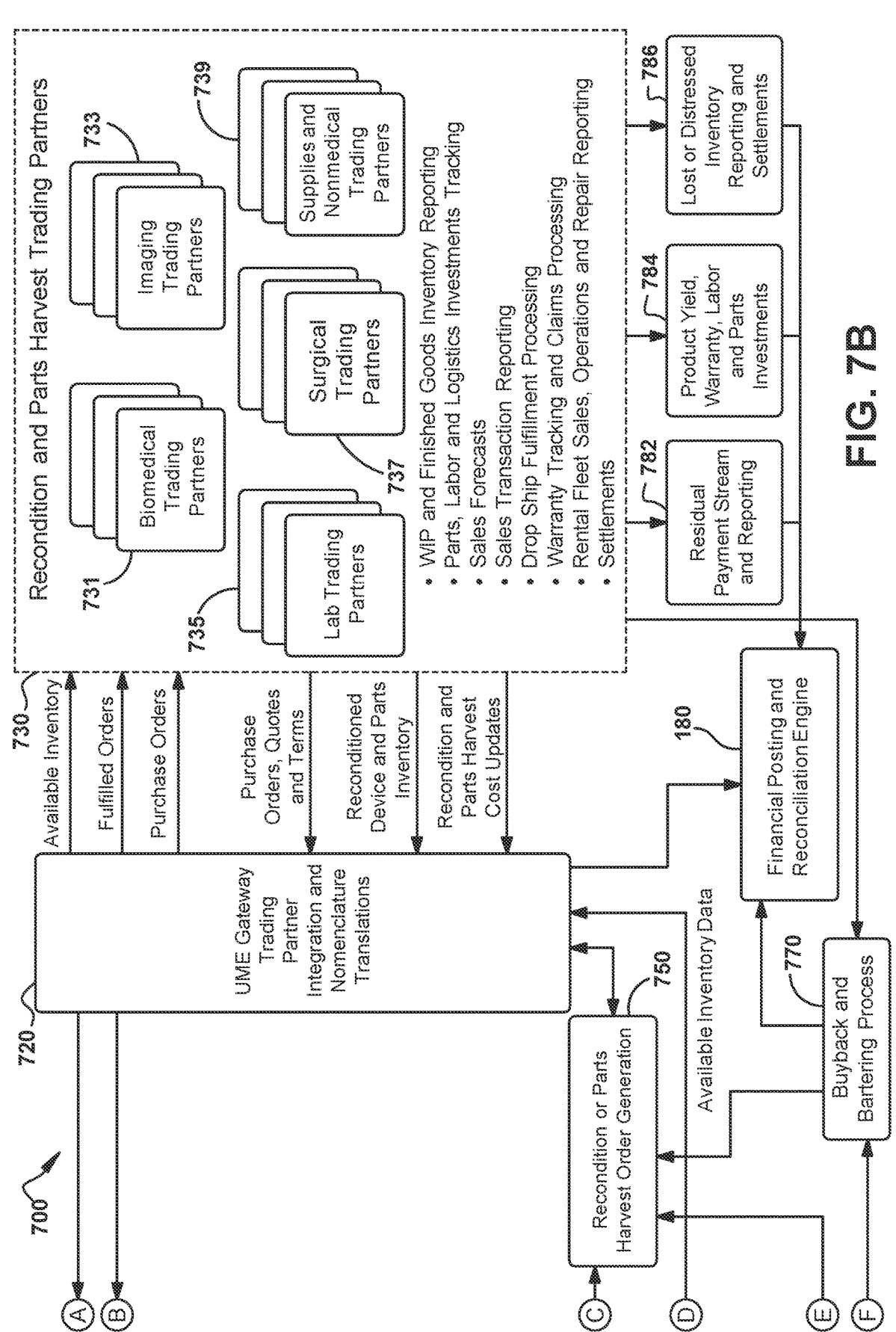

FIGS. 7*a* and 7*b* schematically present a UME Gateway Integrated Recondition and Parts Harvest Supply Chain flowchart 700, showcasing how the UME Gateway's reconditioning and parts harvesting supply chain capabilities operate. The UME Gateway Integrated Recondition and Parts Harvest Supply Chain flowchart 700 includes the Equipment Acquisition process 110 found in FIG. 1*a*, the Equipment Identification and Evaluation process 111 found in FIG. 1*a*, the Digitized Business and Contract Rules and Constraints database 190 found in FIG. 1*a*, the reFramer™ AI Econometric Evaluation Engine 120 found in FIG. 1*a*, a Reconditioning and Parts Harvesting Capabilities group 710 within the reFramer™ AI Econometric Evaluation Engine 120, the Active Registered Demand database 232 found in FIG. 2*b*, the Recondition Valuation and Costs database 226 found in FIG. 2*a*, the Parts Harvest Valuation and Costs database 228 found in FIG. 2*a*, a Historical, Product and Market Factors dataset 702, a UME Gateway Trading Partner Integration and Nomenclature Translations engine 720, a Recondition and Parts Harvest Trading Partners group 730, a Recondition and Parts Harvest Response Plans group 740, a Recondition or Parts Harvest Order Generation process 750, a UME Gateway Multi-Channel Optimization Process 760, a Buyback and Bartering Process 770, the Financial Posting and Reconciliation Engine 180 found in FIG. 1*b*, a Residual Payment Stream and Reporting engine 782, a Product Yield, Warranty, Labor and Parts Investments engine 784, and a Lost or Distressed Inventory Reporting and Settlements engine 786.

The Reconditioning and Parts Harvesting Analytics Capabilities group 710 includes a UME Gateway Buyback and Bartering Options database 711, a Warranty History and Forecasts database 712, a Recondition and Parts Harvest Analytics engine 715, an Output Yields and Sellable Devices and Parts database 717, and a Financial Terms and Capital Required database 719.

The Recondition and Parts Harvest Trading Partners group 730 includes a Biomedical Trading Partners set 731, an Imaging Trading Partners set 733, a Lab Trading Partners set 735, a Surgical Trading Partners set 737, and a Supplies and Nonmedical Trading Partners set 739.

The Recondition and Parts Harvest Response Plans group 740 includes a Fulfill Open Trading Partner Order response 742, a Hold and Accumulate response 744, an Inform and Negotiate Trading Partner response 746, and an Update Resale Price and Availability response 748.

The Equipment Acquisition process 110 which is the same as described in FIG. 1*a* is the process by which medical equipment is made available to the UME Gateway. This step can receive sourcing requests related to known active demand from the Active Registered Demand database 232 and the reFramer™ AI Econometric Evaluation Engine 120 to seek or source specific medical equipment that has known current demand to meet reconditioning or parts harvesting requirements. Additional details about the processes and activities of this process are as described in FIG. 3.

The Equipment Identification and Evaluation process 111 which is the same as described in FIG. 1*a* is the process by which image processing is combined with AI and other techniques to efficiently identify makes, models, conditions, system completeness, specifications, included accessories, and other basic information about medical equipment to feed into subsequent analysis, databases, and automations that can be processed by the UME Gateway. This would include any identification of the needs, opportunities and issues associated with reconditioning or harvesting parts from a specific piece medical equipment. Once the basic information is known, the information about current available inventory is sent to the reFramer™ AI Econometric Evaluation Engine 120 where among other things it can determine if newly available UME Gateway inventory could be used to satisfy medical equipment reconditioning or parts harvesting supply chain needs. Additional details about the processes and activities of this process are as described in FIG. 3.

The Digitized Business and Contract Rules and Constraints database 190 which is the same as described in FIG. 1*a* contains, among other things, reconditioning and parts harvesting trading partner contract rules, entitlements, and constraints that specify blanket terms and conditions which may apply to selling equipment to or acquiring equipment from reconditioning and parts harvesting trading partners. These terms and conditions need to be considered when deciding whether and how the UME Gateway should perform reconditioning or parts harvesting on its inventory and/or acquire reconditioned medical devices, parts, or related services.

The reFramer™ AI Econometric Evaluation Engine 120 which is the same as described in FIG. 1*a* contains AI capabilities to determine when to match available UME Gateway medical equipment inventory to device reconditioning or parts harvesting opportunities along with the trading partners to provide the services and the financial terms for performing the reconditioning or parts harvesting. These capabilities are detailed in the description of the Reconditioning and Parts Harvesting Analytics Capabilities group 710.

The Reconditioning and Parts Harvesting Analytics Capabilities group 710 within the reFramer™ AI Econometric Evaluation Engine 120 uses AI models to perform, among other things, the designating of available UME Gateway medical equipment inventory to a recondition or parts harvest escape path, the trading partners who should do the reconditioning or parts harvesting work and under what terms and conditions, and the expected capital requirements and returns from pursuing these alternatives in lieu of other escape path options.

The UME Gateway Buyback and Bartering Options database 711 is a database containing information regarding medical equipment and parts that can be purchased from reconditioning and parts harvesting trading partners and when these items can be acquired in exchange for as-is medical equipment in lieu of financial payment.

The Warranty History and Forecasts database 712 is a database of historical warranty claims and performance and projected warranty claims and liabilities the UME Gateway might incur from reselling reconditioned medical devices and parts.

The Recondition and Parts Harvest Analytics engine 715 creates recommendations for the allocation of medical equipment for reconditioning and parts harvesting taking into account allowable matches and constraints of a given piece of medical equipment, the medical equipment's Net Present Value (NPV) calculations from selling via recondition or parts harvest processing, the time, warranty and risk scoring of the piece of medical equipment and potential liability that might arise, the prioritization of which trading partner should do the reconditioning or parts harvesting, the predicted device availability of securing inventory needed to be meet recondition and parts harvest requirements, and the return on capital projection of the piece of medical equipment if additional investment is required by the UME Gateway when making its recommendations.

The Output Yields and Sellable Devices and Parts database 717 is generated from the Recondition and Parts Harvest Analytics engine 715 defining what sellable reconditioned medical devices and parts should become available from a given allocation of UME Gateway medical equipment inventory to those escape paths.

The Financial Terms and Capital Required database 719 is generated from the Recondition and Parts Harvest Analytics engine 715 informing the UME Gateway of potential liabilities, capital investments, financial terms, and future revenue streams expected from medical equipment inventory allocated to recondition or parts harvest escape paths.

The Active Registered Demand database 232 which is the same as described in FIG. 2b includes details of all known active registered demand for medical equipment (including reconditioned devices and parts or from reconditioning and parts harvesting trading partners) for use by the reFramer™ AI Econometric Evaluation Engine 120 and can be accessed by the sourcing steps of the Equipment Acquisition process 110 to focus resources on communicating known needs to acquire medical equipment that is currently demanded from healthcare systems and/or asset owners.

The Recondition Valuation and Costs database 226 which is the same as described in FIG. 2a is a database of the estimated value of specific refurbished or reconditioned pieces of medical equipment, as well as the estimated costs associated with applying parts and labor for reconditioning specific pieces of medical equipment so that a return on investment calculation can be performed relative to selling an item as-is.

The Parts Harvest Valuation and Costs database 228 which is the same as described in FIG. 2a is a database of the estimated value of specific parts harvested from medical equipment contained within the UME Gateway, as well as the estimated costs associated with harvesting specific parts from the medical equipment contained within the UME Gateway so that a return on investment calculation can be performed on the benefit of investing in parts harvesting.

The Historical, Product and Market Factors dataset 702 is data available to the UME Gateway relative to historical performance and current market conditions for reconditioned device and parts inventory relative to as-is medical equipment, along with the ways devices and parts can be combined to make complete systems and subsystems or other lots and kits desirable for buyers.

The UME Gateway Trading Partner Integration and Nomenclature Translations engine 720 is a set of automations that translates data to and from the UME Gateway's nomenclature and the formats used by reconditioning and parts harvesting trading partners in the Recondition and Parts Harvest Trading Partners group 730, specifically information regarding available inventory, fulfilled orders, and purchase orders. This engine performs automations to push data to or pull or receive data from those trading partners.

The Recondition and Parts Harvest Trading Partners Group 730 is a set of trading partners that provide reconditioning or parts harvesting services to the UME Gateway designated by the types of medical equipment they are approved to perform these services on.

The Biomedical Trading Partners set 731 is a set of trading partners in the biomedical field authorized by the UME Gateway to perform reconditioning or parts harvesting services on biomedical equipment.

The Imaging Trading Partners set 733 is a set of trading partners in the imaging field authorized by the UME Gateway to perform reconditioning or parts harvesting services on imaging equipment.

The Lab Trading Partners set 735 is a set of trading partners in the laboratory equipment field authorized by the UME Gateway to perform reconditioning or parts harvesting services on lab equipment.

The Surgical Trading Partners set 737 is a set of trading partners in the surgical instruments and equipment field authorized by the UME Gateway to perform reconditioning or parts harvesting services on surgical instruments and equipment.

The Supplies and Nonmedical Trading Partners set 739 is a set of trading partners in the medical supplies, information technology, office equipment, or other fields related to inventory other than medical devices that the UME Gateway regularly receives from healthcare systems and/or asset owners who are authorized by the UME Gateway to perform reconditioning or parts harvesting services on this type of inventory.

The Recondition and Parts Harvest Response Plans Group 740 is a set of responses the reFramer™ AI Econometric Evaluation Engine 120 may recommend with regards to orders, negotiations, and pricing of UME Gateway medical equipment inventory it is or has previously deemed suitable for reconditioning or parts harvesting escape path processing.

The Fulfill Open Trading Partner Order response 742 is a recommendation from the reFramer™ AI Econometric Evaluation Engine 120 to use a given piece of UME Gateway medical equipment inventory to immediately process a fulfillment of open orders from reconditioning or parts harvesting trading partners.

The Hold and Accumulate response 744 is a recommendation from the reFramer™ AI Econometric Evaluation Engine 120 to place a hold on a given piece of UME Gateway medical equipment inventory with a prediction that additional compatible inventory and/or sufficient quantities will soon come in necessary to have inventory to complete a system or meet other lotting, kitting, or minimum yield quantities needed to sufficiently perform reconditioning or parts harvesting.

The Inform and Negotiate Trading Partner response 746 is a recommendation from the reFramer™ AI Econometric Evaluation Engine 120 to inform reconditioning and parts harvesting trading partners about the availability of designated pieces of UME Gateway medical equipment inventory with expectation of negotiating and completing a sale with one of those trading partners.

The Update Resale Price and Availability response 748 is a recommendation from the reFramer™ AI Econometric Evaluation Engine 120 regarding a piece of UME Gateway medical equipment inventory to sell it in one or more UME Gateway approved channels at a specific price rather than continuing to hold or restrict its sale to only reconditioning or parts harvesting trading partners.

The Recondition or Parts Harvest Order Generation process 750 is a process for generating transactions necessary to complete an order with a reconditioning and/or parts harvesting trading partner according to agreed upon terms and conditions.

UME Gateway Multi-Channel Optimization Process 760 is a dynamic multi-channel listing and selling process for UME Gateway medical equipment as described in more detail in FIGS. 6a and 6b.

The Buyback and Bartering Process 770 is a process where the UME Gateway is preapproved to acquire reconditioned medical devices and parts from suppliers in the Reconditioned and Parts Harvest Trading Partners group 730 under pre-established terms and conditions.

The Financial Postings and Reconciliation Engine 180 which is the same as described in FIG. 1b processes all financial settlements for consignment splits, residual revenue tracking, credit allocations, rebates, warranty claims, and other transactions for the UME Gateway and for healthcare systems and/or asset owners as it relates to medical equipment processed through recondition or parts harvest escape paths, and performs reconciliations to ensure expected transactions and data is received and accurately accounted for.

The Residual Payment Stream and Reporting engine 782 monitors required and expected data and payments are being received from trading partners in the Recondition and Parts Harvest Trading Partners group 730 related to their sales of reconditioned medical devices and parts generated from UME Gateway supplied medical equipment inventory.

The Product Yield, Warranty, Labor and Parts Investments engine 784 receives required and expected data from trading partners in the Recondition and Parts Harvest Trading Partners group 730 related to the yields they generate from performing reconditioning and parts harvesting services, their investments of labor and parts in performing the services, and any warranty claims arising from reconditioning and parts harvesting services and sales of UME Gateway supplied medical equipment inventory.

The Lost or Distressed Inventory Reporting and Settlements engine 786 works to create/generate/come to a settlement with vendors from the Recondition and Parts Harvest Trading Partners group 730 regarding lost or distressed inventory or yield issues that creates a financial loss relative to predicted returns and/or contractual obligations.

The flow of the UME Gateway Integrated Recondition and Parts Harvest Supply Chain flowchart 700 is described herein. The Equipment Acquisition process 110 brings new medical equipment into the UME Gateway where the Equipment Identification and Evaluation process 111 ensures the relevant photos and information about that medical equipment inventory are captured and made available to the reFramer™ AI Econometric Evaluation Engine 120 to make recommendations regarding the disposition of that medical equipment. Any known active demand for reconditioned medical devices or parts from healthcare systems and/or known active demand from reconditioning and parts harvesting buyers in the Active Registered Demand database 232 or as prioritized and determined by the reFramer™ AI Econometric Evaluation Engine 120 is communicated to the Equipment Acquisition process 110 to prioritize sourcing of the most needed medical equipment to meet that demand. Current Available Inventory from the Equipment Identification and Evaluation process 111 is continuously evaluated by the Recondition and Parts Harvest Analytics engine 715 in the Reconditioning and Parts Harvesting Capabilities group 710 of the reFramer™ AI Econometric Evaluation Engine 120 to determine what medical equipment should be recommended be added to or removed from recondition or parts harvest escape paths. The AI models executed by the Recondition and Parts Harvest Analytics engine 715 consider information from the Active Registered Demand database 232, the Recondition Valuation and Costs database 226, the Parts Harvest Valuation and Costs database 238, the Historical, Product, and Market Factors dataset 702, the Digitized Business and Contract Rules and Constraints database 190, the UME Gateway Buyback and Bartering Options database 711, and the Warranty History and Forecasts database 712 in making recommendations. The Recondition and Parts Harvest Analytics engine 715 uses AI to predict the net present value (NPV) from assigning medical equipment to a reconditioning or parts harvesting process prior to sale, the return on capital for any labor and parts invested, the likelihood of acquiring any necessary compatible inventory required to perform lotting, kitting, or meet sufficient quantities demanded by reconditioning or parts harvest processes and yields, the potential risks from warranty liabilities or extended timeframes it takes to recondition or harvest parts from a device and sell the outputs, and which trading partners are most likely to obtain the best NPV and return on capital. The Recondition and Parts Harvest Analytics engine 715 AI models ensure all calculations and recommendations abide by agreements in the Digitized Business and Contract Rules and Constraints database 190 which includes the terms for working with reconditioning and parts harvesting vendors and may prevent or require reconditioning or parts harvesting for equipment received from certain healthcare systems and/or asset owner. The Recondition and Parts Harvest Analytics engine 715 updates the Output Yields and Sellable Devices and Parts database 717, and a Financial Terms and Capital Required Database 719 for UME Gateway medical equipment inventory the reFramer™ AI Econometric Evaluation Engine 120 determines should proceed to or be pulled from reconditioning or parts harvesting escape paths and then the reFramer™ AI Econometric Evaluation Engine 120 passes the response plan for that inventory to the Recondition and Parts Harvest Response plans group 740. The Recondition and Parts Harvest Response plans group 740 evaluates the reFramer™ AI Econometric Evaluation Engine 120 provided recommended response which can be the Fulfill Open Trading Partner Order response 742, the Hold and Accumulate response 744, the Inform and Negotiate Trading Partner response 746, or the Update Resale Price and Availability response 748. If the Fulfill Open Trading Partner Order response 742 is selected the associated medical equipment inventory will be immediately assigned to an open order with a trading partner and passed to the Recondition or Parts Harvest Order Generation process 750 for completing the transaction, per the rules and constraints from the Digitized Business and Contract Rules and Constraints database 190, and then is sent to the UME Gateway Trading Partner Integration and Nomenclature Translations engine 720 for processing. If the Hold and Accumulate response 744 is selected the UME Gateway will hold the inventory and add it to other related inventory items needed to generate complete systems or sufficient inventory quantities required for lotting, kitting, or successful outcomes from reconditioning or parts harvesting. Inventory held by the Hold and Accumulate Response 744 will be transitioned to the Fulfill Open Trading Partner Order response 742 and an order placed once all required inventory has been accumulated for an order. Inventory held by the Hold and Accumulate Response 744 will also be communicated to the UME Gateway Trading Partner Integration and Nomenclature Translations engine 720 for communication to applicable reconditioning and parts harvesting vendors for their planning purposes. If the Inform and Negotiate Trading Partner response 746 is selected information about that inventory will be passed to the UME Gateway Trading Partner Nomenclature Translations engine 720 for communication to applicable reconditioning and parts harvesting vendors in hopes of generating interest and negotiating a sales transaction. If the Update Resale Price and Availability response 748 is selected the UME Gateway will remove any holds exclusive to the recondition or parts harvest escape paths and initiate updates through the UME Gateway Multi-Channel Optimization Process 760 which will execute the processes for channel listing and sales as described in FIGS. 6a and 6b. All reconditioning and parts harvesting designated inventory availability, fulfilled trading partner orders, and purchase orders for buying reconditioning or parts harvesting services are passed from the Recondition and Parts Harvest Response Plans group 740 to the UME Gateway Trading Partner Nomenclature Translations engine 720 where they are converted to the formats necessary to be pushed to the applicable trading partner(s) they are intended for. The UME Gateway Trading Partner Nomenclature Translations engine 720 will push the converted information to the appropriate trading partners in the Recondition and Parts Harvest Trading Partners group 730 as determined by the Recondition and Parts Harvest Analytics engine 715 where the recipients can be members of the Biomedical Trading Partners set 731, the Imaging Trading Partners set 733, the Lab Trading Partners set 735, the Surgical Trading Partners set 737, and/or the Supplies and Nonmedical Trading Partners set 739 as applicable based on the type of inventory involved. Trading partners in the Recondition and Parts Harvest Trading Partners group 730 will push their demand for products in the form of orders or quotes, along with all applicable terms to the UME Gateway's Trading Partner Integration and Nomenclature Translations engine 720 which will update the Active Registered Demand database 232. Trading partners in the Recondition and Parts Harvest Trading Partners group 730 will push their current reconditioned device and parts inventory and applicable terms and pricing along with their latest recondition and parts harvest costing models to the UME Gateway's Trading Partner Integration and Nomenclature Translations engine 720 which will update the Financial Posting and Reconciliation Engine 180, the Recondition Valuation and Costs database 226, the Parts Harvest Valuation and Costs database 228, and the Historical, Product, and Market Factors dataset 702 as applicable so the latest information is available for the reFramer™ AI Econometric Evaluation Engine 120 and the Equipment Acquisition process 110. Where the UME Gateway recognizes a need for reconditioned inventory or parts in the Equipment Acquisition process 110 and is eligible to purchase inventory from vendors in the Recondition and Parts Harvest Trading Partners group 730, either for cash or in exchange of other UME Gateway as-is medical device inventory needed by these partners, the Buyback and Bartering Process 770 will be automatically triggered and send orders to the Recondition or Parts Harvest Order Generation engine 750 for communication to the appropriate vendor and to the Financial Posting and Reconciliation Engine 180 for accounting for the purchase and any resulting barter transactions and fulfillments required to compensate the vendor with as-is UME Gateway medical equipment. Trading partners in the Recondition and Parts Harvest Trading Partners group 730 that are under active contracts that require providing ongoing updates to the UME Gateway regarding the results of medical equipment inventory reconditioning, parts harvesting processing and/or reselling will send required information to the Residual Payment Stream and Reporting engine 782, the Product Yield, Warranty, Labor and Parts Investments engine 784, and the Lost or Distressed Inventory Reporting and Settlements engine 786 as applicable. The Residual Payment Stream and Reporting engine 782, the Product Yield, Warranty, Labor and Parts Investments engine 784, and the Lost or Distressed Inventory Reporting and Settlements engine 786 will process and pass all UME Gateway required transactions to the Financial Posting and Reconciliation Engine 180 to generate UME Gateway accounting system transactions and track financial performance related to reconditioning and parts harvesting activities, ensure trading partner compliance with terms and agreements, and update records and information for healthcare systems and/or asset owners that provided the underlying equipment.

A major differentiator of the UME Gateway is its ability to incorporate and analyze the potential economic benefits and costs of having downstream trading partners invest in reconditioning or harvesting parts from devices. Such actions can be significantly more or less profitable than the direct as-is resell of piece of medical equipment, depending on the condition and completeness of the input devices as well as the added time, processing, costs, holding periods, and risks involved. By incorporating these trading partners directly into the UME Gateway healthcare systems and/or asset owners can see even higher returns from their disposition medical devices.

Incorporating this information into the reFramer™ AI Econometric Evaluation Engine 120 helps better determine the current as-is value of a piece of medical equipment as well as the viability of participating in these downstream escape paths. Further benefits include the ability for the UME Gateway to manage custom economic arrangements with downstream processors who specialize in reconditioning or parts harvesting activities to equip them to more efficiently receive and process higher amounts of equipment while automating the complex accounting necessary to compensate healthcare systems and/or asset owners.

Trading partners are identified for major asset types, makes, and models where reconditioning or parts harvesting are common and likely to yield benefits at scale. Digitization of the economic and supply chain business arrangements are performed for process orchestration and econometric evaluations. In addition, the trading partner provides data on expected time, cost, and yield factors associated with refurbishment or parts harvesting as well as anticipated product configurations, revenue, margin, and returns they will generate and any associated warranty liabilities that might arise. AI tools are trained using supervised learning to incorporate and harmonize a vendor's information with the UME Gateway's normalized equipment master data models to enable automated translation and communication. The UME Gateway allows for NPV pricing, future value margin sharing, or a hybrid of initial upfront charging for a medical device along with payment streams from subsequent rentals, resale, or parts sales post processing by the trading partner.

Custom economic arrangements and preferred access to devices encourage medical equipment reconditioning and parts harvesting vendors to participate in this portion of the UME Gateway in three ways. First, they can secure access to significantly more medical devices with lower overall out-of-pocket investment by entering into agreements where payments are due only after the reconditioning and/or parts harvesting activities are completed and the outputs sold, which is worth sharing a portion of downstream value. Secondly, reconditioning and parts harvesting vendors can enter into arrangements where the UME Gateway has committed buyback provisions so vendors know their investment in inventory, materials, or labor to recondition or part a piece of medical equipment from the UME Gateway will generate a guaranteed return before making the investment. Finally, these vendors can secure preferred access to receive scare supply of as-is medical equipment to convert into sellable reconditioned and parts inventory by entering into bartering type arrangements with the UME Gateway allowing them to convert their reconditioned medical devices and parts into a new supply of as-is inventory without an outlay of scarce capital. These arrangements allow significantly more medical devices to make their way back into the reverse supply chain and productively reenter the marketplace while allowing the relatively small reconditioning and parts harvesting vendors to grow much faster than their capital would traditionally allow. AI and process orchestrations are used to minimize risk taking, track and enforce the economic rules associated with integrated reconditioning and harvesting supply chain transactions, and to apply financial controls and reconciliations to ensure proper accounting and settlements take place.

Healthcare systems and/or asset owners register which types of medical devices can participate in the integrated reconditioning and harvesting supply chain and under what financial, timing, and business process terms. The UME Gateway automatically enforces these requirements allowing healthcare systems and/or asset owners to choose whether to mitigate risk, prioritize timing of disposition of their assets, or attempt to maximize long-term returns from their disposition medical equipment. The reFramer™ AI Econometric Evaluation Engine 120 incorporates these contractual and financial details in determining whether assets should be considered for the reconditioning or the parts harvesting escape paths and if the healthcare system and/or asset owners' risk and timing thresholds will be met. Certain assets may also instantly opt into a reconditioning or parts harvesting escape paths based on the underlying contracts.

The reFramer™ AI Econometric Evaluation Engine 120 considers many factors including the completeness and condition of the input medical devices, sources of all components contributed from the UME Gateway, what needs added by the trading partner, the expected output yields into sellable inventory items along with their completeness, specifications, and accessories, the risks of extended time to resale through this process, any buyback provisions for other use in the UME Gateway, and any subsequent expected warranty tracking and claims processing reserves and holdbacks. Because of the complexity of these escape paths for medical equipment, the reFramer™ AI Econometric Evaluation Engine 120 incorporates risk mitigation and financial exposure scores into the model to prevent overleveraging these escape paths, even when they might suggest a higher ROI. This ensures the UME Gateway protects the interests of the healthcare systems and/or asset owners from being overleveraged in case demand conditions change.

The UME Gateway tracks all events and ensures all settlements for every device, whether as complete systems or parts are performed for both the healthcare system and/or asset owner and the trading partner. AI based process orchestration monitoring detects, alerts, and reports on potential gaps or anomalies to ensure prompt follow up and close out of any risks or issues, as these transactions can become quite complex with a single piece of medical equipment spawning dozens of individual downstream transactions through its lifecycle.

Warranty tracking, claims processing, returns, discounts, and credits are managed and resulting settlements are tracked for these escape paths by the Financial Posting and Reconciliation Engine 180. The UME Gateway is designed to handle timing and sequencing of these transactions across all parties to control exposure.

A buyback provision is managed from contractual and process orchestration engine which allows the UME Gateway to identify any reconditioned or approved harvested parts items that were created from or include UME Gateway sourced inventory. This allows the UME Gateway to offer patient ready medical equipment and parts for sale to healthcare systems and/or asset owners via the Credit Redemption Marketplace 160 as described in FIG. 1*b* and FIG. 8*a*. This also helps the UME Gateway more efficiently meet its own direct market demand for the reconditioned medical equipment and/or parts it provides healthcare providers and/or asset owners giving them additional benefits from their UME Gateway participation.

Figure 8A:
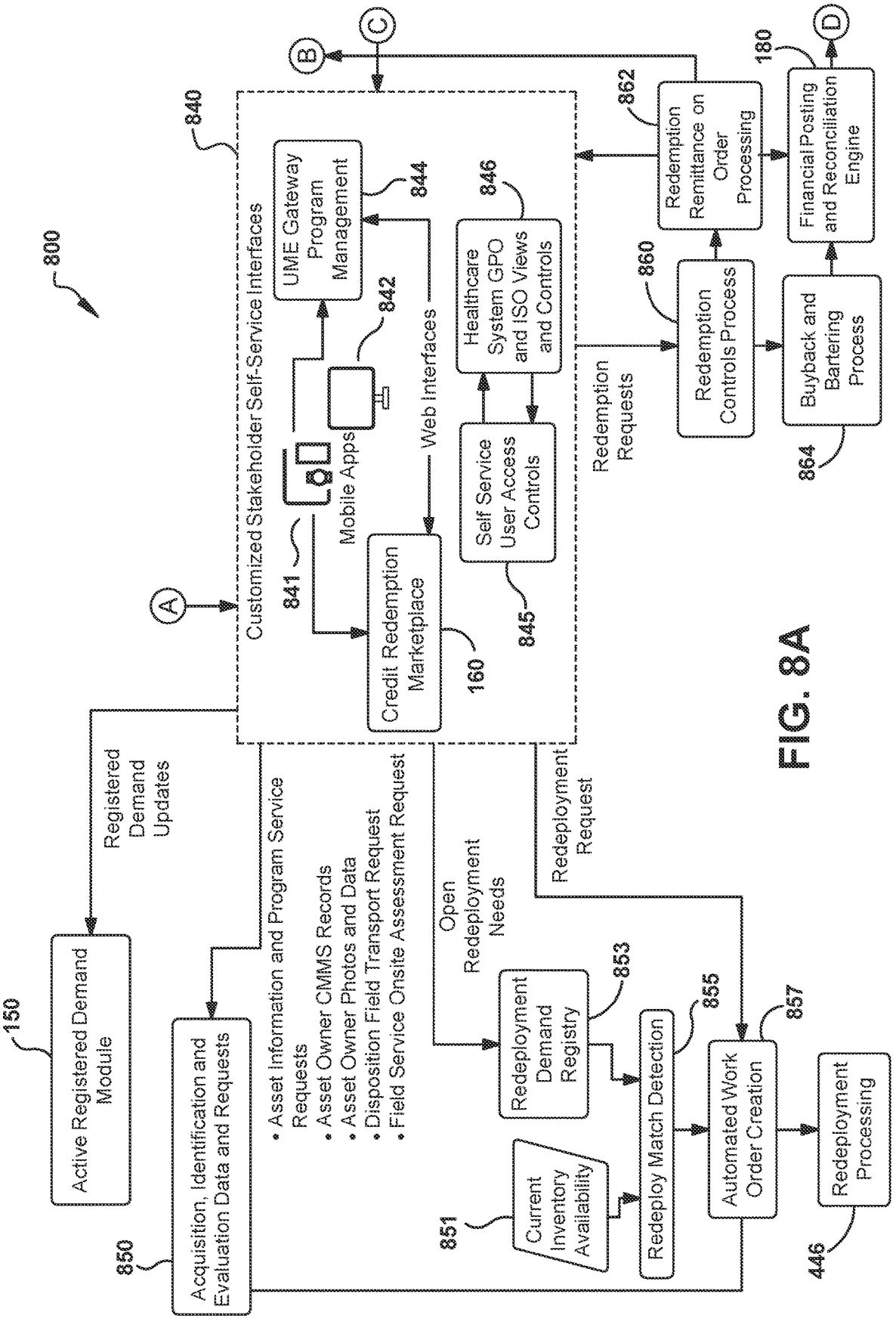
FIGS. 8*a* and 8*b* schematically present a flow chart showcasing the UME Gateway Healthcare System Asset Stakeholder Communications Engine and Credit Redemption Marketplace in accordance with aspects of the present disclosure.
Figure 8B:
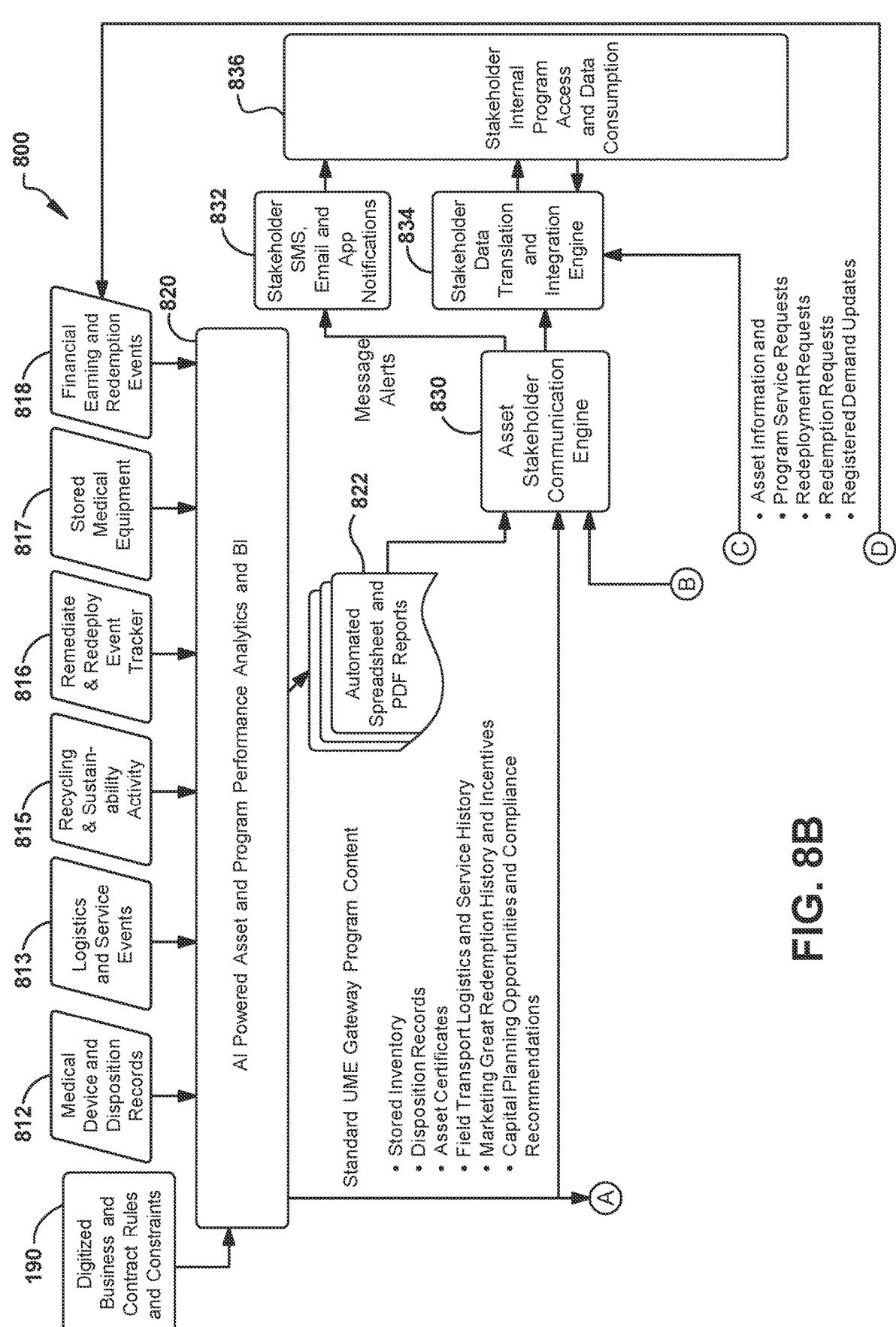

FIGS. 8*a* and 8*b* schematically present a UME Gateway Healthcare System Asset Stakeholder Communications Engine and Credit Redemptions Marketplace flowchart 800, showcasing how the UME Gateway's communications with healthcare systems and the access to the credit redemptions marketplace operates. The UME Gateway Healthcare System Asset Stakeholder Communications Engine and Credit Redemptions Marketplace flowchart 800 includes the Digitized Business and Contract Rules and Constraints database 190 found in FIG. 1*a*, a Medical Device and Disposition Records database 812, a Logistics and Service Events database 813, a Recycling and Sustainability Activity database 815, a Remediate and Redeploy Event Tracker database 816, a Stored Medical Equipment database 817, a Financial Earning and Redemption Events database 818, an AI Powered Asset and Program Performance Analytics and BI engine 820, an Automated Spreadsheet and PDF Reports generator 822, an Asset Stakeholder Communications Engine 830, a Stakeholder SMS, Email, and App Notifications generator 832, a Stakeholder Data Translation and Integration Engine 834, a Stakeholder Internal Program Access and Data Consumption process 836, the Active Registered Demand Module 150 found in FIG. 1*b*, a Customized Stakeholder Self-Service Interfaces group 840, an Acquisition, Identification, and Evaluation Data and Requests process 850, a Current Inventory Availability database 851, a Redeployment Demand Registry 853, a Redeploy Match Detection process 855, an Automated Work Order Creation process 857, the Redeployment Processing activity 446 found in FIG. 4*a*, a Redemption Controls Process 860, a Redemption Remittance or Order Processing process 862, a Buyback and Bartering Process 864, and the Financial Posting and Reconciliation Engine 180 found in FIG. 1*b*.

The Customized Stakeholder Self-Service Interfaces group 840 includes a Mobile Apps group 841, a Web Interfaces group 842, the Credit Redemption Marketplace 160 found in FIG. 1*b*, a UME Gateway Program Management module 844, a Self-Service User Access Controls module 845, and a Healthcare System GPO and ISO Views and Controls module 846.

The Digitized Business and Contract Rules and Constraints database 190 which is the same as described in FIG. 1*a* is a database that includes among other things the digitized contract terms and other business, compliance, and governance constraints of healthcare systems and asset owners that are automatically applied to every applicable decision and transaction in the UME Gateway. This includes all healthcare system and asset owner pricing, discounts, and entitlements and governance rules for what is required or allowed for their assets, how they can redeem credits and interact with the Credit Redemption Marketplace 160 and the Redemption Controls Process 860, and the details for configuring their UME Gateway self-service access points.

The Medical Device and Disposition Records database 812 is a database containing information regarding all of the medical devices that have been processed by the UME Gateway including the healthcare system and/or asset owner providing each device, the status of each device if still available or the escape path it was processed in, and all associated disposition records for each device.

The Logistics and Service Events database 813 is a database containing information regarding logistics and service events performed by the UME Gateway and the healthcare system and/or asset owner receiving each service event.

The Recycling and Sustainability Activity database 815 is a database containing information regarding the recycling and/or sustainability processing records including the recycling organization used, process performed, and other compliance details for all assets going through the UME Gateway's recycling escape path.

The Remediate and Redeploy Event Tracker database 816 is a database that holds all remediation and redeployment events performed on UME Gateway held medical equipment and includes the applicable healthcare system and/or asset owner the remediation or redeployment event was performed for.

The Stored Medical Equipment database 817 is a database containing information regarding all of the medical equipment currently being held in the storage disposition escape path by the UME Gateway and the healthcare system or asset owner the equipment is being held for, along with records of all equipment previously stored at a UME Gateway facility and where the assets were ultimately transitioned after leaving storage.

The Financial Earning and Redemption Events database 818 is a database of all financial earnings and redemption transactions for each healthcare system and/or asset owner participating in the UME Gateway.

The AI Powered Asset and Program Performance Analytics and BI engine 820 is a set of AI models and automations that analyzes all asset, service and transactional records a healthcare system or asset owner has in the UME Gateway and generates insights and business intelligence (BI) on how well the healthcare system or asset owner is utilizing the UME Gateway relative to what was expected based on the information in the Digitized Business and Contract Rules and Constraints database 190, as well as how well the UME Gateway is performing when used and where improvements can be made.

The Automated Spreadsheet and PDF Reports generator 822 is a set of AI models and automations that generates reports and datasets about UME Gateway assets, services, and financial transactions formatted as spreadsheets or PDF documents for consumption.

The Asset Stakeholder Communications Engine 830 is a set of automations that pushes information about UME Gateway data, activities, events, transactions, and analytics to healthcare systems and/or asset owners in a variety of ways for them to consume.

The Stakeholder SMS, Email, and App Notifications generator 832 is a set of automations that generate and send SMS messages, emails, or in app notifications.

The Stakeholder Data Translation and Integration Engine 834 translates information sent between the UME Gateway and healthcare systems and/or asset owners to and from the nomenclatures used by each party and manages the UME Gateway endpoints and triggers to push, pull, or receive data. AI models help detect and manage these nomenclature translations as new integrations are created.

The Stakeholder Internal Program Access and Data Consumption process 836 are systems, automations, and processes created and controlled by healthcare systems and/or asset owners to access, route and control information received from or sent to the UME Gateway, and allows interested organizations to bypass or augment the Mobile Apps group 841 and/or the Web Interfaces group 842 to build their own process automations to their CMMS systems or other platforms to automate working with the UME Gateway.

The Active Registered Demand Module 150, which is the same as described in FIG. 1*b* is able to receive process demand for patient ready equipment, parts, and parts units entered by healthcare systems and/or asset owners.

The Customized Stakeholder Self-Service Interfaces group 840 is a set of UME Gateway provided technologies allowing healthcare systems and/or asset owners to access information about their medical devices and services processed by the UME Gateway and to request and buy products and services from the UME Gateway.

The Mobile Apps group 841 is a group of interfaces offered by the UME Gateway and third parties that enable the user to access UME Gateway processed asset information, services performed, and available products and services via an application on the user's mobile device.

The Web Interfaces 842 group is a group of custom portals and online web application programming interfaces (APIs) offered by the UME Gateway that provide access to UME Gateway processed asset information, services performed, and available products and services via a website on the user's web browser.

The Credit Redemption Marketplace 160 which is the same as described in FIG. 1*b* is a marketplace that allows healthcare systems and/or asset owners to multiply UME Gateway earned residual credits from their medical equipment through a credits conversion model. These credits can be used to procure UME Gateway negotiated discounts on medical devices, parts, supplies, training, and other services allowing them to essentially participate with other parties through bartering arrangements. The Credit Redemption Marketplace 160 can be accessed via the Mobile Apps group 841 and the Web Interfaces group 842.

The UME Gateway Program Management engine 844 contains automations and APIs that provide access to all information about a healthcare system and/or asset owner's assets, services, and activities with the UME Gateway for access via the Mobile Apps group 841 and the Web Interfaces group 842.

The Self-Service User Access Controls module 845 is a configuration tool that allows authorized representatives of healthcare systems and/or asset owners to determine who can view and act on their UME Gateway information via the Mobile Apps group 841 and the Web Interfaces group 842 which in turn access the Credit Redemption Marketplace 160 and/or via the UME Gateway Program Management engine 844.

The Healthcare System GPO and ISO Views and Controls module 846 is a configuration tool that allows authorized representatives of GPOs and ISOs who use the UME Gateway to process medical devices on behalf of their customers to selectively provide those customers with controlled views into information in the Credit Redemption Marketplace 160 and/or via the UME Gateway Program Management engine 844 both of which can be accessed via the Mobile Apps group 841 and/or the Web Interfaces group 842.

The Acquisition, Identification, and Evaluation Data and Requests process 850 is a process that allows healthcare systems and/or asset owners or GPOs and ISOs to request the UME Gateway evaluate information about medical devices submitted via files, photos, or data interfaces, or for UME Gateway representatives to perform onsite assessments and pickups of medical equipment.

The Current Inventory Availability Database 851 is a database view of all disposition inventory currently held by the UME Gateway that is currently available to a given healthcare system and/or asset owner for them to request redeployment back to a designated location.

The Redeployment Demand Registry 853 is a database of all open, desired redeployment requests made by a healthcare system and/or asset owner for equipment they wish to receive via redeployment if such equipment comes available from one or more other locations or departments in their organization.

The Redeploy Match Detection process 855 is an automated process the UME Gateway runs periodically to detect and tag available inventory that matches a redeployment request in the Redeployment Demand Registry 853 so the UME Gateway can allocate matching inventory to the redeployment escape path and process the redeployment.

The Automated Work Order Creation process 857 creates redeployment work orders when the Redeploy Match Detection process 855 finds a match and/or a user triggers a redeployment request on an available medical device via either the Mobile Apps group 841 or the Web Interfaces group 842.

The Redeployment Processing Activity 446 which is the same as described in FIG. 4*a* processes redeployment work orders created by the Automated Work Order Creation process 857 so the redeployed medical equipment is pulled, packaged, and delivered to the redeployment recipient.

The Redemption Controls Process 860 is a set of verifications and controls to make sure a healthcare system and/or asset owner's redemption request is validly authorized, the funds are available, and the method and manner of redeeming funds follows a process previously approved by the UME Gateway and that healthcare system and/or asset owner.

The Redemption Remittance or Order Processing process 862 performs the execution of a valid redemption request determined by the Redemption Controls Process 860 and either remits funds or processes orders for products and services paid for by the redemption.

The Buyback and Bartering Process 864 is the same as the Buyback and Bartering Process 770 found in FIG. 7*b* and is specifically triggered when a healthcare system and/or asset owner requests their credits be redeemed for reconditioned medical equipment or parts and the UME Gateway needs to acquire that medical equipment or parts from a reconditioning or parts harvesting trading partner.

The Financial Posting and Reconciliation Engine 180 which is the same as described in FIG. 1*b* is a set of automations that process all healthcare system and/or asset owner redemption transactions into the UME Gateway's accounting system and financial records and the redeeming party's ledger in the Financial Earning and Redemption Events database 818.

The flow of the UME Gateway Healthcare System Asset Stakeholder Communications Engine and Credit Redemptions Marketplace flowchart 800 is described herein. All relevant information about a healthcare system's or asset owner's participation in the UME Gateway and outcomes generated that exist in the Digitized Business and Contract Rules and Constraints database 190, the Medical Device and Disposition Records database 812, the Logistics and Service Events database 813, the Recycling and Sustainability Activity database 815, the Remediate and Redeploy Event Tracker database 816, the Stored Medical Equipment database 817, and the Financial Earning and Redemption Events database 818 are consolidated and made available for direct access by the AI Powered Asset and Program Performance Analytics and BI engine 820 and the Mobile Apps group 841 and the Web Interfaces group 842 in the Customized Stakeholder Self-Service Interfaces group 840. The AI Powered Asset and Program Performance Analytics and BI engine 820 uses its AI models and automations to analyze the use of the UME Gateway by each healthcare system and/or asset owner and generates insights into actual performance against contractual expectations in the Digitized Business and Contract Rules and Constraints database 190, asset level expectations as compared to information in the Medical Device and Disposition Records database 812, and against industry convention and expectations determined by its own AI models that are continuously retrained via semi-supervised AI model training methods using all information available in the UME Gateway. The AI Powered Asset and Program Performance Analytics and BI engine 820 produces insights and recommendations that help a healthcare system and/or asset owner improve their medical equipment disposition program's operational efficiency to lower costs, detect medical equipment disposition compliance and governance issues and root cause which facilities, departments, and/or processes contribute to the issues, improve capital planning and performance by accelerating or decelerating disposition activities based on market conditions and acquiring reconditioned medical devices, parts, and services to optimize their fleet lifetimes. The AI Powered Asset and Program Performance Analytics and BI engine 820 produced insights and recommendations are stored and regularly accessed by the Automated Spreadsheet and PDF Reports generator 822 which converts these insights into predefined spreadsheet data sets and PDF report formats generally useable by healthcare systems and/or asset owners and then pushes them to the Asset Stakeholder Communications Engine 830 along with information about which formatted reports and PDF documents to send to which recipients via which methods based on information gleaned from the Digitized Business and Contract Rules and Constraints database 190 and its own configurations. The Asset Stakeholder Communications Engine 830 informs the Stakeholder SMS, Email, and App Notifications generator 832 to prepare and send SMS, email, and/or mobile application messages containing attachments and/or links to the spreadsheet data sets and/or PDF documents and sends them to the healthcare system and/or asset owner recipients where they are received and processed by whatever method those organizations employ in their Stakeholder Internal Program Access and Data Consumption process 836. In addition to the above any data available to or produced by the AI Powered Asset and Program Performance Analytics and BI engine 820 can also be directly accessed by the Asset Stakeholder Communications Engine 830 which will push it to the Stakeholder Data Translation and Integration Engine 834 to be reformatted into the data structures, formats and naming conventions used by different healthcare systems and/or asset owners that automatically integrate with the UME Gateway. The Stakeholder Data Translation and Integration Engine 834 provides endpoints for the Stakeholder Internal Program Access and Data Consumption process 836 to request information and/or it can push information on scheduled intervals to the Stakeholder Internal Program Access and Data Consumption process 836 where healthcare systems and/or asset owners can integrate the information into their CMMS systems and/or other systems and use the information in their processes in whatever manner they see is most productive. Healthcare systems and/or asset owners can also use any preferred Stakeholder Internal Program Access and Data Consumption process 836 solution they create to automatically push information such as asset pickup or evaluation requests, redeployment requests, medical equipment parts and services demand, and/or redemption requests to the Stakeholder Data Translation and Integration Engine 834 which will format those requests into the structure and nomenclature of the UME Gateway and pass them to interfaces in the Customized Stakeholder Self-Service Interfaces group 840 for processing as defined below. Designated healthcare system and/or asset owner representatives may use the Mobile Apps group 841 and the Web Interfaces group 842 in the Customized Stakeholder Self-Service Interfaces group 840 to connect to the UME Gateway Program Management engine 844 automations and APIs which can access all information available to or generated by the AI Powered Asset and Program Performance Analytics and BI engine 820 and provide them any necessary views, reports spreadsheet or PDFs to track and monitor their UME Gateway disposition program activities and performance. Authorized healthcare system and/or asset owner representatives may use the Self-Service User Access Controls module 845 in the Customized Stakeholder Self-Service Interfaces group 840 to specify which individuals can view and/or act upon each feature or data element available in each of the mobile apps included in the Mobile Apps group 841 and in each of the web interfaces included in the Web Interfaces group 842 to provide different capabilities to different audiences. Similarly, GPOs and ISOs offering UME Gateway disposition programs to their healthcare system customers can use the GPO and ISO Views and Controls module 846 to specify the individuals and detailed capabilities they can perform in the Mobile Apps group 841 and the Web Interfaces group 842. The Self-Service User Access Controls module 845 and the GPO and ISO Views and Controls module 846 share information regarding users with one another. Authorized users may access the Credit Redemption Marketplace 160 via the Mobile Apps group 841 and the Web Interfaces group 842 to request available earnings be used to purchase discounted products and services in the Credit Redemption Marketplace 160 catalog or have their funds remitted to their organization. Redemption requests made to the Credit Redemption Marketplace 160 via the Mobile Apps group 841, the Web Interfaces group 842, or the Stakeholder Data Translation and Integration Engine 834 as described above are passed to the Redemption Controls Process 860 which ensures the request is properly authorized and approved, meets any governance terms and conditions agreed to with the healthcare system and/or asset owners for how their funds may be used, and sufficient funds are available. The Redemption Controls Process 860 will then pass validated requests for funds and/or currently available medical devices, parts and services to the Redemption Remittance or Order Processing process 862 which will use other UME Gateway processes and automations previously described, such as the Asset Stakeholder Communications Engine 830, to process the order and provide the products and services, and/or perform an automated funds transfer or check issuance and notify the Financial Posting and Reconciliation Engine 180 to capture those transactions for UME Gateway accounting and log them in the Financial Earning and Redemption Events database 818. If the Redemption Controls Process 860 receives a request for medical devices or parts that are not currently available and need to be sourced from a reconditioning or parts harvest trading partner it will send that request to the a Buyback and Bartering Process 864 which will use other UME Gateway processes and automations previously described to source and fulfil those medical devices and/or parts and notify the Financial Posting and Reconciliation Engine 180 to capture those transactions for UME Gateway accounting and log them in the Financial Earning and Redemption Events database 818. If, via the Mobile Apps group 841, the Web Interfaces group 842, or the Stakeholder Data Translation and Integration Engine 834 as described above, the Customized Stakeholder Self-Service Interfaces group 840 receives a request for medical devices, parts, or services that are not currently available in inventory or through the Buyback and Bartering Process 864 those request will be passed to the Active Registered Demand Module 150 which will perform its processes and activities as described in FIG. 1*b* and FIG. 5*a* respectively so the item can be sourced or acquired by the UME Gateway. If a healthcare system and/or asset owner via the Mobile Apps group 841, the Web Interfaces group 842, or the Stakeholder Data Translation and Integration Engine 834 as described above generates a request to the Customized Stakeholder Self-Service Interfaces group 840 to make medical equipment available to the UME Gateway through receipt of CMMS records, files, and photos, or by requests for onsite evaluations or equipment pickups these requests are passed to the Acquisition, Identification, and Evaluation Data and Requests process 850 which will process them according the processes and activities described in FIG. 3 and share the results of said processing with the Automated Work Order Creation process 857. If a healthcare system and/or asset owner via the Mobile Apps group 841, the Web Interfaces group 842, or the Stakeholder Data Translation and Integration Engine 834 as described above makes a request to the Customized Stakeholder Self Service-Interfaces group 840 for redeployment of items that may become available in the future it will update the Redeployment Demand Registry 853 with details of the desired medical devices for redeployment. A Redeploy Match Detection process 855 runs continuously checking the Current Inventory Availability database 851 to detect if inventory becomes available that matches a redeployment request in the Redeployment Demand Registry 853 including meeting the redeployment ownership and governance requirements of the healthcare system and/or asset owner organization that made the request. If the Redeploy Match Detection process 855 makes a valid match it places a hold on that medical equipment and sends the information to the Automated Work Order Creation process 857 which creates all the necessary work orders, instructions and tasks in the UME Gateway needed for the Redeployment Processing activity 446 to pick, package, and ship or deliver the redeployed medical equipment to the location designated by the requestor. If a healthcare system and/or asset owner via the Mobile Apps group 841, the Web Interfaces group 842, or the Stakeholder Data Translation and Integration Engine 834 as described above makes a request to the Customized Stakeholder Self Service-Interfaces group 840 to redeploy a piece of currently eligible UME Gateway medical equipment inventory, that request will be passed to the Automated Work Order Creation process 857 which creates all the necessary work orders, instructions and tasks in the UME Gateway needed for the Redeployment Processing activity 446 to pick, package, and ship or deliver the redeployed medical equipment to the location designated by the requestor.

The UME Gateway provides customizable web and mobile app interfaces for healthcare systems and/or asset owners to see a complete view of their unique medical equipment disposition program's performance. This includes the contract commitments, all inbound and outbound logistics events, device level tracking, sustainability and recycling statistics, issue remediation or other value-added services performed, financial ledger transactions, and the ability to trigger changes in equipment that is held in storage or is available for redeployment.

The healthcare systems and/or asset owners can use the customizable web and mobile app interfaces to trigger asset pickup requests, onsite asset evaluations, or send in asset information and photos for evaluation by the UME Gateway.

The healthcare systems and/or asset owners can also request redeployments, credit redemptions, and reports and spreadsheets from the customizable web and mobile app interfaces.

The UME Gateway can be configured to send spreadsheets, reports, data, alerts, messages, approval requests, and other information via SMS messages, emails, or in app mobile notifications for healthcare systems and/or asset owners to process in their preferred tools. Interested healthcare systems and/or asset owners can use the Stakeholder Data Translation and Integration Engine 834 to fully automate all interactions, data, and reporting with the UME Gateway within their own CMMS or other internal systems allowing them to optimally customize and control how their organization interacts with the UME Gateway.

A role and user-based configuration engine enables administrators to address their organization's unique complexities and protocols for how information can be viewed and by whom in their organization as well as who can authorize actions on different types of medical devices or redeem or spend funds. Depending on the healthcare system's and/or asset owner's policies for medical equipment control, accounting, and asset sharing, the UME Gateway can uniquely configure their medical equipment disposition program to be controlled at an enterprise, site, clinical department, or asset category level. Healthcare systems and/or asset owners can restrict the people, pages, fields, event triggers, locations, medical device lists, records, and other information presented. The result is that some users can see selected views of assets without financial details, different views for sites, site groupings, clinical departments, or medical device types can be established. Healthcare systems and/or asset owners can also incorporate their ISOs and GPOs into the tools while these organizations can likewise lead and offer trackable disposition programs to the healthcare systems and/or asset owners they support. Effectively, healthcare systems and/or asset owners can create their own uniquely designed disposition program according to their preferences and governance needs.

Interested healthcare systems and/or asset owners can use the UME Gateway to implement large-scale redeployment programs with access controls across their hospitals and other care points of their enterprise that support asset sharing. Redeployment process orchestration and access rules can be dynamically defined and managed to provide broad visibility to these shareable assets while restricting other medical devices to home locations and departments where policies prohibit sharing. Where redeployments are allowed, site users can pre-register demand for certain assets and monitoring agents will immediately alert them if a match becomes available from another part of their system. The UME Gateway will then trigger and execute the redeployment process automatically.

Items held in storage as well as disposition medical devices that are still available can be viewed, reported on, and digitally reclaimed at any time ensuring nothing is lost or held longer than it should be. Once reclaimed, all work orders and shipping events are triggered for execution and tracking by the UME Gateway until received at the designated destination specified by the healthcare system and/or asset owner. Healthcare systems and/or asset owners can also dynamically transition stored items into escape paths if they determine holding or reclaiming them is no longer needed.

The UME Gateway web portal and mobile interfaces provide reporting and customized sorting, filtering, and views that can be saved for each user including converted to popular PDF, Excel, or other consumable formats. In addition to online and app-based access and user controlled reporting, the UME Gateway offers automated intelligent reporting, alerts, and notifications that can be set by healthcare system and/or asset owner administrators, so they receive the information they need, when they need it, in the format or tool that allows them to take immediate action.

AI agents perform analysis of disposition activities and outcomes and generate dashboards and alerts on performance while hot spotting gaps for users to investigate. For example, the UME Gateway can alert them of unusual disposition activity and volumes in different departments or locations allowing investigation of whether policies are being followed or assets are going missing or lost from unauthorized activities. Likewise, it can alert the user regarding ways to create more efficient asset pickup strategies to avoid costly logistics charges such as consolidating assets locally from multiple nearby sites or switching to less frequent pickup schedules to ensure fuller trucks.

To the extent healthcare systems and/or asset owners can integrate their CMMS or asset management data into the UME Gateway, disposition records can be inserted for end-of-life asset tracking and intelligent recommendations can be made to speed up or slow down disposition of certain assets based on market conditions and impact on capital budgets. The UME Gateway can also automatically recommend ROI from replacement of or switching to rental fleets in lieu of ownership, purchasing parts units to extend the useful life of a valuable fleet, or aftermarket fleet replacement options to a different manufacturer or model.

The UME Gateway tracks and posts all asset and financial transactions into healthcare system and/or asset owner ledgers at site or department levels so funds can be managed in centralized or decentralized ways. Digitized contract terms are automatically applied so every event is captured, and any custom pricing, discounts, service options, and entitlements are applied. Healthcare systems and/or asset owners can custom define their disposition programs in the UME Gateway using a 'la carte service models, fixed price services with entitlement caps, or a combination of the two knowing their unique combination of service levels and performance requirements will be automatically applied. When programs are offered to healthcare systems and/or asset owners via ISOs, GPOs, or other third-parties, the accessible views for each party and financial transaction can be established and controlled by the responsible paying party.

The UME Gateway tightly controls earnings from sales of medical equipment via process orchestrations according to rules set by the healthcare systems and/or asset owners. This allows for department, site, or organization wide controls and prevents using earnings by unauthorized actors or for unintended purposes. AI tracks and audits every transaction to assure governance of the use of funds and intervenes when anomalies are detected. For those organizations authorized to use credits to purchase products and services, a marketplace of refurbished medical devices, parts, training, and services from third-party providers is made available. Healthcare systems and/or asset owners can choose to include or exclude specific solutions from their personalized redemption marketplaces. Using the credit redemption marketplace significantly streamlines difficult to manage one-off small capital procurement events and medical equipment and service marketplace sourcing from smaller vendors for the healthcare systems and/or asset owners.

AI driven analytics and other marketing automation tools can track UME participating healthcare system and/or asset owner activities and recommend deals, incentives, and boosters for using credits to acquire selected types of products and services available from the marketplace. This effectively increases earnings from selling disposition medical equipment through the UME Gateway by multiplying the purchasing power of those earnings. Participating healthcare systems and/or asset owners can also register demand for patient-ready equipment and services to have them sourced and fulfilled by the UME Gateway for a fee. Any redemptions for product and services are processed with the UME Gateway and recorded against the financial ledgers.

It is to be understood that a mobile device may be any appropriate portable computing device, such as a smart phone, laptop, tablet PC, smart watch, mobile internet devices, wearable computers, personal digital assistants, enterprise digital assistants, handheld game consoles, portable media players, ultra-mobile PCs, and/or smart cards, as non-limiting examples.

Non-limiting aspects have been described, hereinabove. It will be apparent to those skilled in the art that the above methods and apparatuses may incorporate changes and modifications without departing from the general scope of the present subject matter. It is intended to include all such modifications and alterations in so far as they come within the scope of the appended claims or the equivalents thereof.

Having thus described the disclosure, it is now claimed:

We claim:

1. A system for selling, processing, and/or refurbishing medical equipment, the system comprising one or more computer-readable storage media containing a set of instructions executable by one or more logic machines to perform the steps of:

collecting data on at least one piece of medical equipment;

evaluating the at least one piece of medical equipment;

using AI driven analytics, making a recommendation regarding how much investment to make in identifying additional details about the at least one piece of medical equipment, wherein the set of instructions encoded on the non-transitory computer-readable storage medium comprises an AI enhanced engine, wherein the AI enhanced engine takes the step of making a recommendation regarding how much investment to make in identifying additional details about the at least one piece of medical equipment is executed iteratively and repeatedly, wherein the system can dynamically change its recommendations regarding the at least one piece of medical equipment based on new or changed information;

the AI enhanced engine uses econometric data to evaluate the at least one piece of medical equipment, wherein the econometric data comprises demand, supply, and transactional data from within and outside the system;

the AI enhanced engine normalizes transactional and demand data by weighting the transactional and demand data using available information on recency, seasonal timing, volumes, number of transactions, channels where the transaction occurs, and any other medical equipment purchased or quoted simultaneously;

the AI enhanced engine uses an acquisition and identification capture process, wherein incoming medical equipment are identified, photographed, and entered into the system;

the AI driven analytics used in making the recommendation regarding how much investment to make in identifying additional details about the at least one piece of medical equipment utilizes at least one of the following data sets in making the recommendation:

manufacturer, model, quantity, condition, specification data, accessories, transaction history, registered demand, terms, quotes, offers, market supply data, market pricing signals, available compatible inventory, lotting options, kitting options, refurbishment valuation predictions, refurbishment costs, parts harvest valuation predictions, and parts harvest costs;

the AI driven analytics used in making the recommendation regarding how much investment to make in identifying additional details about the at least one piece of medical equipment utilizes seller contract rules and constraints in making the recommendation, wherein models used by the AI enhanced engine are continuously enhanced using transactional, demand, and supply data;

the system assesses potential benefit of making value added investments of labor, logistics, and accessories into the at least one piece of medical equipment;

models used by the AI enhanced engine identify gaps in data, metadata and master data and automatically fill them in or generate alerts for manual intervention;

models used by the AI enhanced engine perform prework in sourcing relevant market data and either process the relevant market data into a consumable format or present the relevant market data to a user;

using AI driven analytics, automatically making a recommendation regarding ideal pricing and escape path for at least one piece of medical equipment based on collected data on the at least one piece of medical equipment, wherein the set of instructions encoded on the non-transitory computer-readable storage medium comprises an AI enhanced engine, wherein the escape path comprises:

a store path, a redeploy path, a recondition path, a harvest path, a multi-channel resale path, a donate path, and a remediate or recycle path;

the step of making a recommendation regarding ideal pricing and escape path for at least one piece of medical equipment based on collected data on the at least one piece of medical equipment is executed iteratively and repeatedly, wherein the system can dynamically change its recommendations regarding the at least one piece of medical equipment based on new or changed information, wherein the AI enhanced engine uses econometric data to evaluate the at least one piece of medical equipment, wherein the econometric data comprises demand, supply, and transactional data from within and outside the system;

models used by the AI enhanced engine normalizes data across a variety of factors to determine ultimate potential pocket margin returns from different medical equipment escape path alternatives along with assessing confidence in the recommendations, wherein the factors are at least one of the following:

demand, supply, manufacturer, model, quantity, condition, specification data, accessories, transaction history, registered demand, terms, quotes, offers, market supply data, market pricing signals, available compatible inventory, lotting options, kitting options, refurbishment valuation predictions, refurbishment costs, parts harvest valuation predictions, parts harvest costs, recency, seasonal timing, volumes, number of transactions, and channels where the transaction occurs;

the AI enhanced engine uses at least one of the following data sets to gain insight for recommending listing price points, anticipated results of negotiations, and potential guidance where quotes and offers may have been too high or too low:

quote history, offer history, current negotiations, and negotiation history;

the AI enhanced engine utilizes quality control methods to ensure that there are no anomalies in information used by the system to make the recommendation; and the AI enhanced engine dynamically controls factors that the system uses to make the recommendation.

* * * * *